US011753758B2

United States Patent
McGinnity et al.

(10) Patent No.: US 11,753,758 B2
(45) Date of Patent: Sep. 12, 2023

(54) ARTICLE OF FOOTWEAR WITH UPPER HAVING STITCHED POLYMER THREAD PATTERN AND METHODS OF MAKING THE SAME

(71) Applicant: adidas AG, Herzogenaurach (DE)

(72) Inventors: Jason Daniel McGinnity, Portland, OR (US); Janette P. Atkins, Portland, OR (US); Elise Marie Hall, Portland, OR (US); Carl Arnese, Portland, OR (US)

(73) Assignee: adidas AG, Herzogenaurach (DE)

( * ) Notice: Subject to any disclaimer, the term of this patent is extended or adjusted under 35 U.S.C. 154(b) by 0 days.

(21) Appl. No.: 17/662,539

(22) Filed: May 9, 2022

(65) Prior Publication Data

US 2022/0333286 A1     Oct. 20, 2022

Related U.S. Application Data

(63) Continuation of application No. 16/531,505, filed on Aug. 5, 2019, now Pat. No. 11,326,290, which is a
(Continued)

(51) Int. Cl.
*D05C 17/02* (2006.01)
*A43B 23/02* (2006.01)
(Continued)

(52) U.S. Cl.
CPC ............ *D05C 17/02* (2013.01); *A43B 9/02* (2013.01); *A43B 23/025* (2013.01);
(Continued)

(58) Field of Classification Search
CPC .... D05C 17/02; D05C 17/023; D05C 17/026; A43B 23/025; A43B 23/0255;
(Continued)

(56) References Cited

U.S. PATENT DOCUMENTS 2,515,050 A   7/1950   L'Hollier
3,444,590 A   5/1969   Ludwig
(Continued)

FOREIGN PATENT DOCUMENTS

CA     2 330 517 C    1/2005
CN     105996284 A    10/2016
(Continued)

OTHER PUBLICATIONS

Jones, Riley, "The 5 Best Shoes to Buy for CrossFit," http://footwearnews.com/2016/focus/athletic-outdoor/5-best-shoes-for-crossfit-2016-290455, Dec. 29, 2016.
(Continued)

*Primary Examiner* — Danny Worrell
(74) *Attorney, Agent, or Firm* — Sterne, Kessler, Goldstein & Fox P.L.L.C.

(57) ABSTRACT

An upper for an article of footwear, the upper including a base layer defining a least a portion of the upper and polymer threads stitched to the base layer. The polymer threads may include a core composed of a first material and a coating composed of a second material, where the melting point of the first material is higher than the melting point of the second material. The polymer threads may be bonded to the base layer by the coating of the polymer threads. The polymer threads may include one or more polymer thread sets stitched in pattern(s) on area(s) of an outer surface of the base layer to provide targeted characteristics to area(s) on the upper. In some embodiments, the polymer threads may be bonded to the base layer with heat and/or pressure.

22 Claims, 30 Drawing Sheets

Related U.S. Application Data continuation of application No. 15/591,972, filed on May 10, 2017, now Pat. No. 10,370,785, which is a continuation of application No. 15/452,672, filed on Mar. 7, 2017, now Pat. No. 10,194,714.

(51) Int. Cl.
| | |
|---|---|
| *A43B 9/02* | (2006.01) |
| *A61B 5/0205* | (2006.01) |
| *A41D 31/00* | (2019.01) |
| *A43B 7/06* | (2006.01) |
| *A43D 3/04* | (2006.01) |
| *A61B 5/024* | (2006.01) |
| *B29D 35/00* | (2010.01) |
| *B29D 35/12* | (2010.01) |
| *B29D 35/14* | (2010.01) |
| *A61B 5/01* | (2006.01) |
| *A61B 5/103* | (2006.01) |
| *A61B 5/11* | (2006.01) |
| *A61B 5/145* | (2006.01) |
| *A61B 5/00* | (2006.01) |
| *A43B 3/34* | (2022.01) |
| *A43B 1/04* | (2022.01) |

(52) U.S. Cl.
CPC .......... *A43B 23/027* (2013.01); *A43B 23/028* (2013.01); *A43B 23/0255* (2013.01); *A61B 5/0205* (2013.01); *A41D 31/00* (2013.01); *A43B 1/04* (2013.01); *A43B 3/34* (2022.01); *A43B 7/06* (2013.01); *A43B 23/0205* (2013.01); *A43B 23/0215* (2013.01); *A43B 23/0235* (2013.01); *A43B 23/0265* (2013.01); *A43B 23/0295* (2013.01); *A43D 3/04* (2013.01); *A43D 2200/60* (2013.01); *A61B 5/01* (2013.01); *A61B 5/02438* (2013.01); *A61B 5/1038* (2013.01); *A61B 5/11* (2013.01); *A61B 5/14542* (2013.01); *A61B 5/14546* (2013.01); *A61B 5/6807* (2013.01); *B29D 35/0054* (2013.01); *B29D 35/0072* (2013.01); *B29D 35/126* (2013.01); *B29D 35/128* (2013.01); *B29D 35/146* (2013.01)

(58) Field of Classification Search
CPC ... A43B 23/0205; A43B 23/0235; A43B 1/04; A43B 9/02
See application file for complete search history.

(56) References Cited

U.S. PATENT DOCUMENTS

| | | | |
|---|---|---|---|
| 4,831,094 A | 5/1989 | Stein et al. | |
| 5,057,252 A | 10/1991 | Kagawa et al. | |
| 5,680,825 A | 10/1997 | Humble | |
| 6,388,043 B1 | 5/2002 | Langer et al. | |
| 6,558,784 B1 | 5/2003 | Norton et al. | |
| 6,910,288 B2 | 6/2005 | Dua | |
| 7,230,047 B2 | 6/2007 | Issari | |
| 7,422,714 B1 | 9/2008 | Hood et al. | |
| 7,622,069 B1 | 11/2009 | Kia et al. | |
| 7,992,243 B2 | 8/2011 | Cook et al. | |
| 8,101,689 B2 | 1/2012 | Tong et al. | |
| 8,109,536 B2 | 2/2012 | Labonte | |
| 8,464,441 B2 | 6/2013 | Meschter et al. | |
| 8,578,534 B2 | 11/2013 | Langvin et al. | |
| 8,590,345 B2 | 11/2013 | Sokolowski et al. | |
| 8,608,890 B2 | 12/2013 | Everhart et al. | |
| 8,800,172 B2 | 8/2014 | Dua et al. | |
| 8,839,530 B2 | 9/2014 | Smith et al. | |
| 8,910,313 B2 | 12/2014 | Gordon et al. | |
| 8,961,723 B2 | 2/2015 | Langvin et al. | |
| 8,997,530 B1 | 4/2015 | Podhajny | |
| 9,107,479 B2 | 8/2015 | Hanson et al. | |
| 9,114,570 B2 | 8/2015 | Downs et al. | |
| 9,241,531 B2 | 1/2016 | Dojan et al. | |
| 9,491,987 B2 | 11/2016 | Antonelli et al. | |
| 10,194,714 B2 * | 2/2019 | McGinnity | A43B 23/0295 |
| 10,370,785 B2 * | 8/2019 | McGinnity | A43B 23/025 |
| 10,779,616 B2 | 9/2020 | Becker et al. | |
| 10,960,630 B2 | 3/2021 | Schneider et al. | |
| 11,326,290 B2 * | 5/2022 | McGinnity | A43B 23/025 |
| 2002/0020080 A1 | 2/2002 | Duclos | |
| 2002/0023306 A1 | 2/2002 | Sajedi et al. | |
| 2003/0115769 A1 | 6/2003 | Morlacchi et al. | |
| 2004/0078089 A1 | 4/2004 | Ellis et al. | |
| 2004/0118018 A1 | 6/2004 | Dua | |
| 2006/0048413 A1 | 3/2006 | Sokolowski et al. | |
| 2007/0151656 A1 | 7/2007 | Gager et al. | |
| 2009/0072436 A1 | 3/2009 | Dean | |
| 2009/0076772 A1 | 3/2009 | Hinshaw et al. | |
| 2010/0084083 A1 | 4/2010 | Hull et al. | |
| 2010/0175276 A1 | 7/2010 | Dojan et al. | |
| 2010/0199520 A1 | 8/2010 | Dua et al. | |
| 2010/0326591 A1 | 12/2010 | Langvin et al. | |
| 2011/0000106 A1 | 1/2011 | Baychar | |
| 2011/0054610 A1 | 3/2011 | Ellis et al. | |
| 2011/0088285 A1 | 4/2011 | Dojan et al. | |
| 2011/0107621 A1 | 5/2011 | Mordecai et al. | |
| 2011/0277250 A1 | 11/2011 | Langvin et al. | |
| 2012/0117823 A1 | 5/2012 | Meschter et al. | |
| 2012/0198730 A1 | 8/2012 | Burch et al. | |
| 2013/0047471 A1 | 2/2013 | Liang | |
| 2013/0232815 A1 | 9/2013 | Meythaler et al. | |
| 2013/0260104 A1 | 10/2013 | Dua et al. | |
| 2013/0269209 A1 | 10/2013 | Lang et al. | |
| 2013/0291317 A1 | 11/2013 | Hanson et al. | |
| 2014/0059886 A1 | 3/2014 | Lyttle et al. | |
| 2014/0075688 A1 | 3/2014 | Langvin et al. | |
| 2014/0134378 A1 | 5/2014 | Downs et al. | |
| 2014/0180866 A1 | 6/2014 | Gonzales | |
| 2014/0223671 A1 | 8/2014 | Fisher et al. | |
| 2014/0259760 A1 | 9/2014 | Dojan et al. | |
| 2014/0310986 A1 | 10/2014 | Tamm et al. | |
| 2015/0013187 A1 | 1/2015 | Taniguchi et al. | |
| 2015/0052778 A1 | 2/2015 | Kirk et al. | |
| 2015/0272274 A1 | 10/2015 | Berns et al. | |
| 2015/0282565 A1 | 10/2015 | Kilgore | |
| 2016/0021979 A1 | 1/2016 | Iuchi et al. | |
| 2016/0053434 A1 | 2/2016 | Feng et al. | |
| 2016/0058105 A1 | 3/2016 | Mordecai et al. | |
| 2016/0088895 A1 | 3/2016 | Viniero et al. | |
| 2016/0135543 A1 | 5/2016 | Anceresi et al. | |
| 2016/0180440 A1 | 6/2016 | Dibenedetto et al. | |
| 2016/0185062 A1 | 6/2016 | Boucher et al. | |
| 2016/0295971 A1 | 10/2016 | Arnese et al. | |
| 2017/0245582 A1 | 8/2017 | Green et al. | |
| 2017/0325545 A1 | 11/2017 | Becker et al. | |
| 2017/0325546 A1 | 11/2017 | Becker et al. | |
| 2017/0327985 A1 | 11/2017 | Ngene et al. | |
| 2017/0348935 A1 | 12/2017 | Leimer et al. | |
| 2018/0255875 A1 | 9/2018 | McGinnity et al. | |

FOREIGN PATENT DOCUMENTS

| | | |
|---|---|---|
| CN | 106028861 A | 10/2016 |
| EP | 2805638 A1 | 11/2014 |
| EP | 2815668 A1 | 12/2014 |
| EP | 2 862 969 A1 | 4/2015 |
| EP | 3 075 277 A2 | 10/2016 |
| EP | 3 078 287 A1 | 10/2016 |
| KR | 10-0626160 B1 | 9/2006 |
| KR | 10-0903193 B1 | 6/2009 |
| WO | WO 2014/207325 A1 | 12/2014 |
| WO | WO 2017/083550 A1 | 5/2017 |

OTHER PUBLICATIONS

Hammer, Armen, "Another Look at the New Nike Metcon 3 FloElite," http://www.floelite.com/article/47636-another-look-at-the-new-nike-metcon-3#.WPpDA00zWpp, Oct. 25, 2016.

(56) References Cited

OTHER PUBLICATIONS

Hammer, Armen, "Nike Metcon 3's Leaked," http://www.floelite.com/article/43584-nike-metcon-3-s-leaked#.WPpDZ00zWpp, Jul. 13, 2016.
International Search Report and Written Opinion of the International Searching Authority for PCT/IB2018/051494, dated Aug. 9, 2018, 16 pages.

* cited by examiner

ARTICLE OF FOOTWEAR WITH UPPER HAVING STITCHED POLYMER THREAD PATTERN AND METHODS OF MAKING THE SAME

CROSS-REFERENCE TO RELATED APPLICATIONS

This application is a continuation of and claims priority to U.S. application Ser. No. 16/531,505, filed on Aug. 5, 2019, which is a continuation of U.S. application Ser. No. 15/591,972, filed on May 10, 2017, which is a continuation of U.S. application Ser. No. 15/452,672, filed on Mar. 7, 2017. Each of these applications is incorporated herein by reference in their entirety.

FIELD

The described embodiments generally relate to an article of wear, such as an upper for an article of footwear or an article of apparel, with polymer threads stitched in one or more patterns on the article. In particular, described embodiments relate to uppers with stitched patterns of polymer threads that are bonded to a base material and provide desired characteristics to areas of the base material.

BACKGROUND

Individuals are often concerned with the durability, weight, and/or breathability of an article of footwear. This is true for articles of footwear worn for non-performance activities, such as a leisurely stroll, and for performance activities, such as running. Durable footwear will properly function for an extended period of time. Lightweight footwear minimizes the weight an individual must carry on his or her feet and may be comfortable for an individual. Breathable footwear may increase comfort for an individual by wicking sweat and heat away from an individual's foot.

For some individuals, for example athletes, stability and propulsion may be desired characteristics for an article of footwear. Footwear that facilitates propulsion (e.g., forward and/or upward motion) may help an athlete perform at an optimal athletic level. Stability for footwear, an in particular stability in portions supporting the ankles of an individual, may reduce the chance of injury to the individual's feet.

Proper footwear should be durable, comfortable, and provide other beneficial characteristics for an individual. Therefore, a continuing need exists for innovations in footwear and fabrics used to manufacture the footwear.

BRIEF SUMMARY OF THE INVENTION

Some embodiments are directed to an upper for an article of footwear, the upper including a base layer defining at least a portion of the upper and one or more polymer threads stitched to the base layer, the one or more polymer threads having a core including a first material and a coating including a second material, where the melting point of the first material is higher than the melting point of the second material, where the one or more polymer threads include a first polymer thread set stitched in a first pattern on an outer surface of the base layer, the first pattern including polymer thread lines oriented in a first direction and a second polymer thread set stitched in a second pattern on the outer surface of the base layer, the second pattern including polymer thread lines oriented in a second direction different from the first direction, where at least a portion of the first polymer thread set overlaps at least a portion of the second polymer thread set in an overlap area, and where at least a portion of the first polymer thread set is bonded to the base layer in the overlap area via the coating of the polymer thread in the first polymer thread set.

Some embodiments are directed to an upper for an article of footwear, the upper including a base layer defining a least a portion of the upper and one or more polymer threads stitched to the base layer, the one or more polymer threads having a core including a first material and a coating including a second material, where the melting point of the first material is higher than the melting point of the second material, where the one or more polymer threads are bonded to the base layer via the coating of the polymer thread, and where the one or more polymer threads include a first polymer thread set stitched in a first pattern on a first area of an outer surface of the base layer.

Some embodiments are directed to an article of footwear including a sole and an upper coupled to the sole, the upper including a base layer defining a least a portion of the upper and one or more polymer threads stitched to the base layer in one or more patterns on a surface of the base layer, the one or more polymer threads including a thermoplastic material coating that bonds the polymer threads to the base layer.

Some embodiments are directed to a method of making an article of footwear, the method including stitching one or more polymer threads in one or more patterns on an outer surface of a base layer, the one or more polymer threads having a core including a first material and a coating including a second material, where the melting point of the first material is higher than the melting point of the second material; bonding the one or more polymer threads to the base layer by heating the second material of the one or more polymer threads to a minimum temperature; and coupling the base layer to one or more footwear components to form an article of footwear.

BRIEF DESCRIPTION OF THE DRAWINGS/FIGURES

Figure 9A:
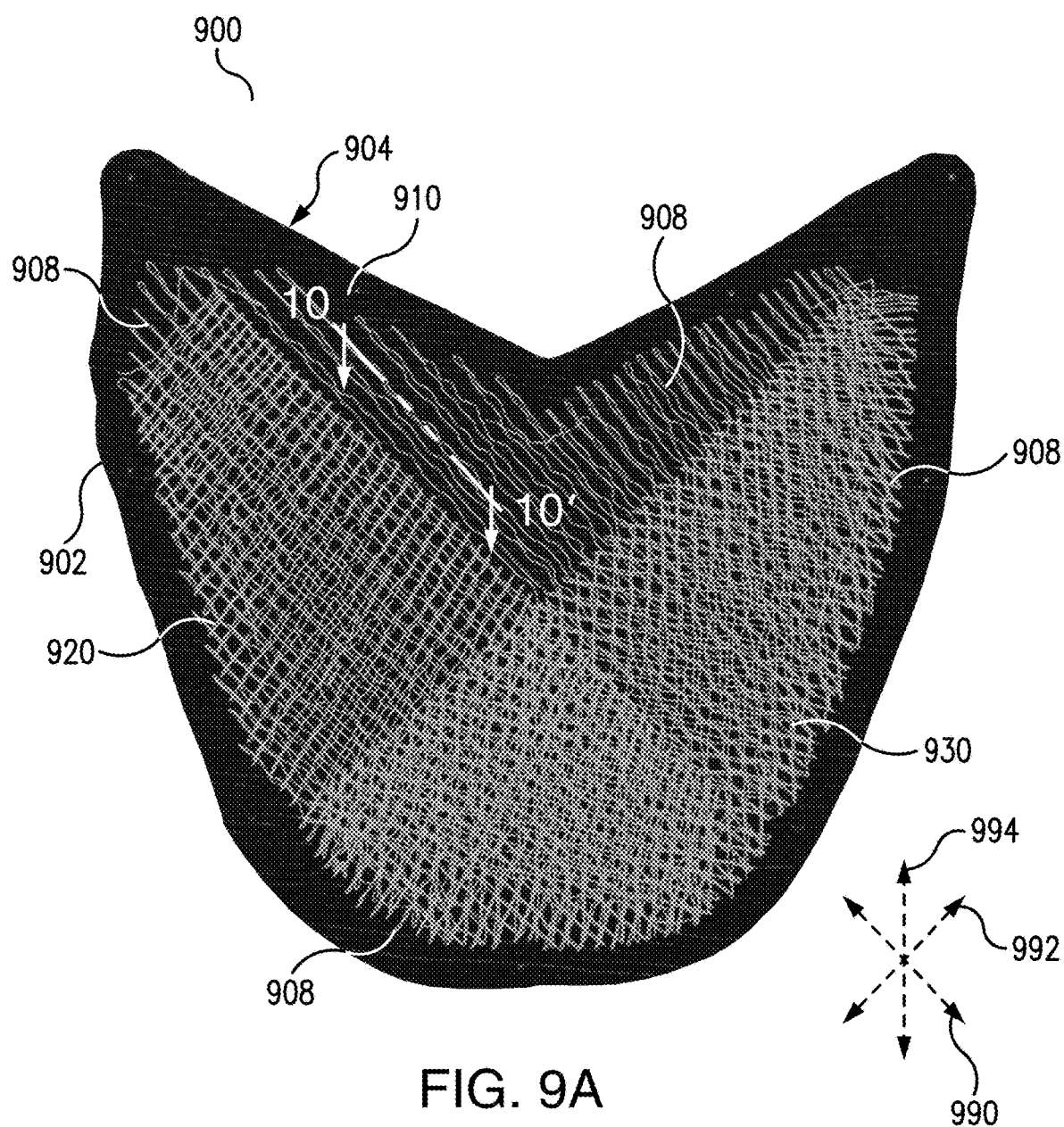
Figure 9B:
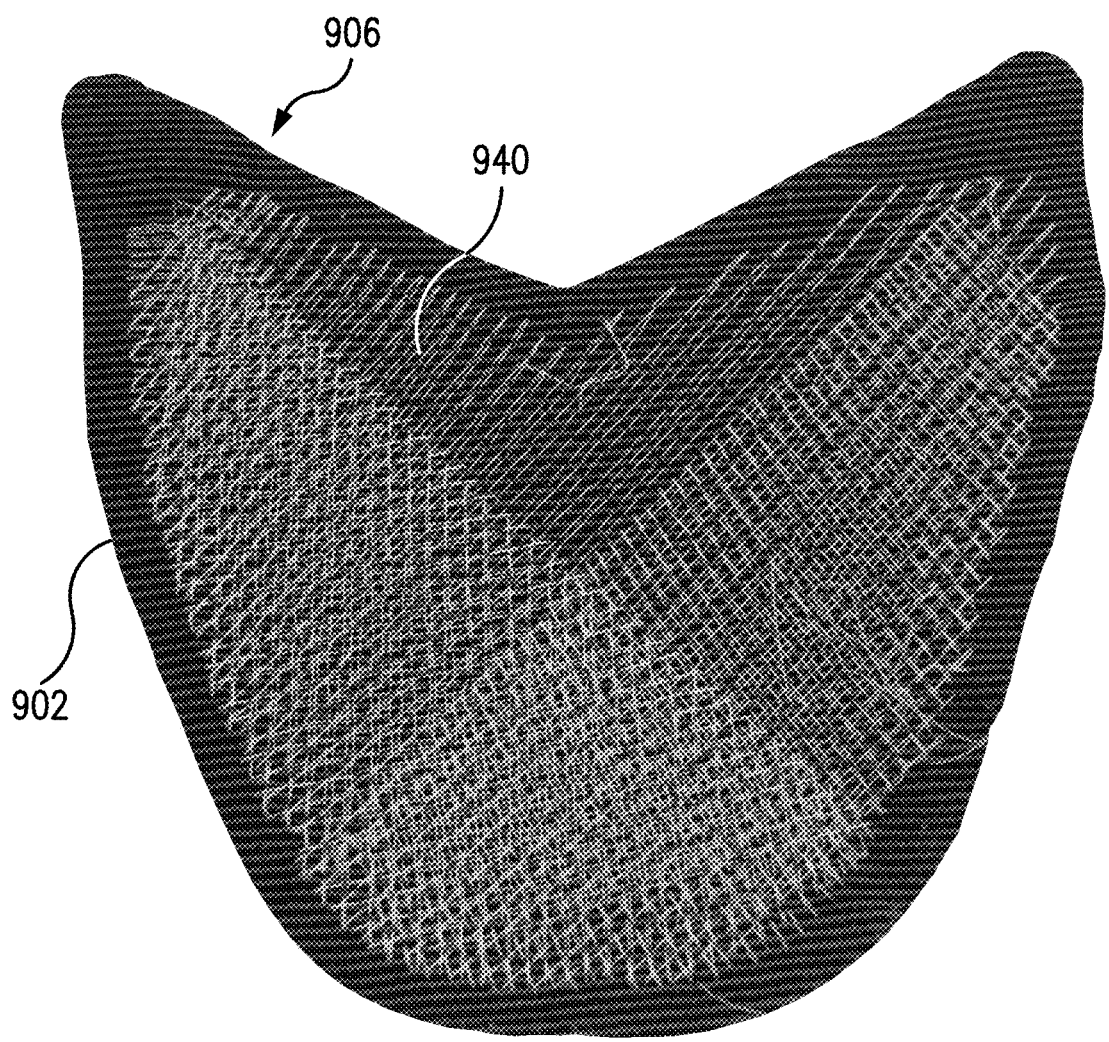
Figure 9C:
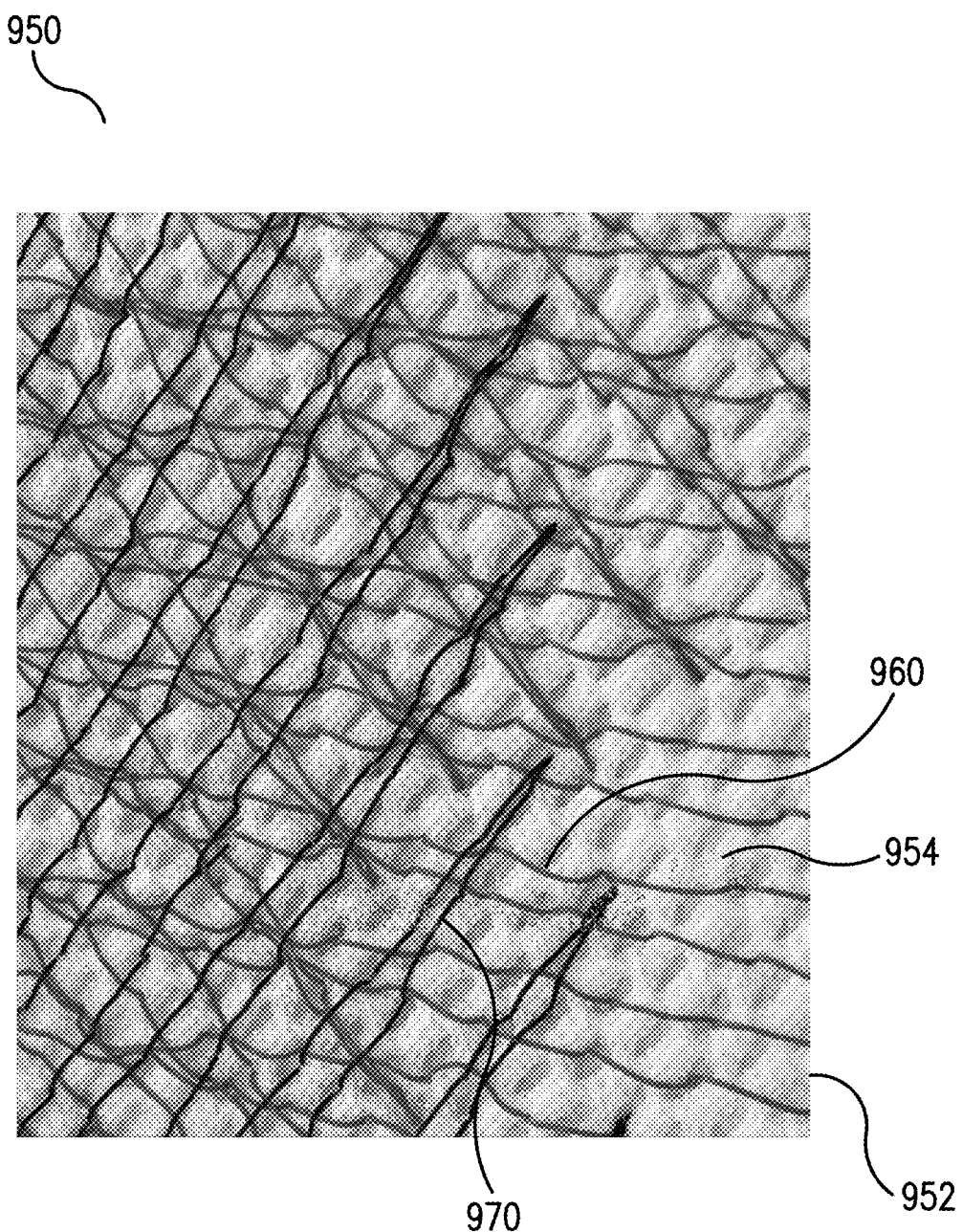

FIG. 9A shows a top surface of a base layer with polymer threads stitched on the base layer according to some embodiments. FIG. 9B shows the bottom surface of the base layer shown in FIG. 9A. FIG. 9C shows a portion of a top surface of a base layer with polymer threads stitched on the base layer according to some embodiments.

Figure 10:
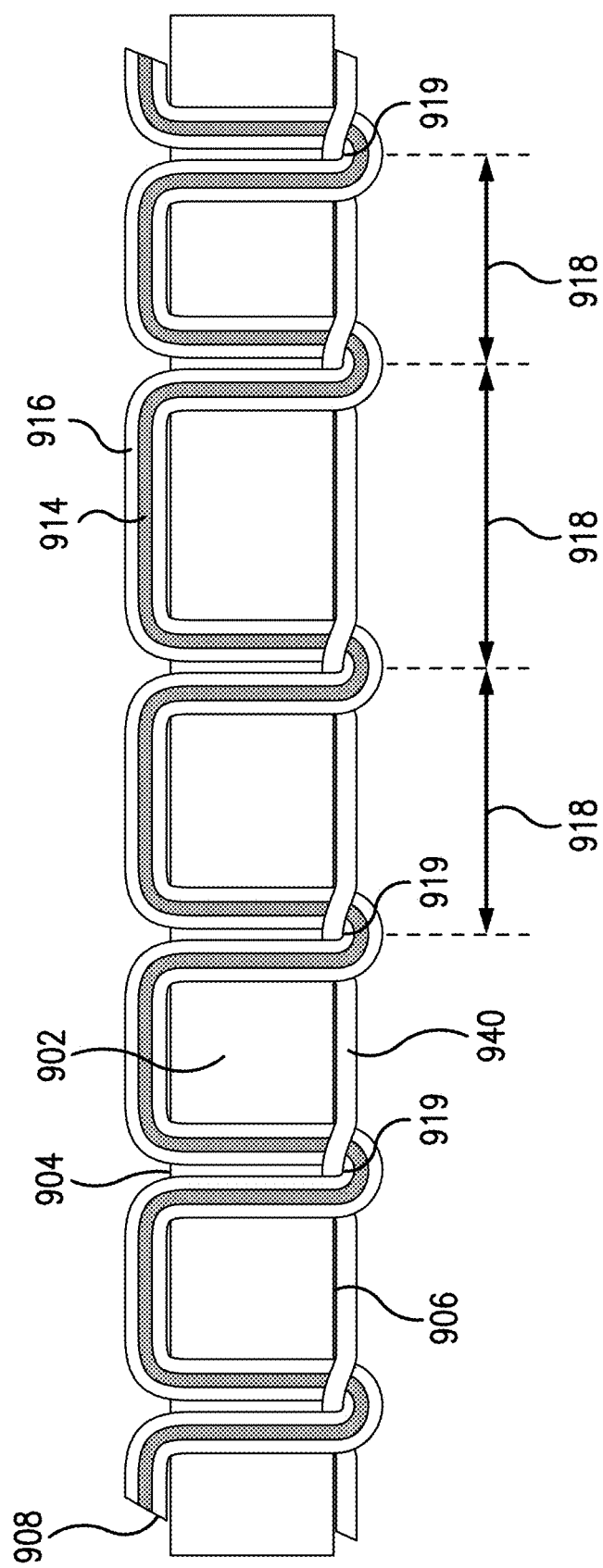

FIG. 10 is a cross-sectional view of the base layer in FIG. 9A along the line 10-10' in FIG. 9A.

Figure 11A:
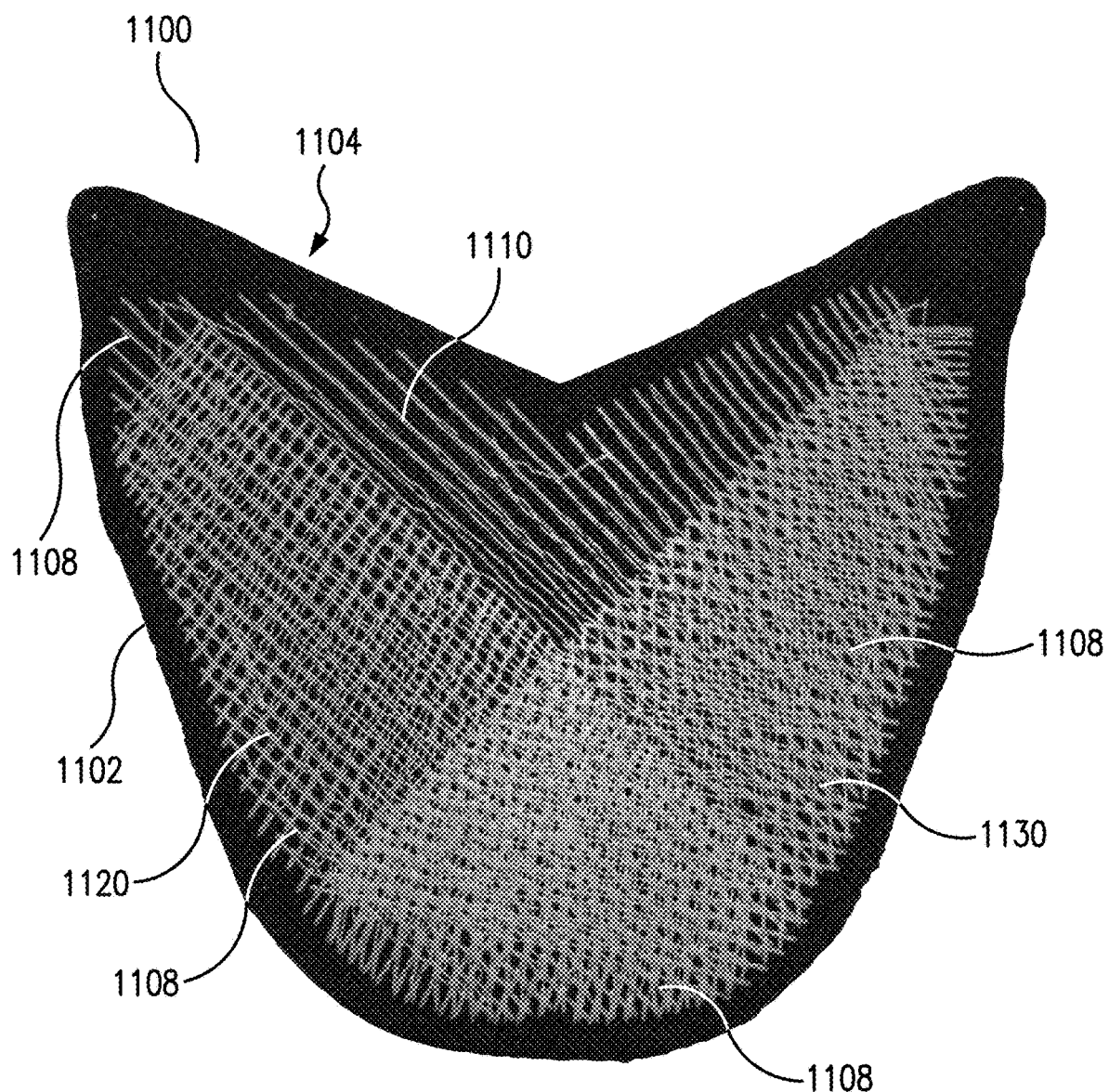
Figure 11B:
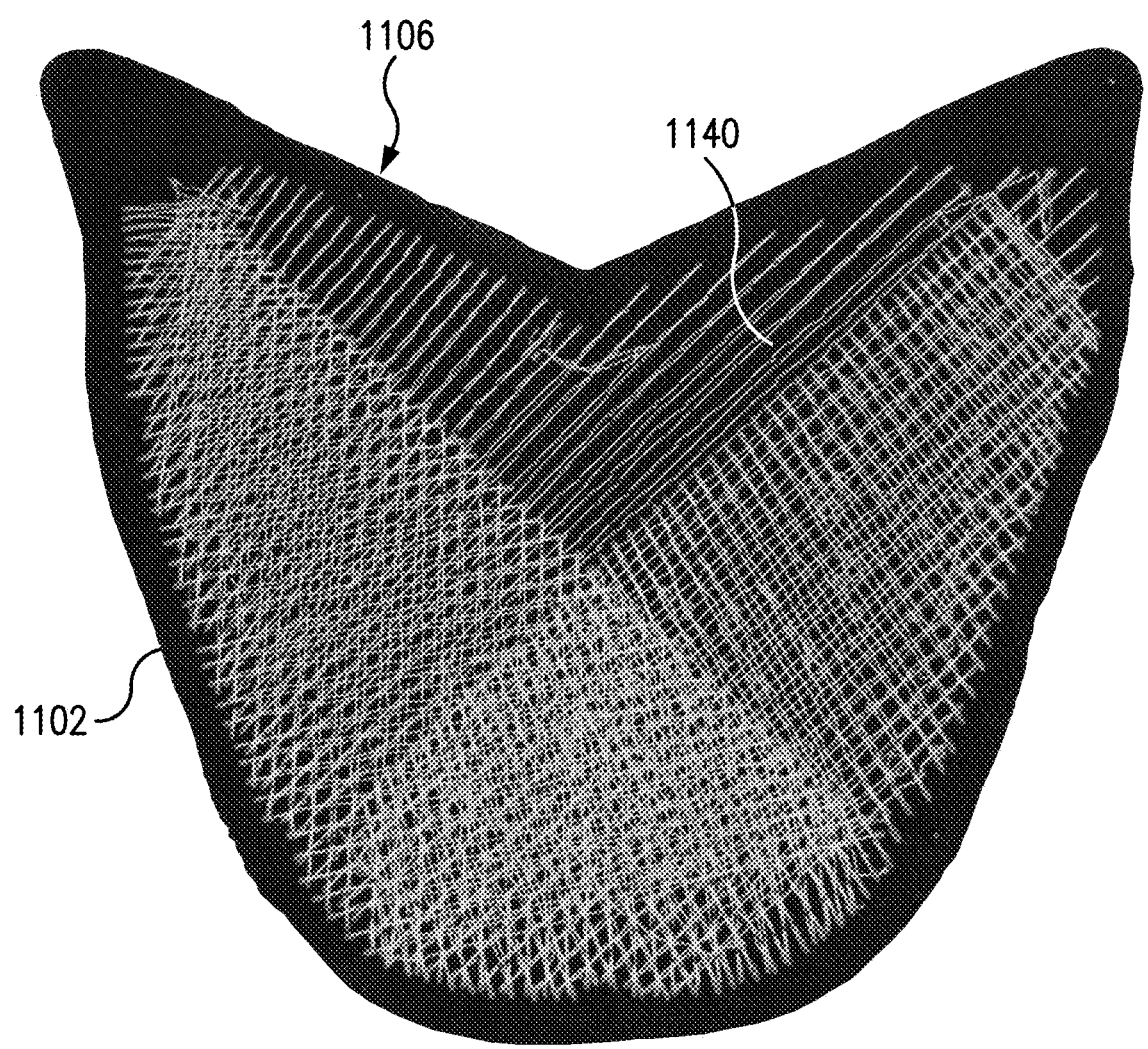
Figure 11C:
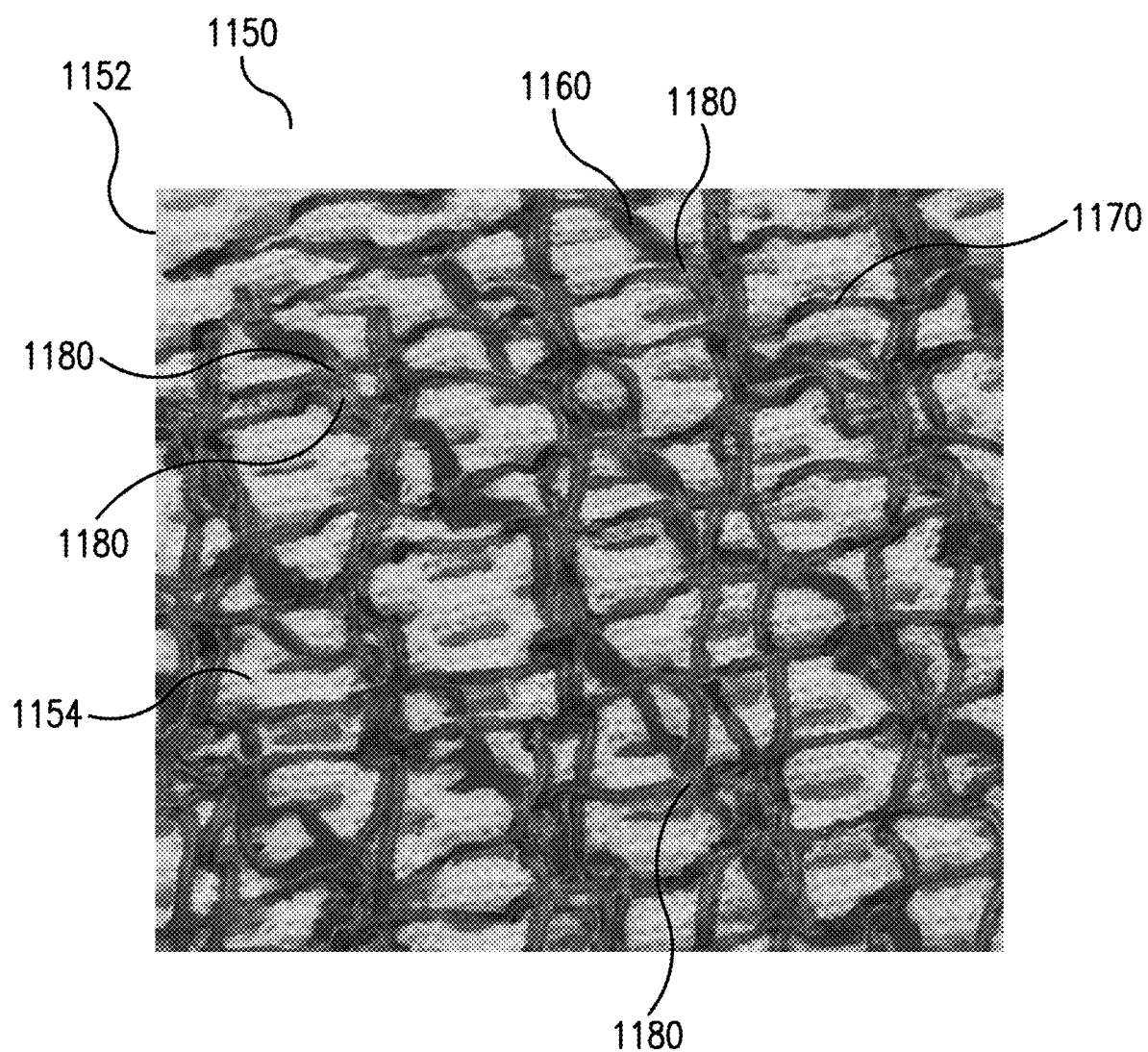

FIG. 11A shows a top surface of a base layer with polymer threads stitched on the base layer and bonded to the top surface according to some embodiments. FIG. 11B shows the bottom surface of the base layer shown in FIG. 11A. FIG. 11C shows a portion of a top surface of a base layer with polymer threads stitched on the base layer and bonded to the top surface according to some embodiments.

Figure 12A:
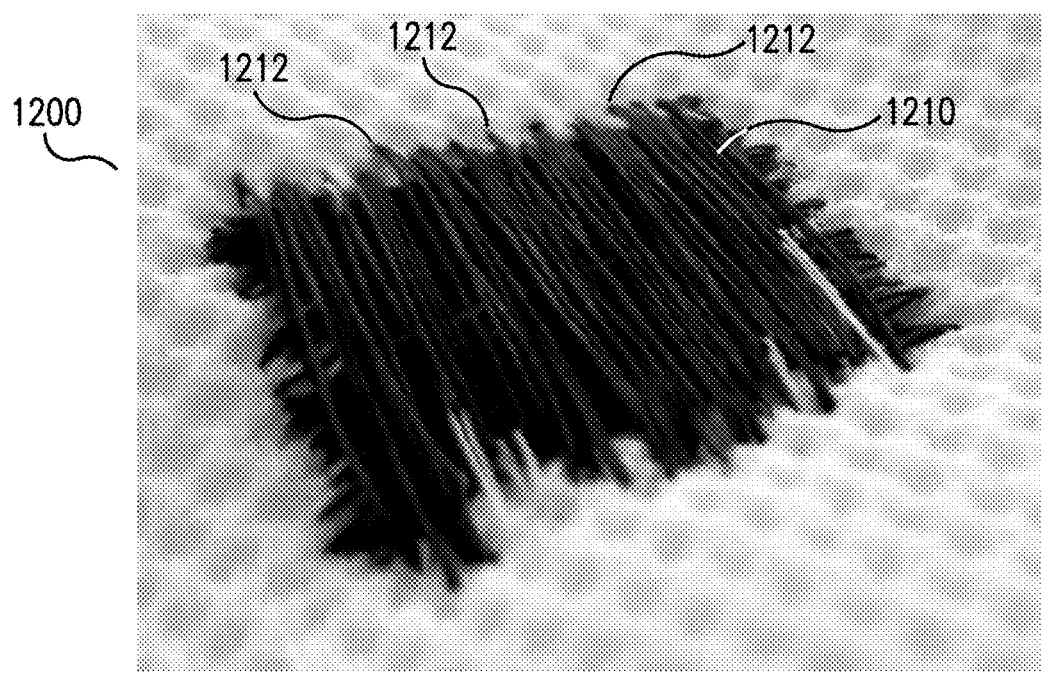
Figure 12B:
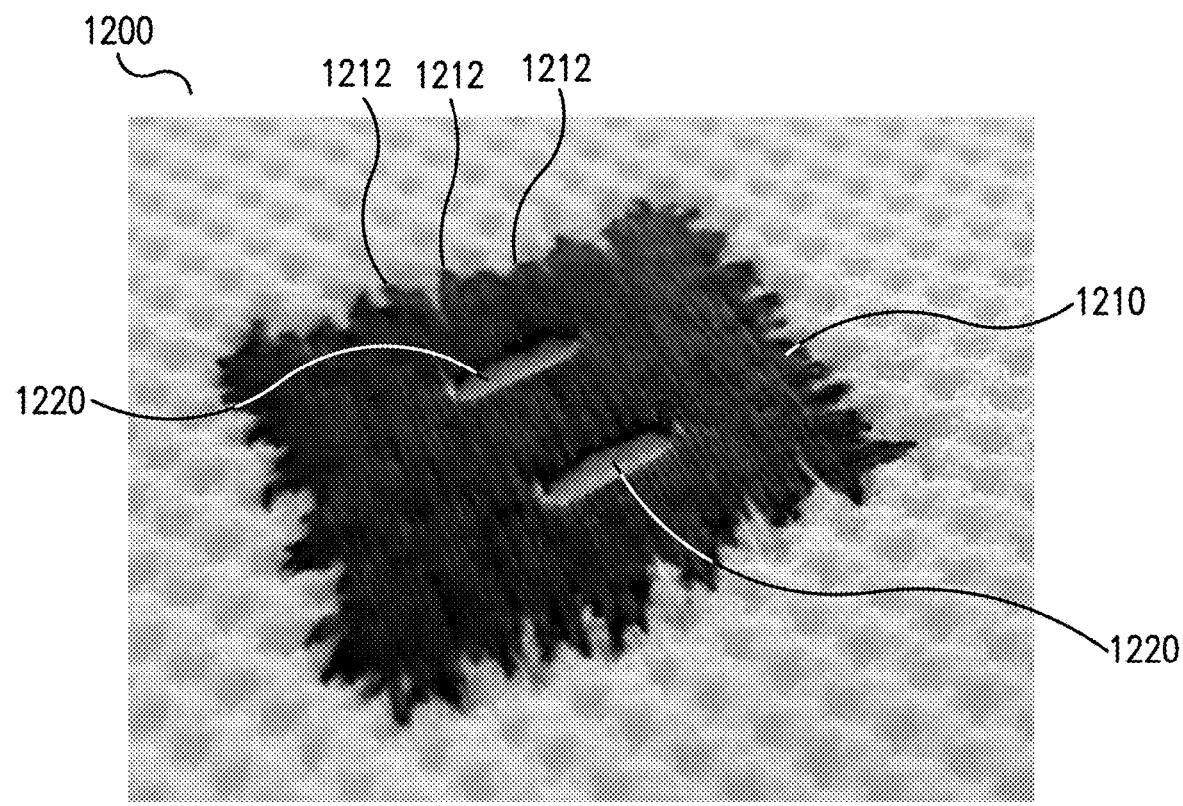

FIG. 12A is an eyelet blank according to some embodiments. FIG. 12B is an eyelet blank with eyelets according to some embodiments.

Figure 13:
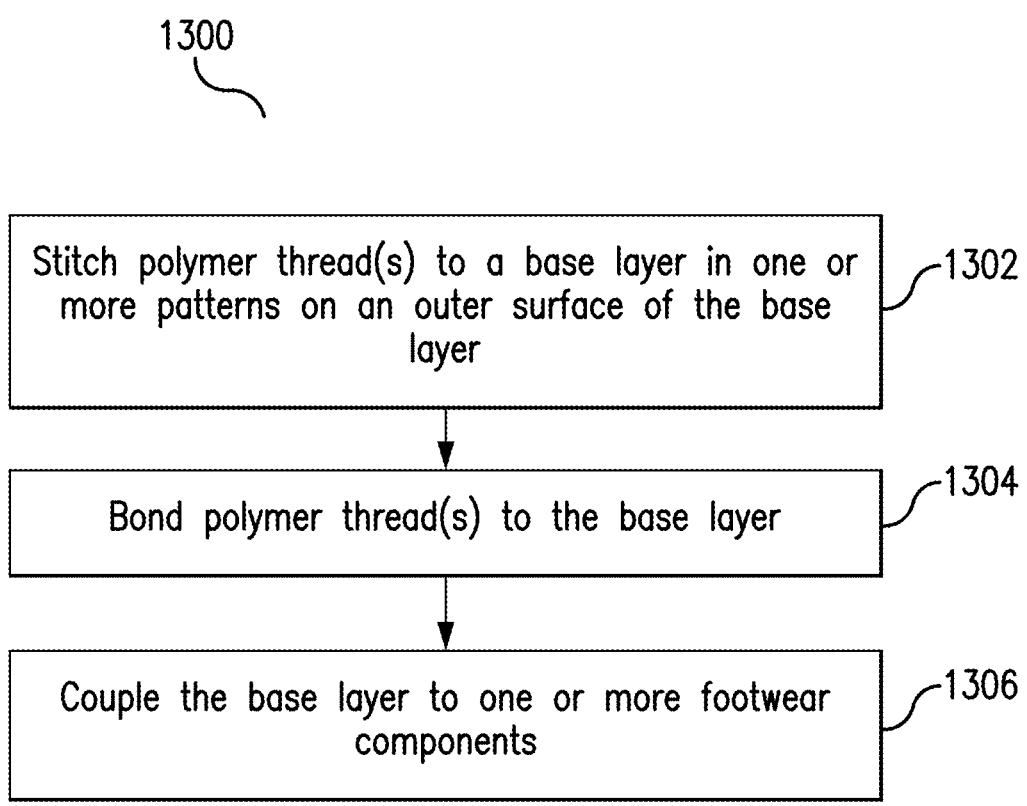

FIG. 13 is a method of making an article of footwear according to some embodiments.

Figure 14:
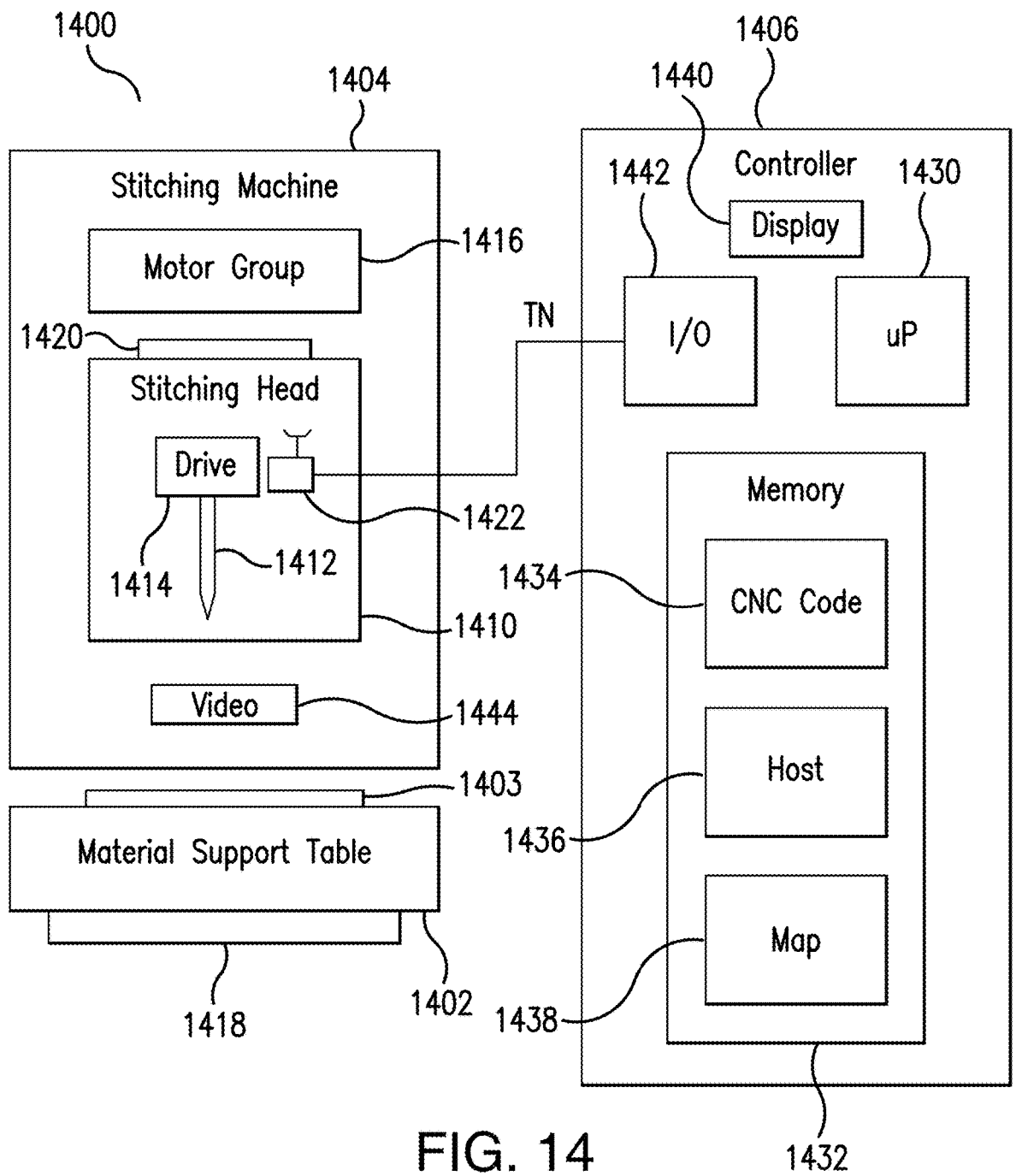

FIG. 14 is block diagram of an automated stitching machine according to some embodiments.

Figure 15:
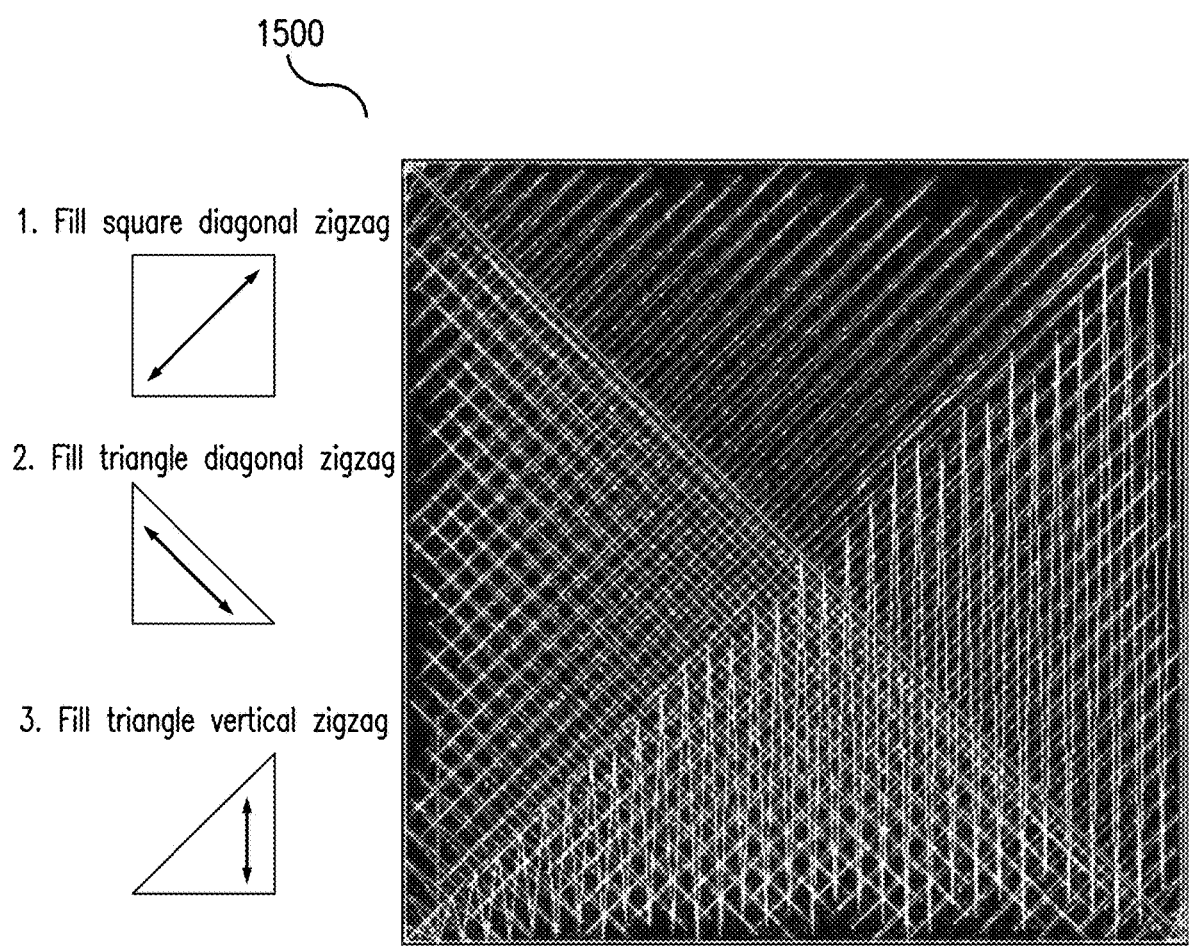

FIG. 15 is a graphical representation of stitch patterns for polymer thread sets according to some embodiments.

Figure 16:
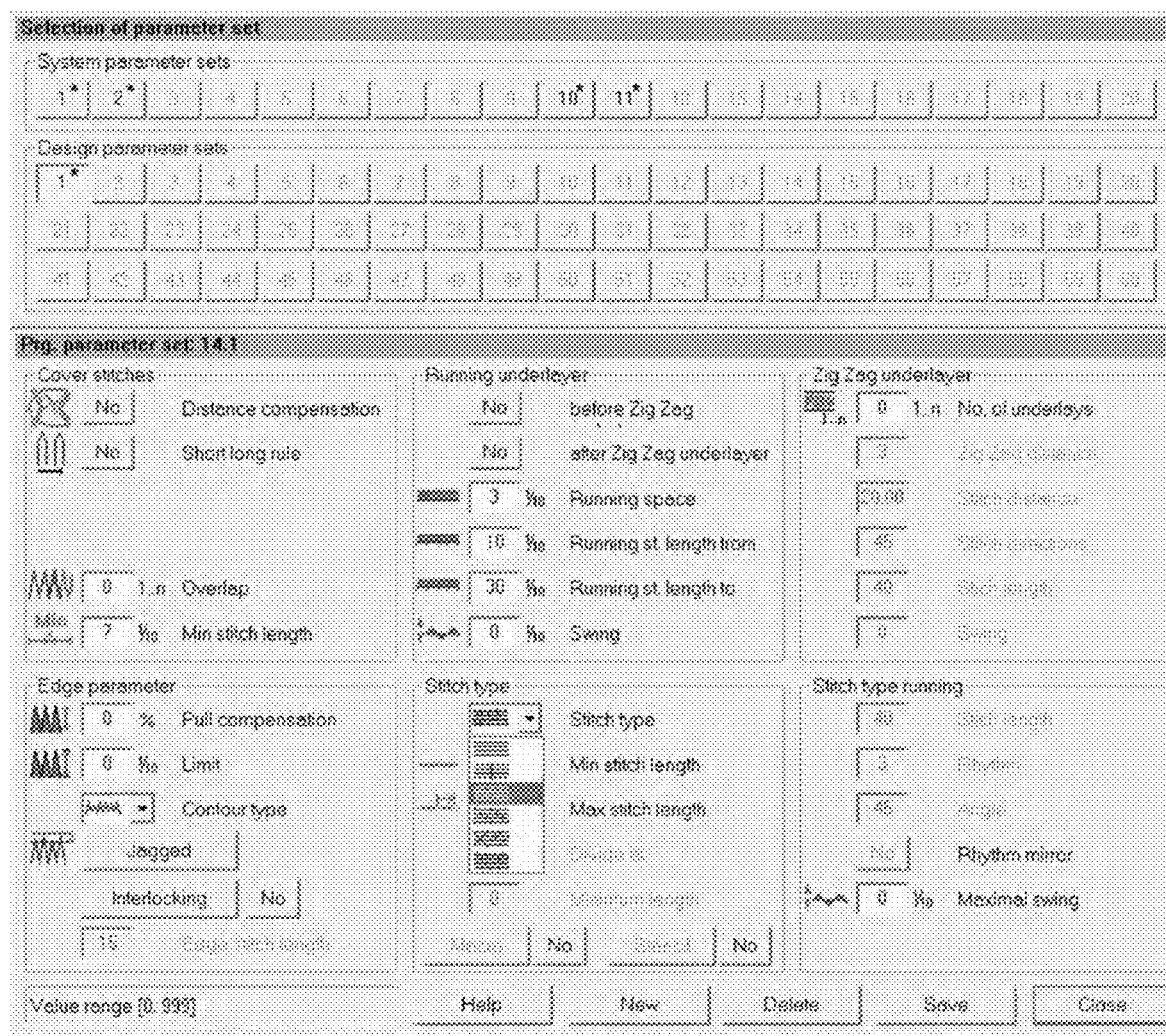

FIG. 16 is a graphical user interface for adjusting parameters of stitch pattern(s) for polymer thread set(s) according to some embodiments.

Figure 17:
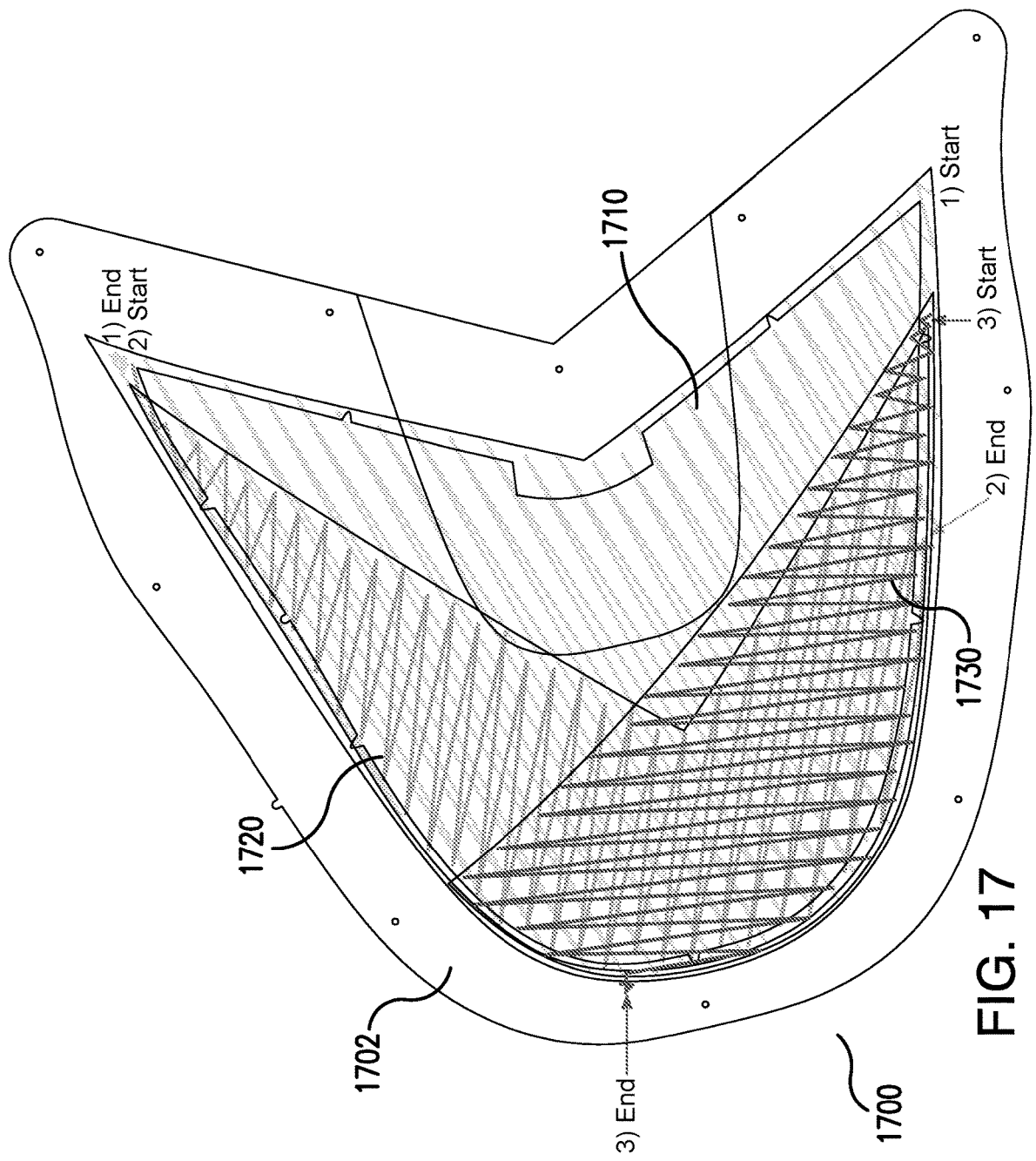

FIG. 17 is a schematic of polymer thread sets stitched in various patterns according to some embodiments.

Figure 18:
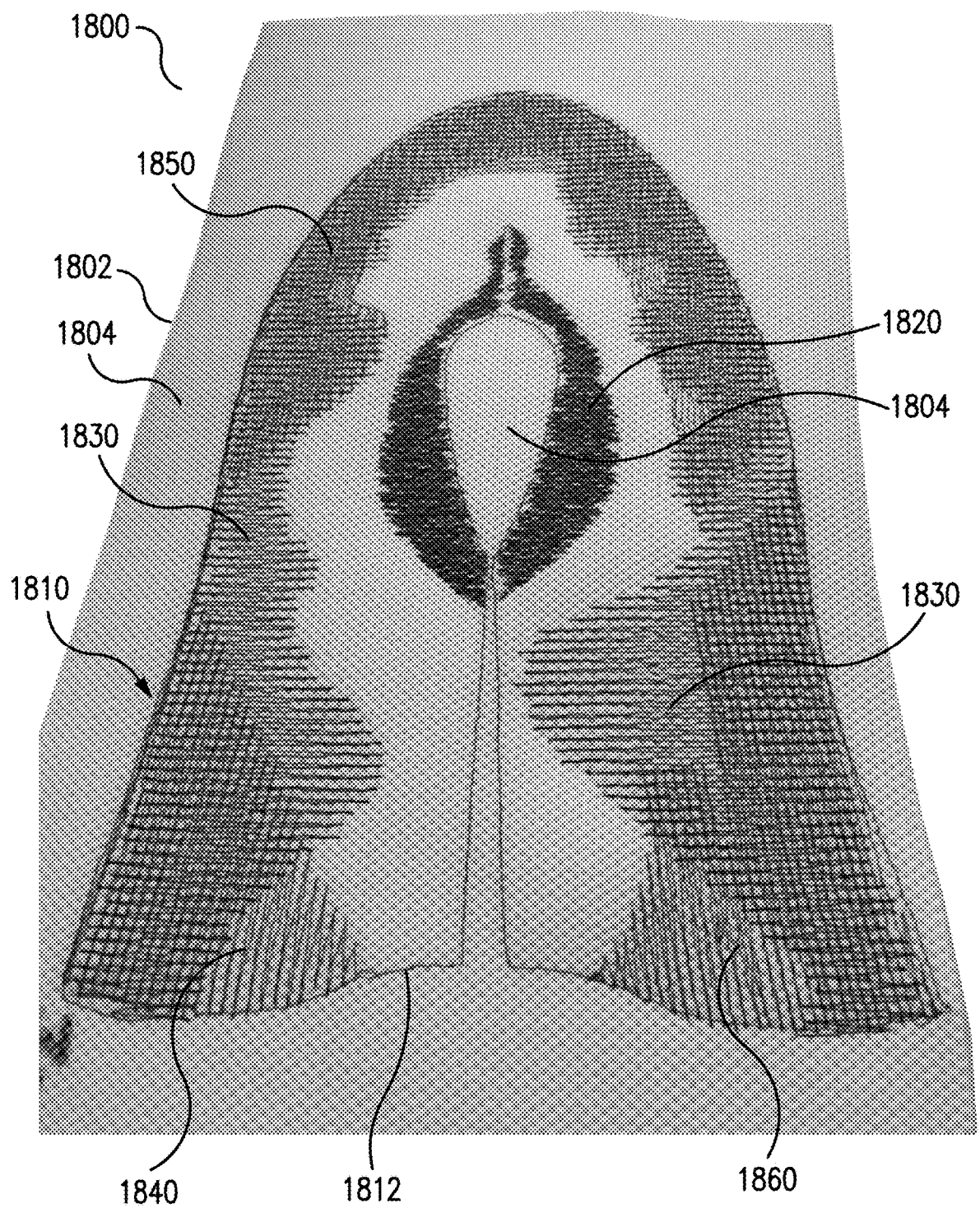

FIG. 18 is an exemplary patterned material with polymer threads stitched on a surface of a base layer in various patterns according to some embodiments.

Figure 19:
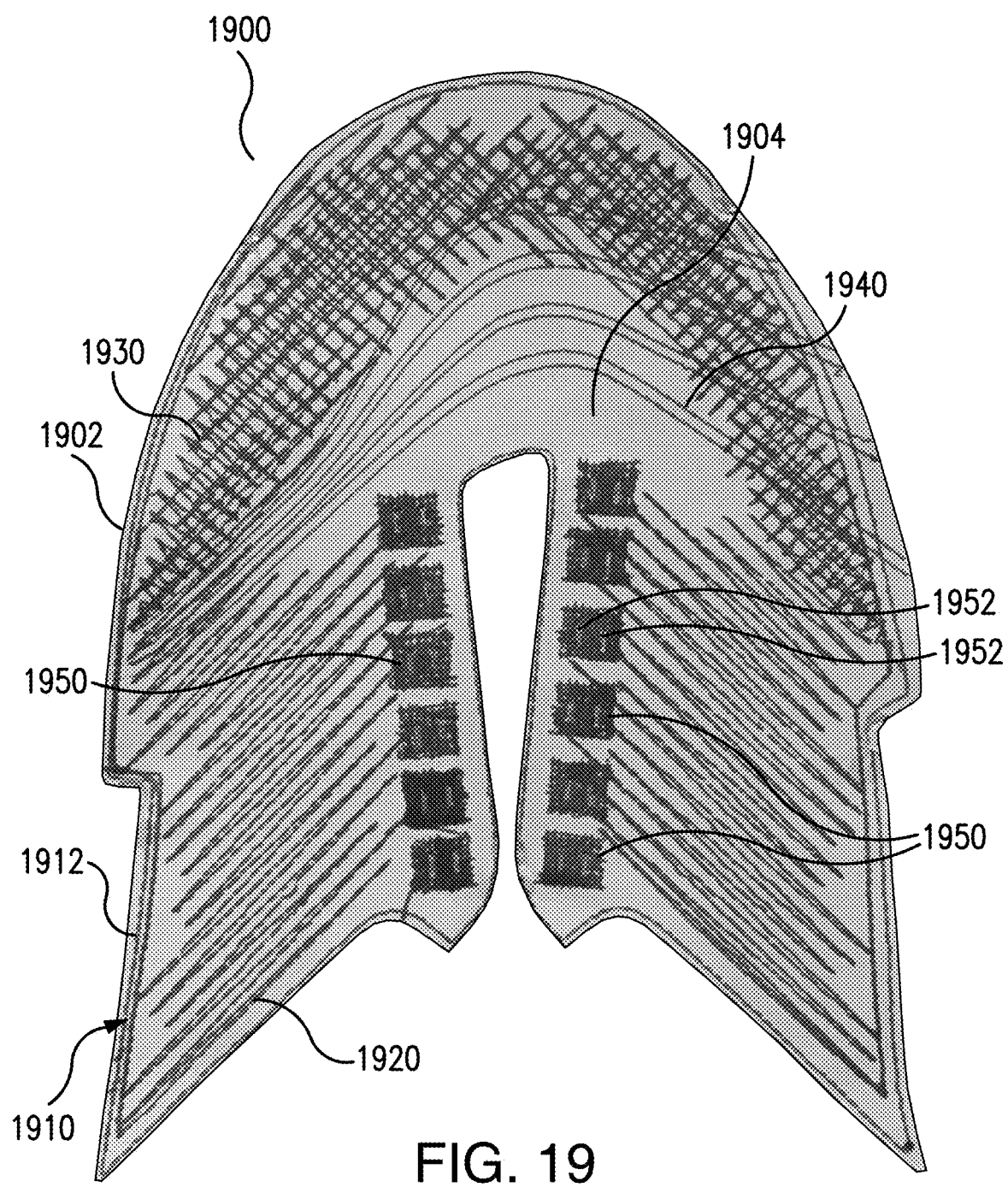

FIG. 19 is an exemplary patterned material with polymer threads stitched on a surface of a base layer in various patterns according to some embodiments.

Figure 20:
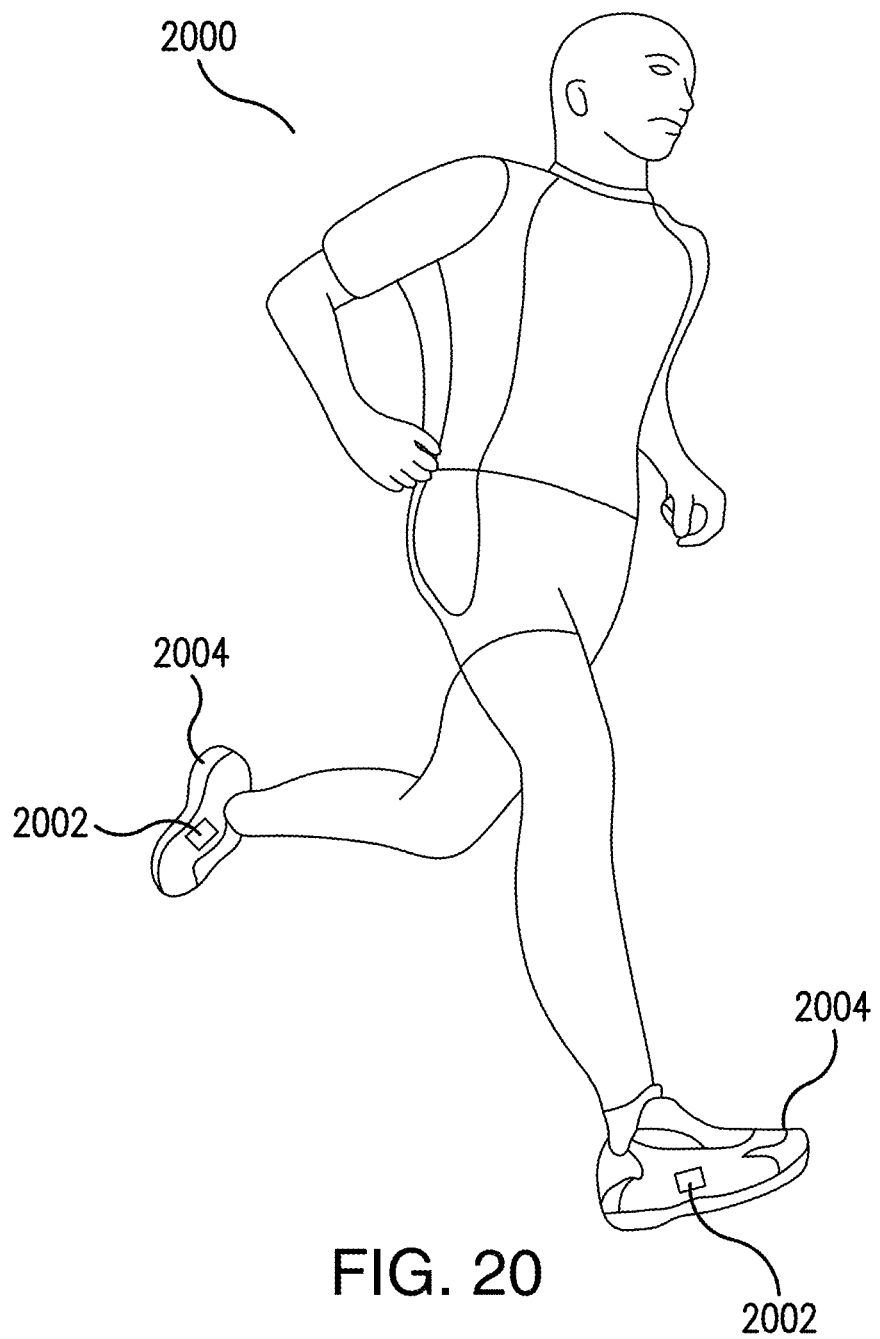

FIG. 20 is an illustration of an individual with sensor modules coupled to articles of footwear.

Figure 21A:
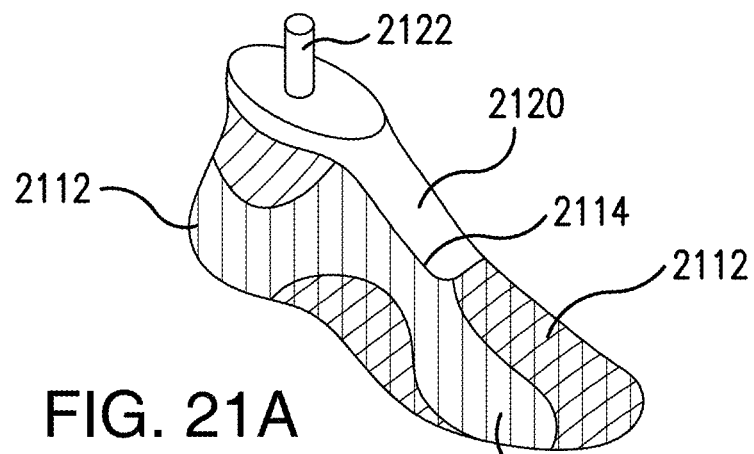
Figure 21B:
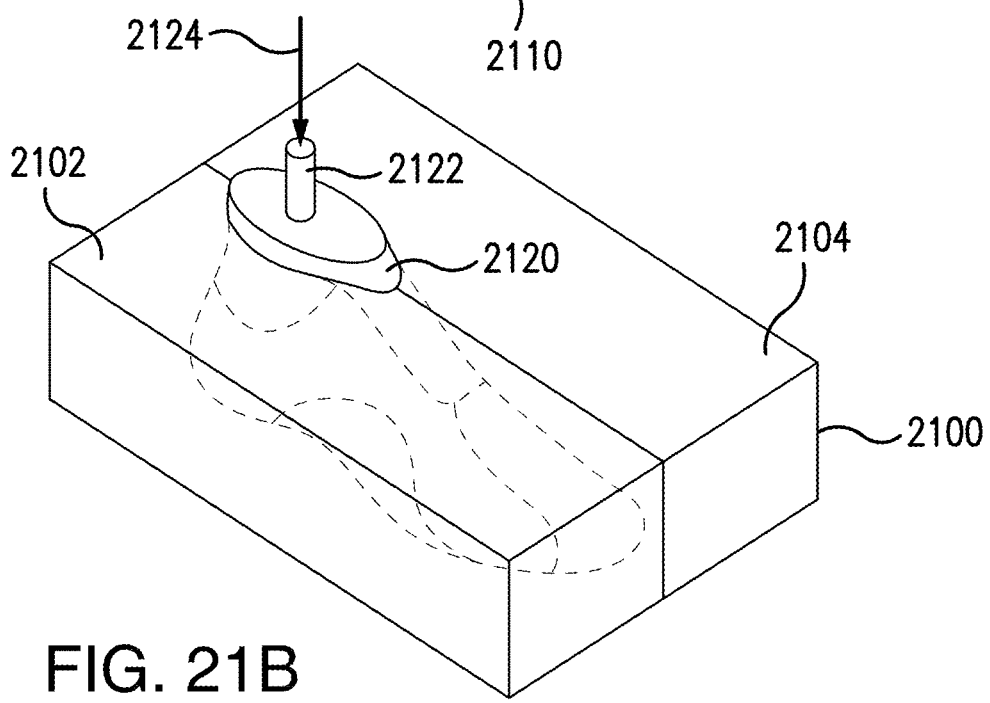
Figure 21C:
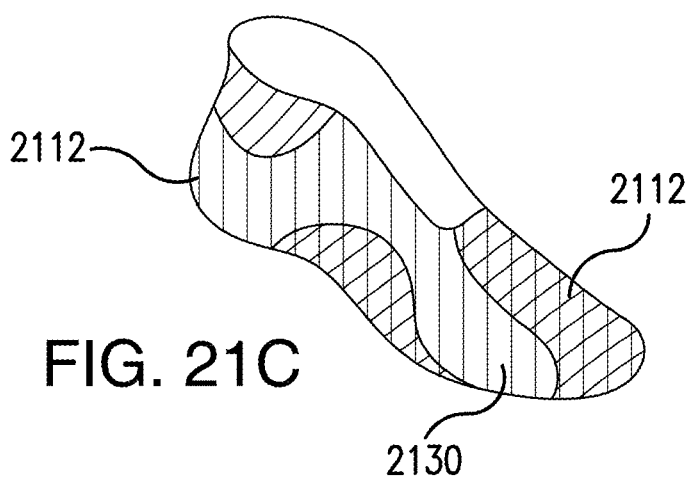

FIGS. 21A-21C show an exemplary process for three-dimensionally thermo-molding an upper according to an embodiment.

Figure 22:
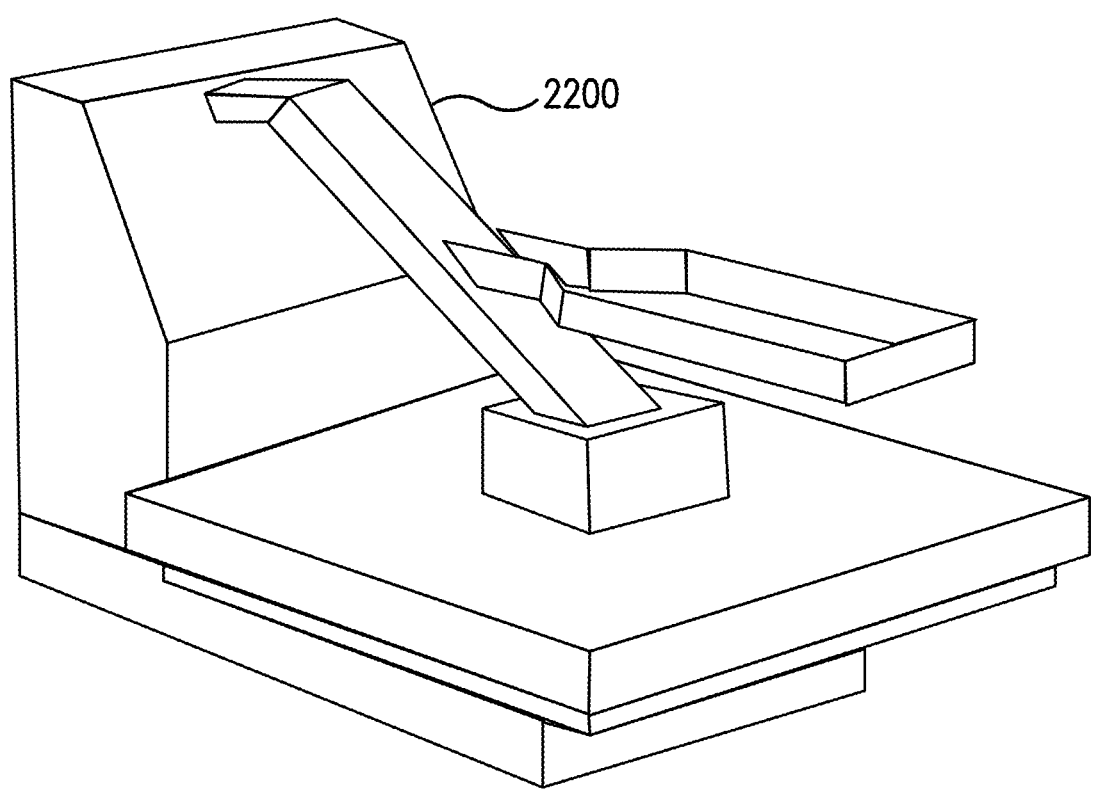

FIG. 22 is a heat press according to some embodiments.

Figure 23A:
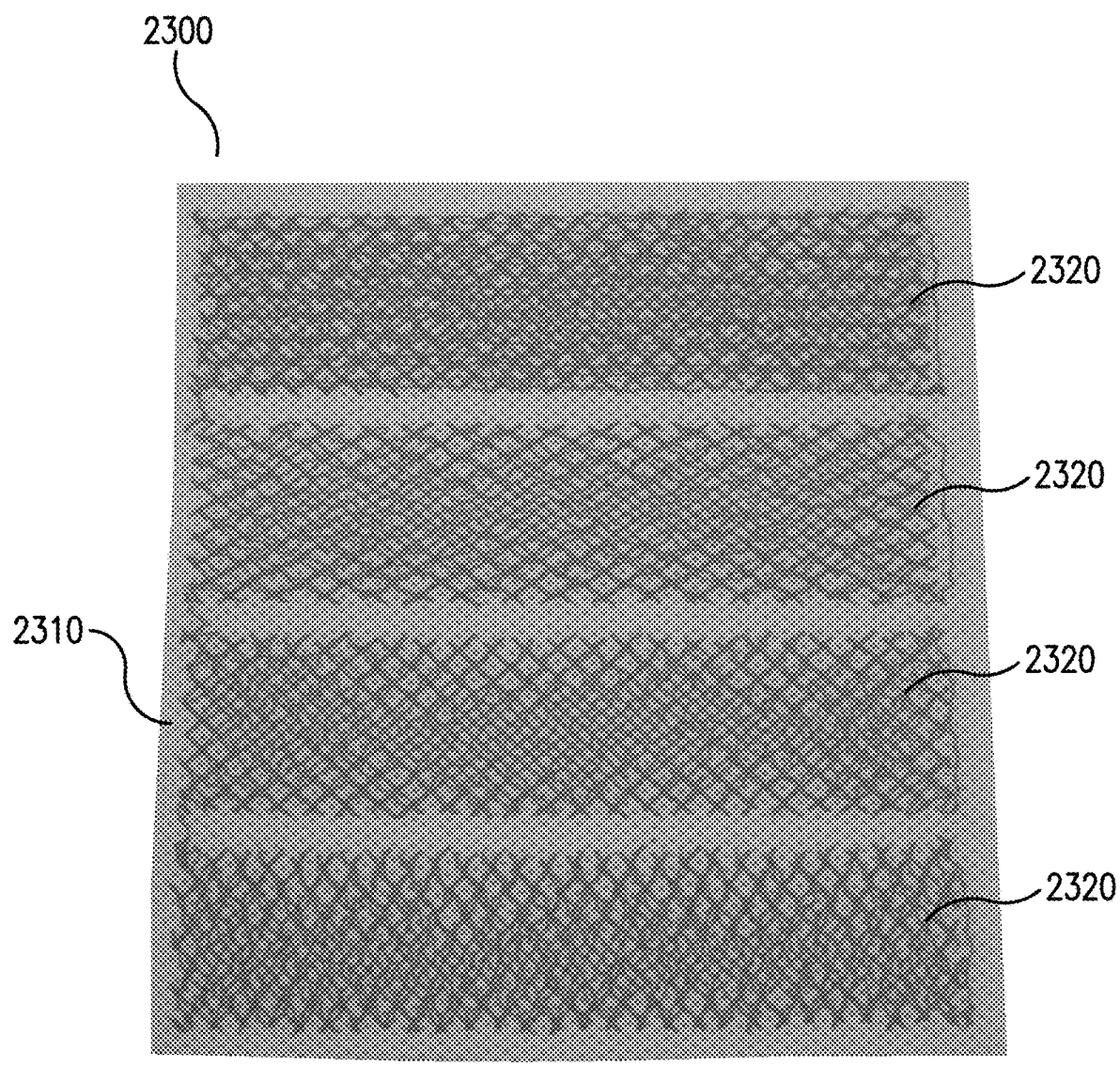
Figure 23B:
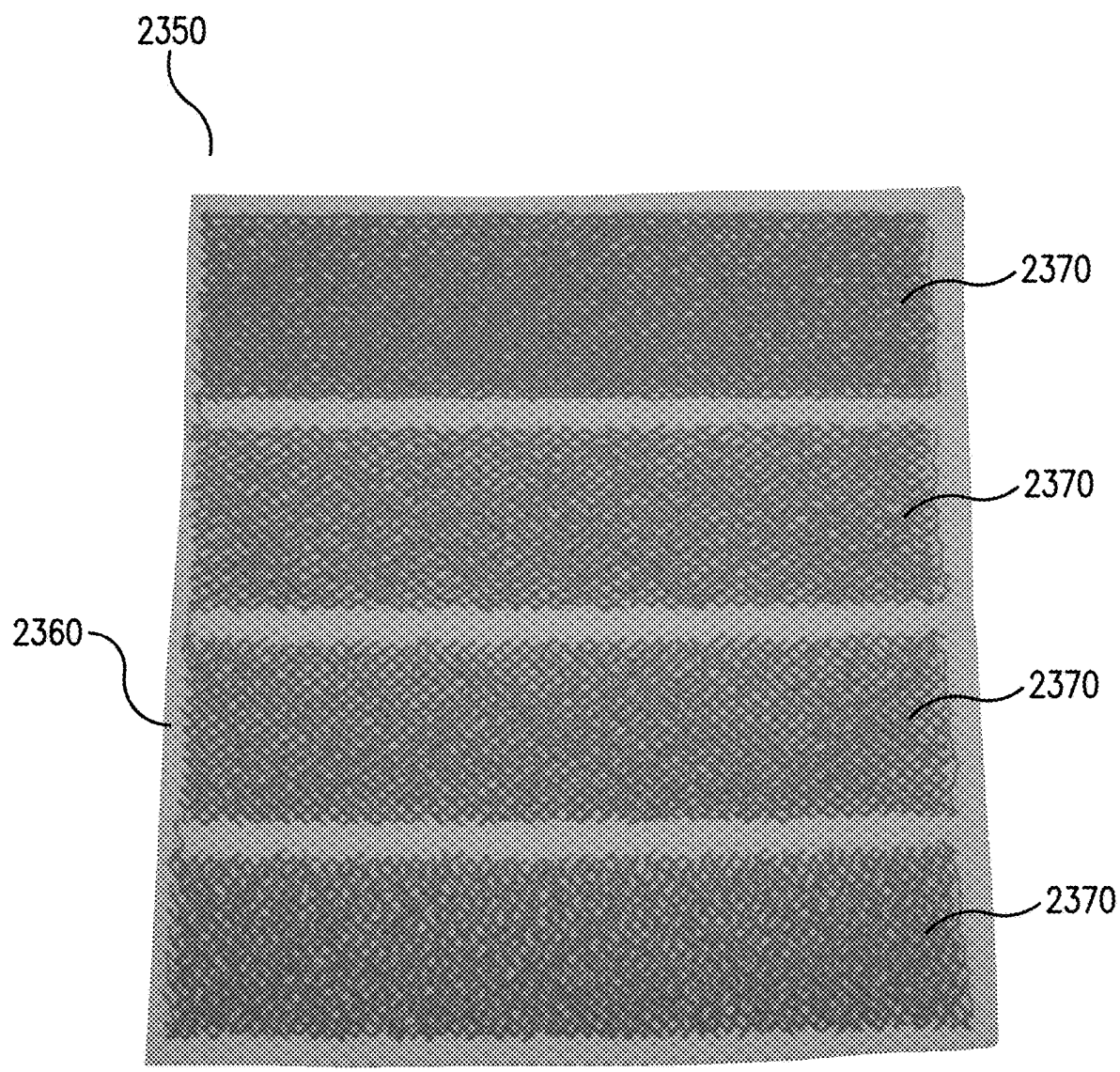

FIGS. 23A and 23B show base materials with various polymer thread patterns according to various embodiments.

Figure 24B:
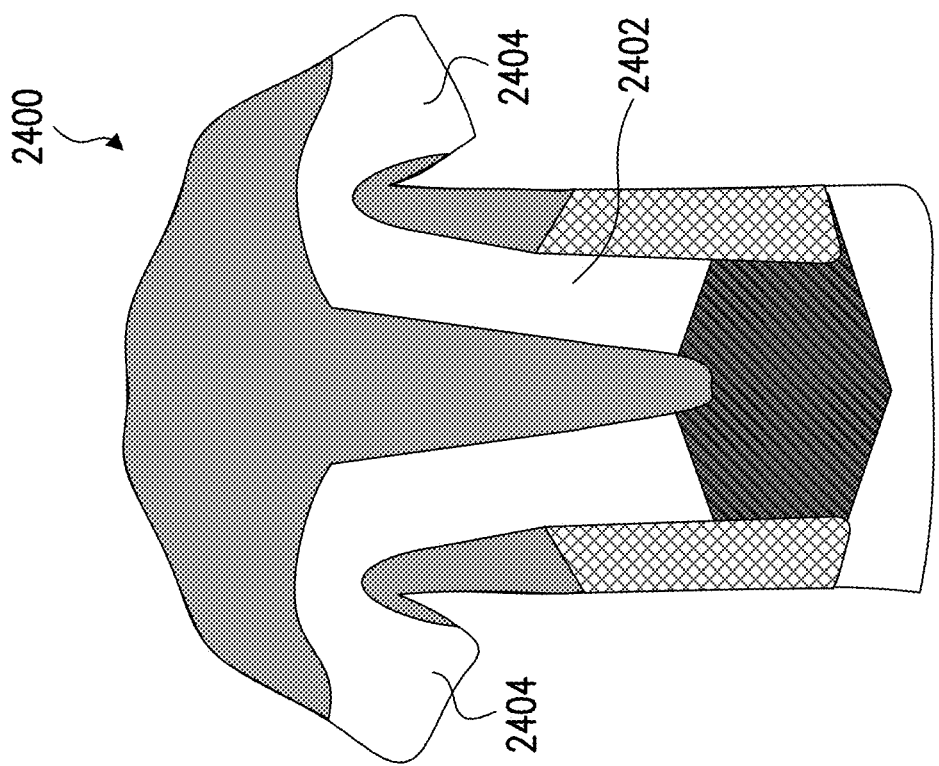
Figure 24A:
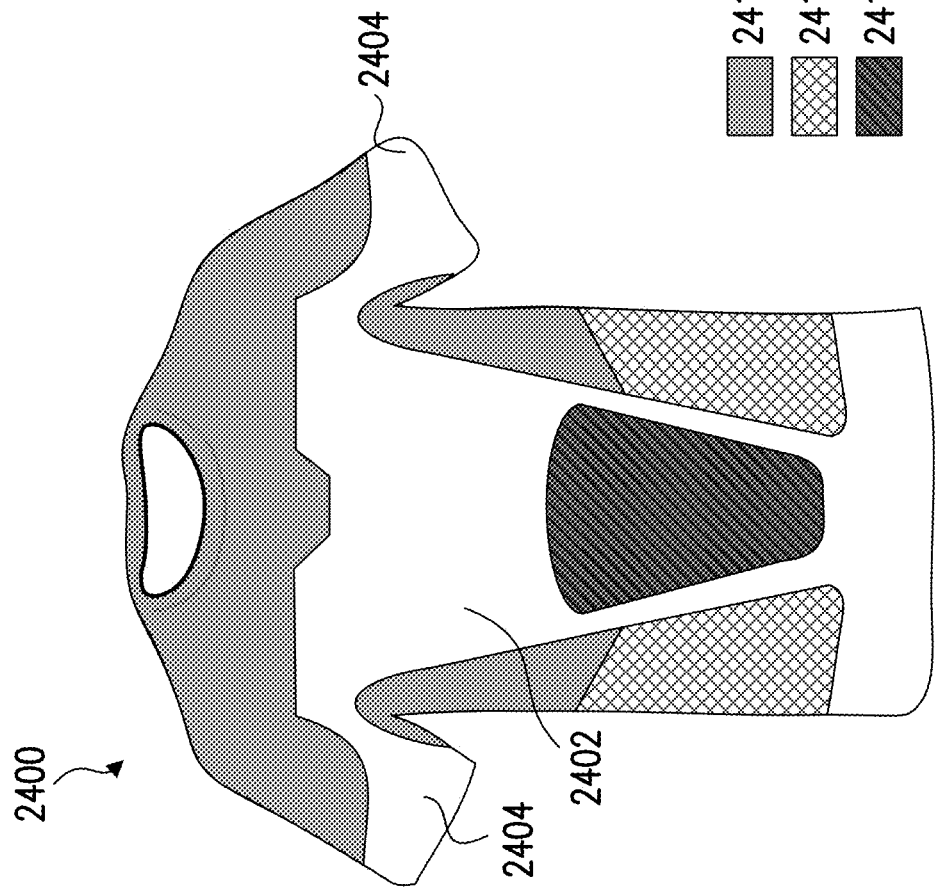

FIGS. 24A and 24B show an article of apparel according to some embodiments.

Figure 25:
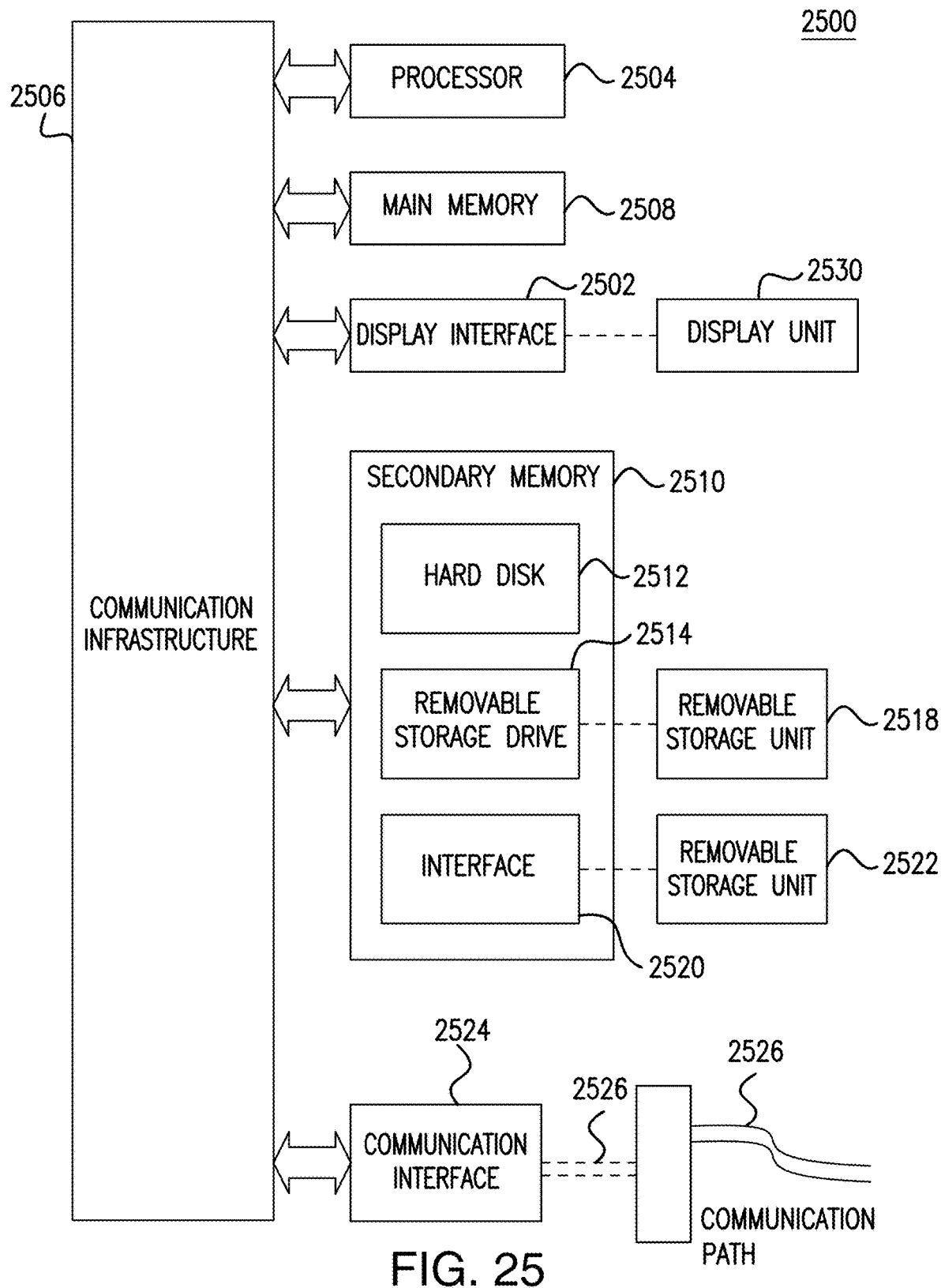

FIG. 25 is a schematic block diagram of an exemplary computer system in which embodiments may be implemented.

DETAILED DESCRIPTION OF THE INVENTION

The present invention(s) will now be described in detail with reference to embodiments thereof as illustrated in the accompanying drawings. References to "one embodiment", "an embodiment", "an exemplary embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

An article of footwear has many purposes. Among other things, an article of footwear may serve to provide cushioning for a wearer's foot, support a wearer's foot, and protect a wearer's foot. Each of these purposes, alone or in combination, provides for a comfortable article of footwear suitable for use in a variety of scenarios (e.g., exercise and every day activities). The features of an article of footwear (e.g., shape and materials used to make footwear) may be altered to produce desired characteristics, for example, support, stability, durability, weight, propulsion, and/or breathability.

Durable footwear will properly function for an extended period of time and may instill a wearer's trust in specific manufacture's footwear, leading to repeat sales. Lightweight footwear may be conformable for an individual and, for individuals competing in an athletic activity, such as running or biking, may provide a completive edge due to the decreased weight the individual carries on his or her foot. Breathable footwear may increase comfort for an individual by wicking sweet and heat away from an individual's foot.

Supportive/stable footwear may protect an individual's foot from injury. Propulsion provided by an article of footwear may optimize the performance of a wearer's foot by, for example, maximizing the energy transfer from the individual's foot to the surface his or her foot is in contact with (e.g., the ground), via the article of footwear. Maximizing the energy transfer between the individual's foot and a surface (i.e., reducing energy lost via and/or absorbed by an article of footwear) may help an athlete, for example, accelerate faster, maintain a higher maximum speed, change directions faster, and jump higher. Designing footwear having a high degree of one or more of these characteristics without detrimentally affecting other characteristics of the footwear may be desirable.

An article of footwear, or a portion thereof (e.g., an upper), may be configured to provide various degrees of durability, weight, breathability, support, propulsion, etc. But the cost of manufacturing the article of footwear may also be a consideration. Footwear, or a portion thereof, that may be manufactured at a relatively low cost may be desirable for manufactures and consumers. Footwear that can be manufactured using a relatively small amount of resources (e.g., energy and man power), materials, and time reduces manufacturing costs and may also reduce the environmental impact of manufacturing.

In some embodiments, articles of footwear discussed herein may include one or more polymer thread sets patterned on the upper of the article of footwear. The polymer thread set(s) may be stitched in one or more patterns on a base material/layer of the upper. Stitching polymer thread set(s) on a base material of the upper may preserve the intrinsic characteristics of the base material (e.g., breathability and weight) while also providing localized targeted characteristics to areas of the base material, and thus targeted characteristics to areas on an upper. Targeted characteristics may be characteristics provided in specific areas on an upper to meet desired needs for the specific areas (e.g., strength, stretchability, and/or breathability needs). In some embodiments, the targeted characteristics may be directional characteristics (e.g., directional strength or directional stretchability). Directional strength and/or directional stretchability may provide targeted degrees of support, stability, and/or propulsion to different areas on the upper. In some embodiments, the targeted characteristics may be non-directional characteristics, such as abrasion resistance, tackiness, breathability, or insulating characteristics.

In some embodiments, individual polymer thread sets patterned on a base material may be oriented in different directions. The different orientations of the polymer thread sets may provide targeted characteristics (e.g., directional characteristics) to areas on an upper. In some embodiments, the spacing between thread lines in different thread sets may be tailored to provide targeted characteristics to areas on an upper.

In some embodiments, one or more polymer thread sets may overlap on area(s) of a base material on an upper. The overlap between polymer thread sets may provide targeted characteristics to area(s) on the base material, and therefore the upper. In areas of overlap between one or more polymer thread sets, a composite characteristic resulting from the characteristic(s) (e.g., directional characteristic(s)) of individual overlapping polymer thread sets may be provided.

In some embodiments, the polymer thread set(s) may be stitched on a base material of an upper to produce patterned polymer thread sets on a surface of the base material. In some embodiments, the polymer thread set(s) may be embroidered on the base material. In some embodiments, the polymer thread set(s) may be stitched to the base material using a computer numerically controlled (CNC) stitching machine. Stitching polymer thread set(s) may produce patterns on a surface of the base material while also integrating the polymer thread set(s) into the base material.

In some embodiments, polymer thread set(s) may be bonded to a base material for an upper via a polymeric material of the polymer thread sets. In other words, the polymer thread set(s) may be directly bonded to a base material. In some embodiments, polymer thread(s) in a polymer thread set may be a composite thread including a core material and a coating material. In some embodiments, the coating material may bond the polymer thread(s) in a polymer thread set to a base layer when the coating material is heated and subsequently cooled. In some embodiments, the coating material may be a thermoplastic material. In some embodiments, the coating material may have a melting temperature less than the melting temperature of the core material. In some embodiments, the coating material may be heated to a temperature less than its melting point when bonding polymer thread(s) to a base layer. Bonding at least a portion of one or more polymer thread sets to the base material (e.g., via the application of heat and/or pressure) after stitching the polymer thread set(s) may further secure the polymer thread set(s) to the base material and further integrate the polymer thread set(s) into the base material.

In some embodiments, one or more polymer thread sets may be bonded (e.g., fused) together in area(s) of overlap between polymer thread sets. In such embodiments, polymer thread(s) in different polymer thread sets may be fused together via polymeric material(s) of the polymer thread sets. For example, a coating material of the polymer thread sets may fuse the polymer thread(s) together after heating the coating material to a predetermined temperature and subsequently cooling the coating material. In some embodiments, the predetermined temperature may be equal to or greater than the melting point of the coating material. In some embodiments, the predetermined temperature may be less than the melting point of the coating material. Bonding polymer thread(s) together may provide targeted characteristics to areas of a base material, and therefore areas of an upper.

Stitching and direct bonding of one or more polymer thread sets on areas of a base material may provide targeted characteristics and facilitate efficient and reproducible manufacturing of an upper for an article of footwear. Stitching and bonding of polymer thread set(s) to a base material may reduce the amount of material needed to produce an upper. For example, additional layers or materials (e.g., lamination layers) may not be needed to secure polymer thread(s) to a base layer. Stitching and direct bonding of one or more polymer thread sets may also reduce the number of processes needed to produce an upper (e.g., by eliminating the need for a lamination layer process). Reducing the amount of material and/or number of processes needed to produce an upper may reduce cost and facilitate reproducibility for a manufacturing process.

Additionally, stitching and bonding of polymer thread set(s) may facilitate customization of an upper for an individual, or group of individuals. The stitching patterns, the amount of bonding between polymer thread set(s) and a base layer, and/or the amount of bonding between different polymer thread sets may be tailored for an individual, or group of individuals. Customization via tailoring stitch patterns and/or bonding may facilitate flexible and efficient manufacturing by reducing the number of changes in a manufacturing process needed to customize an upper for an individual, or group of individual. For example, in some embodiments, the stitching pattern of one or more thread sets may be the only parameter altered between uppers for different individuals, or different groups of individuals. A change in stitching patterns may alter, for example, the support, stability, propulsion, abrasion resistance, tackiness, and/or breathability characteristics for different areas on an upper as needed for an individual, or group of individuals. In some embodiments, providing tackiness in specific areas on an upper may be tailor an upper to an individual's liking. For example, some soccer players may like a soccer boot that is smooth for ease of dribbling while others may like high friction for control during hard strikes.

In some embodiments, the stitching patterns and/or amount of polymer thread set bonding may be based on a biometric data profile for an individual, or group of individuals. In some embodiments, the orientation of stitching patterns for polymer thread set(s) may be based on a biometric data profile for an individual, or group of individuals. In some embodiments, the spacing between thread lines in a stitching pattern for polymer thread set(s) may be based on a biometric data profile for an individual, or group of individuals. In some embodiments, the amount of overlap between different polymer thread sets may be based on a biometric data profile for an individual, or group of individuals. Tailoring the patterns, orientation, spacing, and/or bonding of polymer thread set(s) may provide an upper with desired support, stability, durability, weight, propulsion, abrasion resistance, tackiness, and/or breathability for an individual, or group of individuals.

Figure 1:
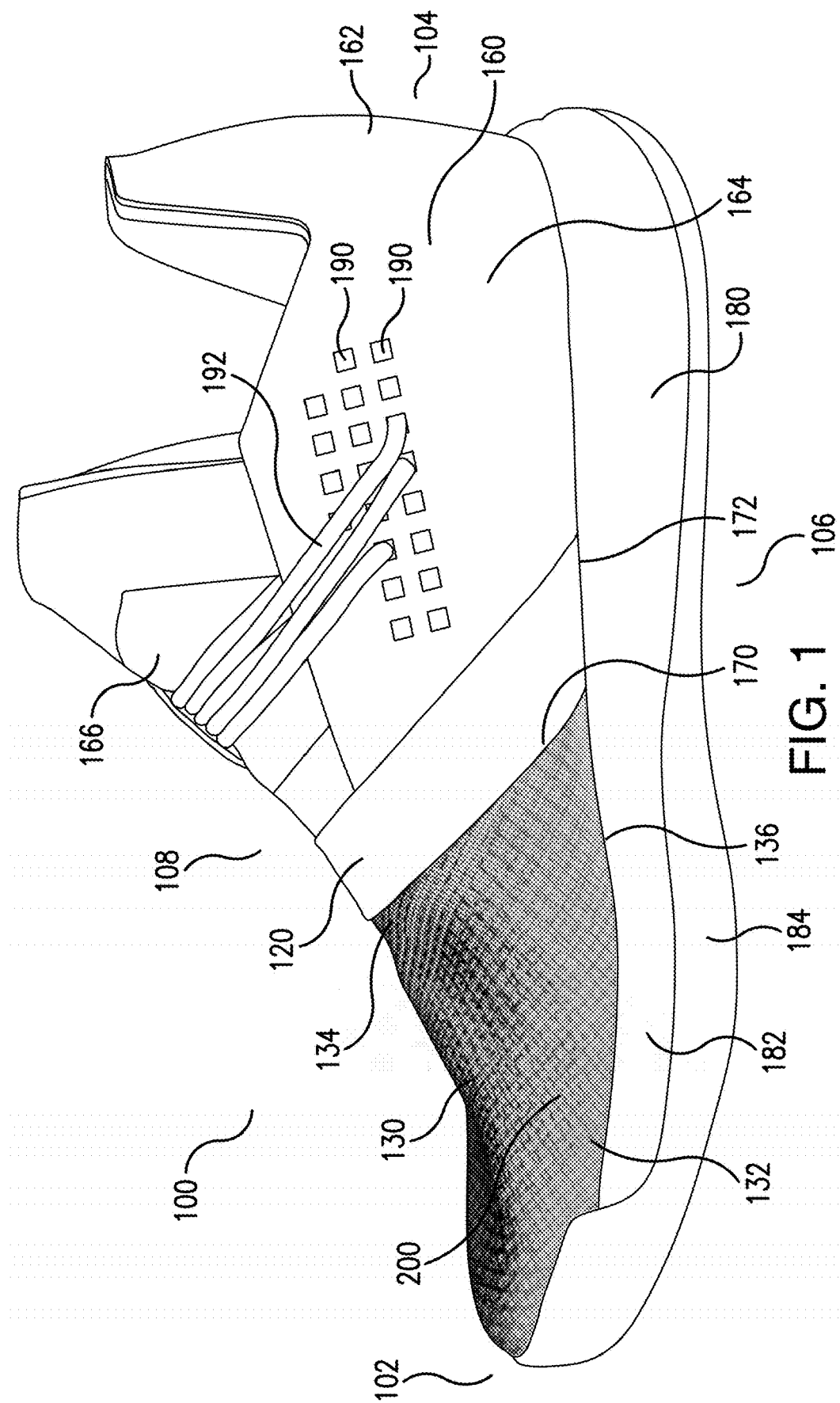
FIG. 1 is a medial side view of an article of footwear according to some embodiments.
Figure 2:
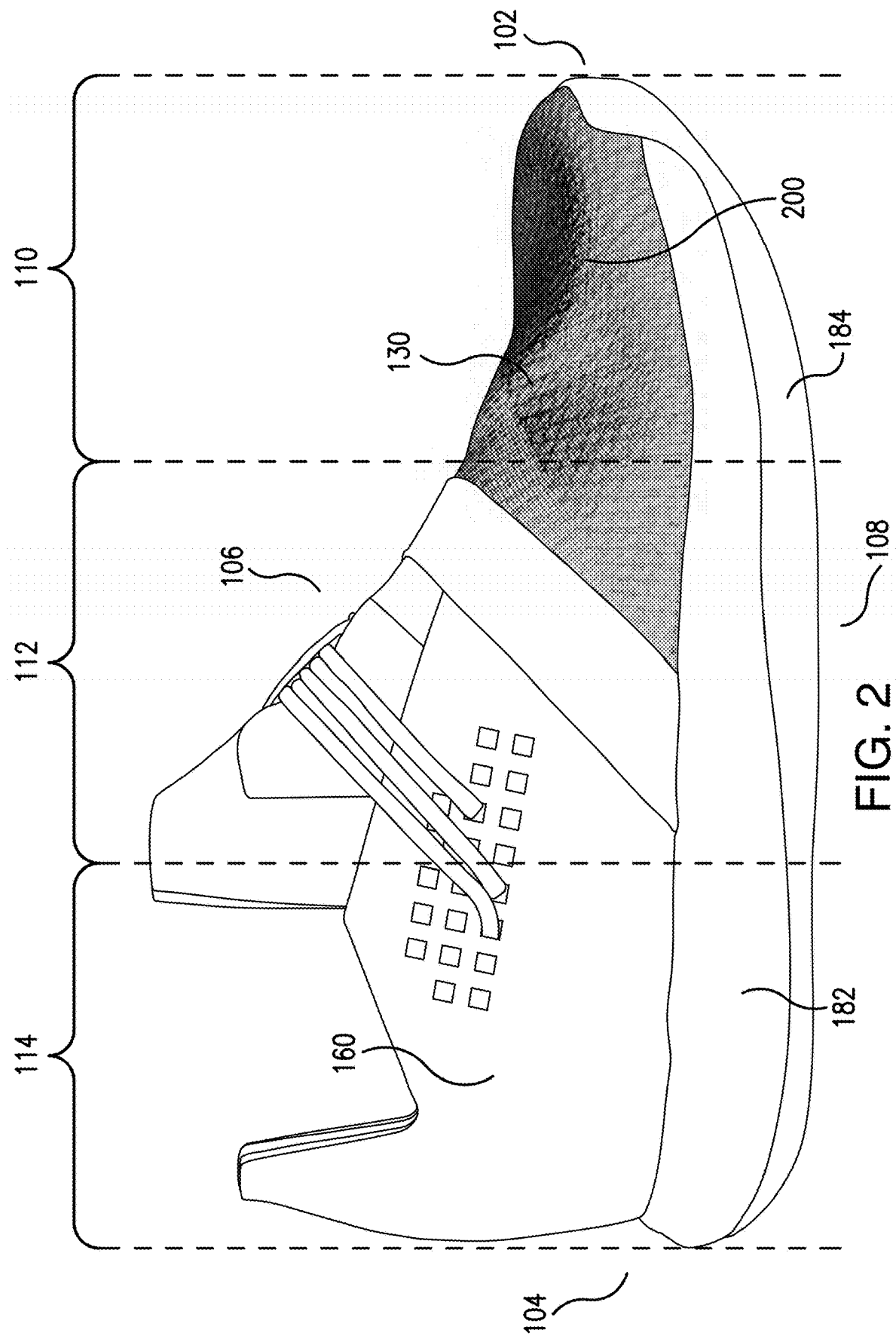
FIG. 2 is a lateral side view of an article of footwear according to some embodiments.

FIGS. 1-5 show an article of footwear 100 according to some embodiments. Article of footwear 100 may include an upper 120 coupled to a sole 180. As shown in FIG. 1, article of footwear 100 includes a forefoot end 102, a heel end 104, a medial side 106, and a lateral side 108 opposite medial side 106. As illustrated in FIG. 2, article of footwear 100 includes a forefoot portion 110, a midfoot portion 112, and a heel portion 114. Portions 110, 112, and 114 are not intended to demarcate precise areas of article of footwear 100. Rather, portions 110, 112, and 114 are intended to represent general areas of article of footwear 100 that provide a frame of reference. Although portions 110, 112, and 114 apply generally to article of footwear 100, references to portions 110, 112, and 114 also may apply specifically to upper 120 or sole 180, or individual components of upper 120 or sole 180. When article of footwear 100 is assembled, upper 120 may be coupled to sole 180.

Upper 120 may include a first portion 130 and a second portion 160. In some embodiments, first portion 130 may extend from forefoot end 102 to midfoot portion 112 of article of footwear 100. In some embodiments, first portion 130 may extend from forefoot end 102 to heel portion 114 of article of footwear 100. First portion 130 may be coupled to sole 180. In some embodiments, first portion 130 may be coupled to sole 180 along at least a portion of a border 132 of first portion 130 at a sole connection area 136. First portion 130 may be coupled to sole 180 via for example, but not limited to, adhesive bonding, stitching, lamination (e.g., high frequency welding or heat welding), or a combination thereof. First portion 130 may be coupled to second portion 160. In some embodiments, first portion 130 may be coupled to second portion 160 along at least a portion of border 132 at an upper connection area 134. First portion 130 may be coupled to second portion 160 via for example, but not limited to, adhesive bonding, stitching, lamination (e.g., high frequency welding or heat welding), or a combination thereof.

In some embodiments, second portion 160 may extend from heel end 104 to forefoot portion 110 of article of footwear 100. In some embodiments, second portion 160 may be padded (i.e., cushioned) to provide comfort. In some embodiments, second portion 160 may include a heel counter 162, an ankle cuff 164, and a tongue 166. Second portion 160 may be coupled to sole 180. In some embodiments, second portion 160 may be coupled to sole 180 along at least a portion of a border 170 of second portion 160 at a sole connection area 172. In some embodiments, second portion 160 may be coupled to sole 180 at locations other than or in addition to sole connection area 172. Second portion 160 may be coupled to sole 180 via for example, but not limited to, adhesive bonding, stitching, lamination (e.g., high frequency welding or heat welding), or a combination thereof. In some embodiments, second portion 160 may be coupled to first portion 130 along at least a portion of border 170 at upper connection area 134 via for example, but not limited to, adhesive bonding, stitching, lamination (e.g., high frequency welding or heat welding), or a combination thereof. In some embodiments, second portion 160 may be composed of a different material, or different combination of materials, than first portion 130. In some embodiments, second portion 160 may comprise neoprene. In some embodiments, heel counter 162 may comprise neoprene.

Upper 120 may also include one or more eyelets 190 for securing and tensioning a shoe lace 192. In some embodiments, eyelets 190 may be integrally formed in first portion 130 and/or second portion 160. In some embodiments, eyelets 190 may be separate components coupled to first portion 130 and/or second portion 160, via for example stitching or an adhesive.

In some embodiments, sole 180 may include a midsole 182 coupled to an outsole 184. Upper 120 and sole 180 may be configured for a specific type of footwear, including, but not limited to, a running shoe, a hiking shoe, a water shoe, a training shoe, a fitness shoe, a dancing shoe, a biking shoe, a tennis shoe, a cleat (e.g., a baseball cleat, a soccer cleat, or a football cleat), a basketball shoe, a boot, a walking shoe, a casual shoe, or a dress shoe. Moreover, sole 180 may be sized and shaped to provide a desired combination of cushioning, stability, and ride characteristics to article of footwear 100. The term "ride" may be used herein in describing some embodiments as an indication of the sense of smoothness or flow occurring during a gait cycle including heel strike, midfoot stance, toe off, and the transitions between these stages. In some embodiments, sole 180 may provide particular ride features including, but not limited to, appropriate control of pronation and supination, support of natural movement, support of unconstrained or less constrained movement, appropriate management of rates of change and transition, and combinations thereof.

Sole 180 and portions thereof (e.g., midsole 182 and outsole 184) may comprise material(s) for providing desired cushioning, ride, and stability. Suitable materials for sole 180 (e.g., midsole 182 and/or outsole 184) include, but are not limited to, a foam, a rubber, ethyl vinyl acetate (EVA), expanded Thermoplastic polyurethane (eTPU), Thermoplastic rubber (TPR) and a thermoplastic polyurethane (PU). In some embodiments, the foam may comprise, for example, an EVA based foam or a PU based foam and the foam may be an open-cell foam or a closed-cell foam. In some embodiments, midsole 182 and/or outsole 184 may comprise elastomers, thermoplastic elastomers (TPE), foam-like plastics, and gel-like plastics.

In some embodiments, portions of sole 180 (e.g., midsole 182 and outsole 184) may comprise different materials to provide different characteristics to different portions of sole 180. In some embodiments, midsole 182 and outsole 184 may have different hardness characteristics. In some embodiments, the material density of midsole 182 and outsole 184 may be different. In some embodiments, the moduli of the materials used to make midsole 182 and outsole 184 may be different. As a non-limiting example, the material of outsole 184 may have a higher modulus than the material of midsole 182.

Sole 180 and portions thereof (e.g., midsole 182 and outsole 184) may be formed using suitable techniques, including, but not limited to, injection molding, blow molding, compression molding, and rotational molding. In some embodiments, midsole 182 and outsole 184 may be discrete components that are formed separately and attached. In some embodiments, midsole 182 may be attached to outsole 184 via, for example, but not limited to, adhesive bonding, stitching, welding, or a combination thereof. In some embodiments, midsole 182 may be attached to outsole 184 via an adhesive disposed between midsole 182 and outsole 184.

Figure 3:
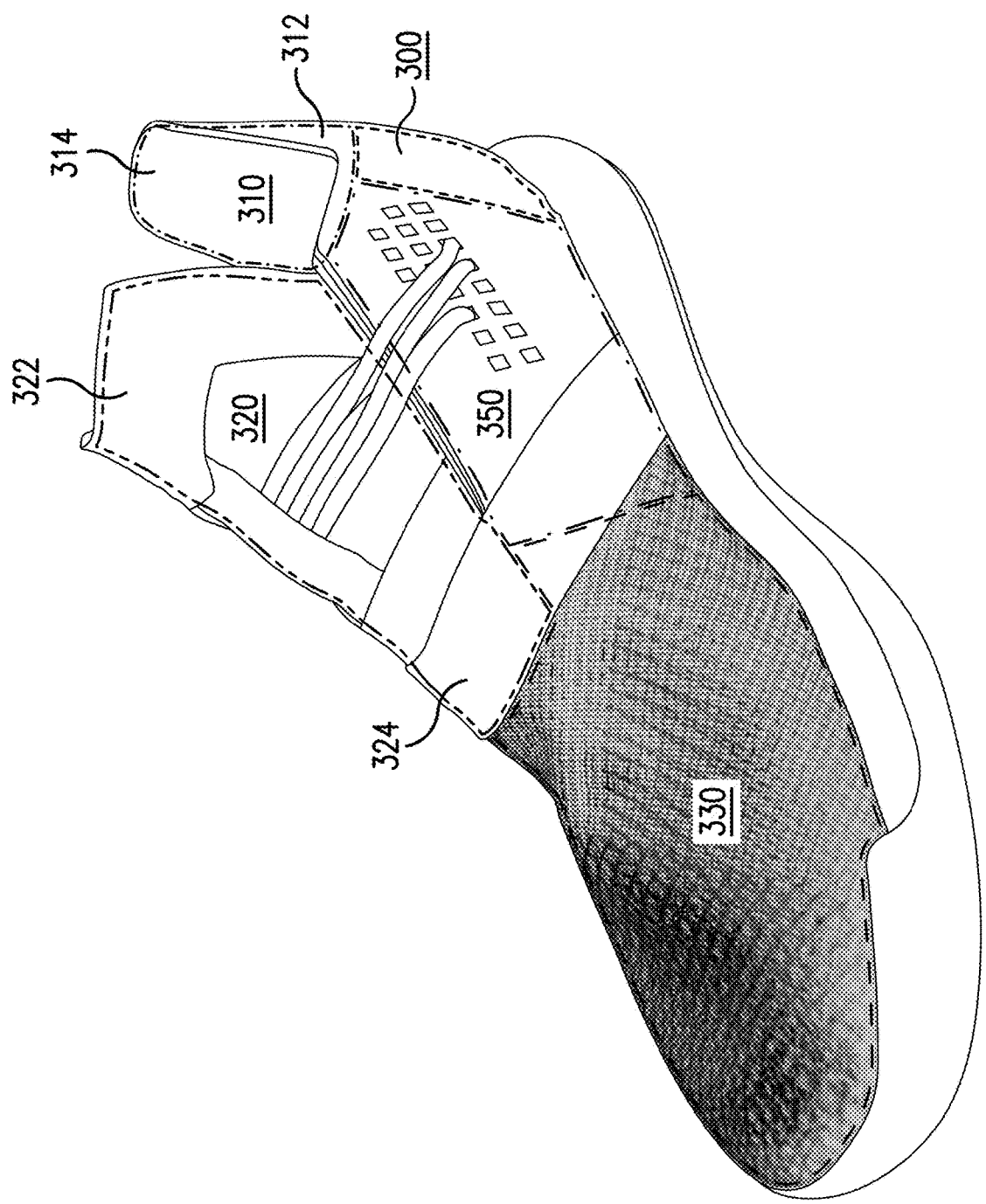
FIG. 3 is a medial perspective view of an article of footwear according to some embodiments.
Figure 4:
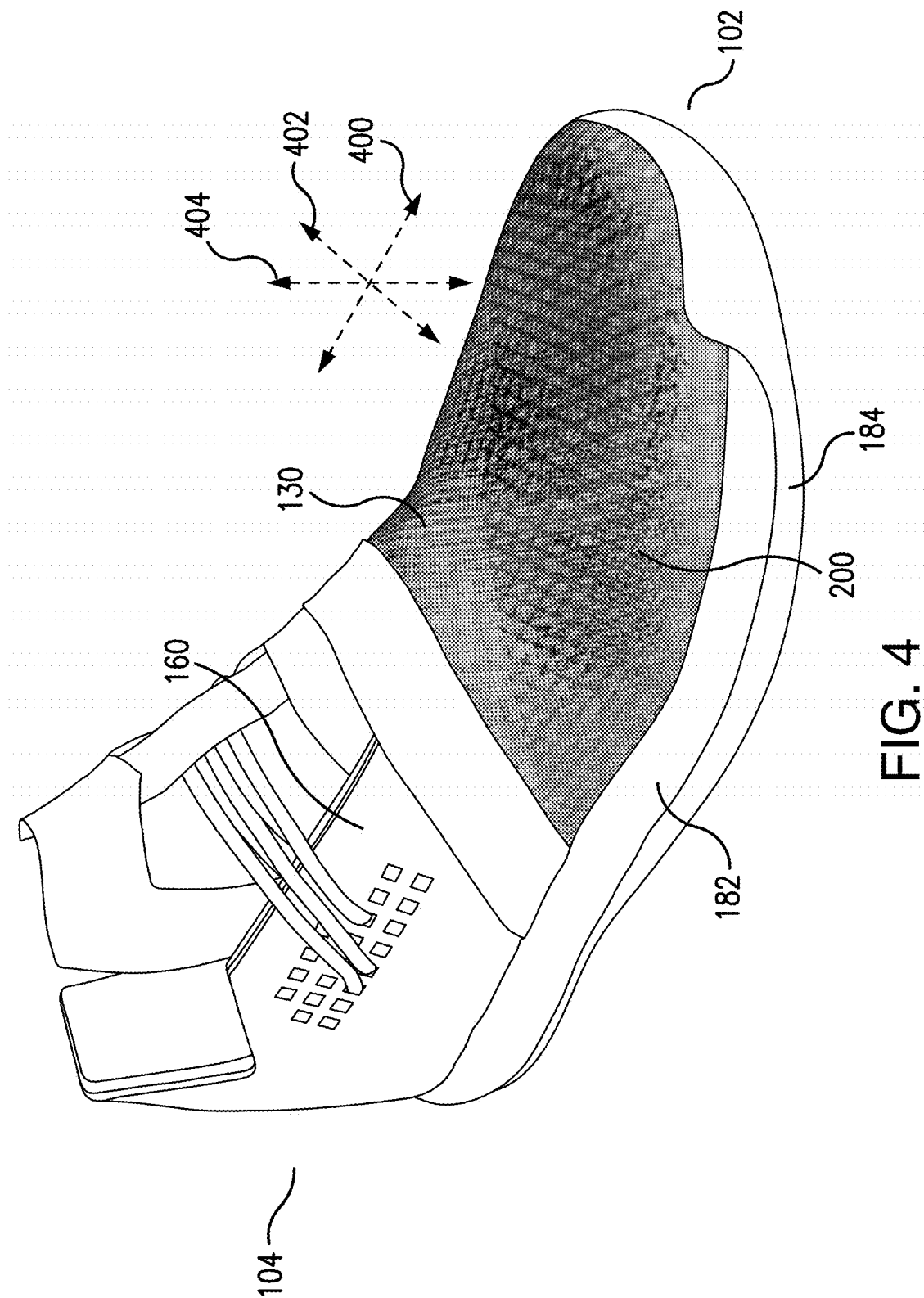
FIG. 4 is a lateral perspective view of an article of footwear according to some embodiments.
Figure 5:
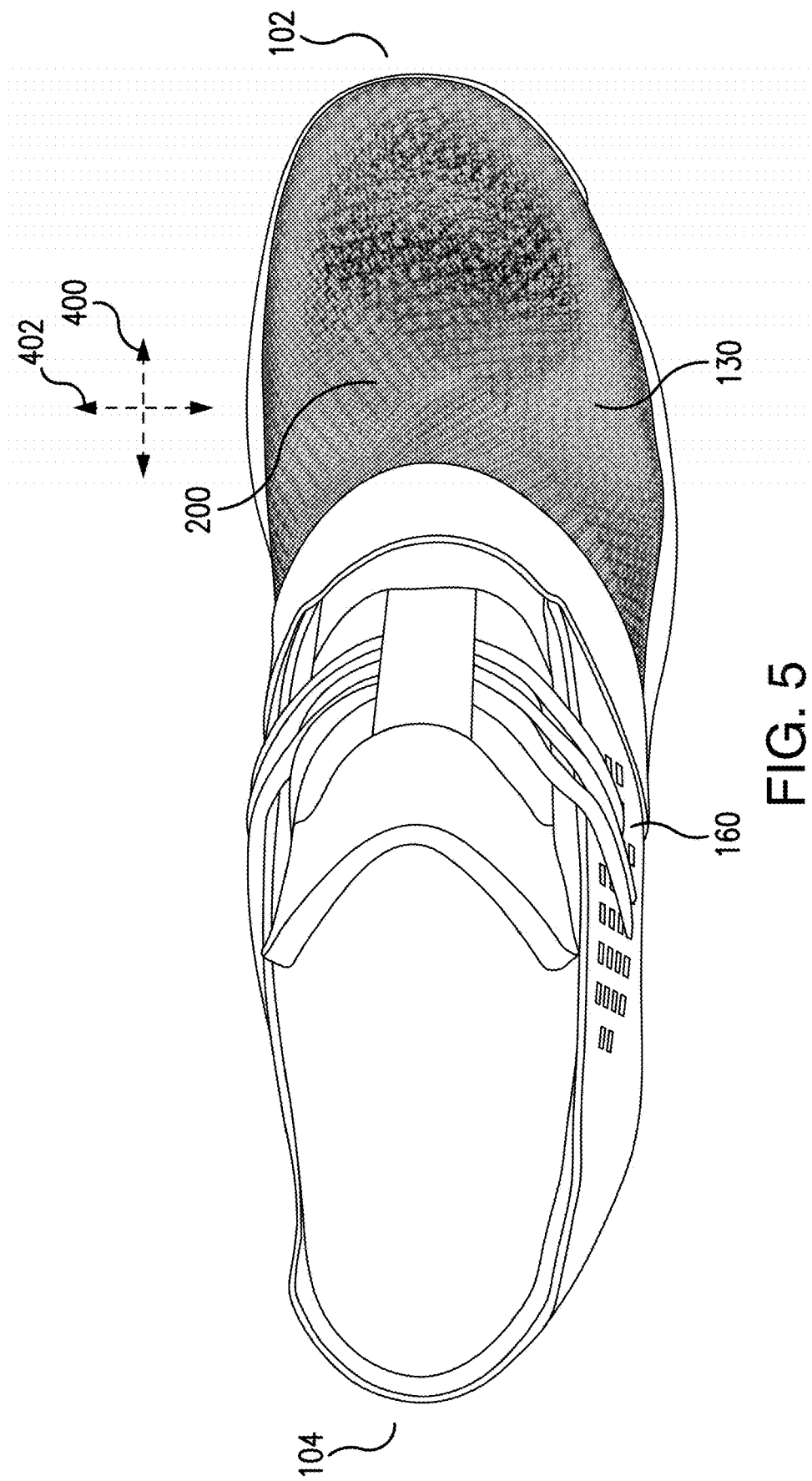
FIG. 5 is a top view of an article of footwear according to some embodiments.

As shown, for example in FIG. 3, upper 120 of article of footwear 100 may include various sections, including but not limited to, a heel counter 300, an ankle cuff 310 (which may include a collar 312 and an Achilles heel protector 314), a dorsal section 320, which may also be called a "lace component" (which may include a tongue 322 and a throat 324), a vamp section 330, a toe box section 340, and quarter sections 350. One quarter section 350 may be located on medial side 106 of article of footwear 100 and the other quarter section 350 is located on lateral side 108 of article of footwear 100. Dorsal section 320 may include a conventional tongue or may be "tongue-less". Sections 300, 310, 320, 330, 340, and 350 are not intended to demarcate precise areas of upper 120. Rather, sections 300, 310, 320, 330, 340, and 350 are intended to represent general areas of upper 120 that provide a frame of reference in the context of the present application.

In some embodiments, first portion 130 may define all or a portion of heel counter 300, ankle cuff 310, dorsal section 320, vamp section 330, toe box section 340, and/or quarter section(s) 350 of upper 120. In some embodiments, first portion 130 may define all or a portion of vamp section 330, toe box section 340, and quarter sections 350 of upper 120. In some embodiments, second portion 160 may define all or a portion of heel counter 300, ankle cuff 310, dorsal section 320, vamp section 330, toe box section 340, and/or quarter section(s) 350 of upper 120. In some embodiments, second portion 160 may define all or a portion of heel counter 300, ankle cuff 310, and dorsal section 320 of upper 120.

As shown in FIGS. 1-5, upper 120 includes a patterned material 200 with polymer threads stitched in one or more patterns on a surface of a base material. All or a portion of upper 120 may include patterned material 200. In some embodiments, first portion 130 may include patterned material 200. In some embodiments, second portion 160 may include patterned material 200. In some embodiments, both first portion 130 and second portion 160 may include patterned material 200. In some embodiments, patterned material 200 may be a single, continuous material defining at least defining at least a portion of upper 120. In some embodiments, patterned material 200 may include a plurality of patterned material sections coupled together to define at least a portion of upper 120. In some embodiments, patterned material 200 may be embossed.

In some embodiments, first portion 130 may consist of patterned material 200. In other words, in some embodiments, first portion 130 may be made only and entirely of patterned material 200. In some embodiments, first portion 130 may comprise a partial foot or full foot bootie. In this manner, upper 120 may be formed without seams. In some embodiments, upper 120 may include only a first portion 130 including patterned material 200 and a heel counter 162.

In some embodiments, patterned material 200 may define at least 50% of upper 120. In some embodiments, patterned material 200 may occupy at least 50% of the outer surface area of upper 120. In some embodiments, patterned material 200 may be visibly exposed on the outer surface of upper. In such embodiments, no lamination layer or supporting textile layer is disposed over patterned material 200 on the outer surface of upper 120. In some embodiments, upper 120 may be devoid of a lamination layer. Patterned material 200 may eliminate the need for a separate lamination layer because, as discussed herein, polymer thread(s) of patterned material 200 may be stitched to a base layer and directly bonded to a base layer and/or each other via polymeric material(s) of the polymer thread(s) Eliminating the need for a separate lamination layer may simplify manufacturing and reduce the cost of manufacturing an upper.

Patterned material 200 may provide targeted characteristics (e.g., breathability, stretchability, and strength) to areas of upper 120. Patterned material 200 may be include polymer thread set(s) stitched in one or more patterns on a base layer as described herein. In some embodiments, the stitching pattern(s), overlap between thread sets, and/or bonding of thread sets on patterned material 200 may provide targeted characteristics to areas of upper 120.

In some embodiments, patterned material 200 may include polymer thread(s) stitched on an outermost surface of patterned material 200, which may be the outermost surface of at least a portion of upper 120. In such embodiments, polymer thread(s) will be visibly exposed on the outermost surface of upper 120. In some embodiments, patterned material 200 may include polymer thread(s) stitched on an innermost surface of patterned material 200, which may be the innermost surface of at least a portion of upper 120. In such embodiments, the polymer thread(s) may be concealed from view on upper 120, but serve the same function of providing targeted characteristics to areas of upper 120.

In some embodiments, patterned material 200, or a portion thereof, may have a first degree of stretchability/strength in a longitudinal direction 400 between forefoot end 102 and heel end 104 of upper 120 and a second stretchability/strength in a transverse direction 402 between a medial side 106 and a lateral side 108 of upper 120. In some embodiments, the first stretchability/strength may be greater than the second stretchability/strength. In some embodiments, the first stretchability/strength may be less than the second stretchability/strength. In some embodiments, the stretchability/strength of patterned material 200 may be configured to have an angled stretchability/strength (i.e., a maximum or minimum stretchability/strength in a direction between longitudinal direction 400 and transverse direction 402). In some embodiments, different degrees and/or directions of stretchability/strength in different sections/areas of upper 120 may be used to create angled stretchability/strength for upper 120 as a whole.

Figure 6:
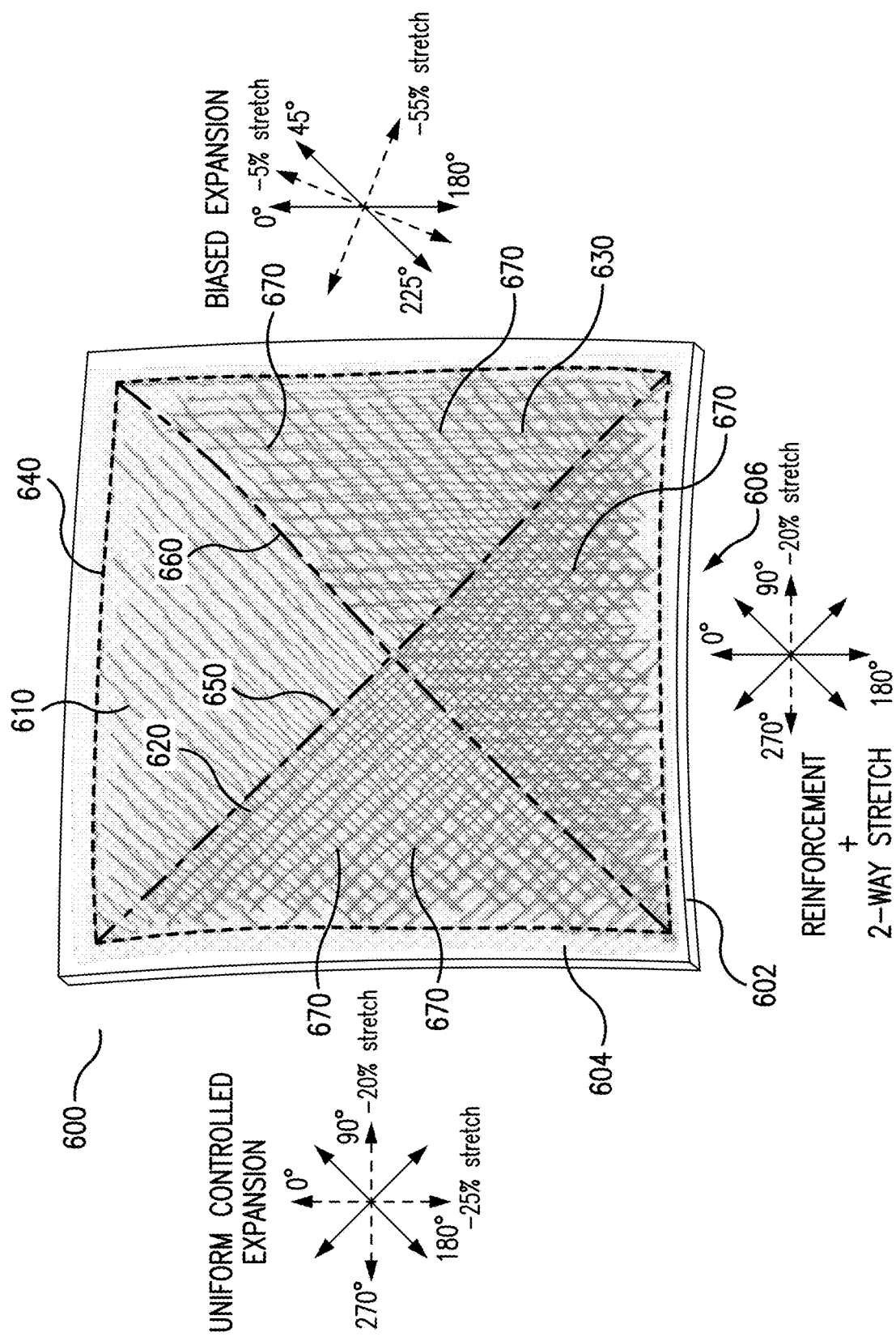
FIG. 6 is an exemplary patterned material with polymer threads stitched on a surface of a base layer in various patterns according to some embodiments.

FIG. 6 shows a patterned material 600 with polymer threads stitched on a base layer 602 according to some embodiments. Base layer 602 includes a top surface 604 and a bottom surface 606. Threads may be stitched on top surface 604 of base layer 602 in various patterns. In some embodiments, threads may alternatively or additionally be stitched on bottom surface 606 of base layer 602. As shown in FIG. 6, patterned material 600 may include a first thread set 610, a second thread set 620, and a third thread set 630. In some embodiments, at least one of the thread sets 610/620/630 includes polymer thread(s). In some embodiments, a plurality of the thread sets 610/620/630 include polymer thread(s). In some embodiments, first thread set 610, second thread set 620, and third thread set 630 may include polymer thread(s).

As used herein the term "polymer thread" means a thread composed at least in part of a polymeric material. In some embodiments, a polymer thread may be composed entirely of one or more polymeric materials. In some embodiments, a polymer thread may include a polymeric material coated around a core (which may or may not be composed of a polymeric material). In some embodiments, a polymer thread may include a polymer core coated or covered with a non-polymeric material. In some embodiments, a polymer thread may be a braided thread with one or more braids composed of a polymeric material. In some embodiments, the polymeric material(s) of a polymer thread may be thermoplastic material(s).

In some embodiments, the polymeric material(s) for threads in first thread set 610, second thread set 620, and/or third thread set 630 may be the same. In some embodiments, the polymeric material(s) for threads in first thread set 610, second thread set 620, and/or third thread set 630 may be different. The polymeric material(s) of different thread sets in a patterned material may be selected to provide targeted characteristics to areas of a patterned material, and therefore an upper. In embodiments including polymer thread(s) having a core coated with a polymeric material, the material of the core for different thread sets may be different or the same. And the material of core for different thread sets may be selected to provide targeted characteristics to different areas of a patterned material, and therefore an upper. Similarly, for braided polymer threads, the material(s) of the braided polymer thread(s) may be selected to provide targeted characteristics to different areas of a patterned material, and therefore an upper.

In some embodiments, the color of polymeric material(s) for threads in first thread set 610, second thread set 620, and/or third thread set 630 may be the same. In some embodiments, the color of polymeric material(s) for threads in first thread set 610, second thread set 620, and/or third thread set 630 may be different.

Suitable polymeric materials for polymer threads discussed herein include, but are not limited to thermoplastic polyurethane (TPU), a rubber, and silicone. In some embodiments, the TPU may be recycled TPU. In some embodiments, the polymeric material may be a photo-reactive (infra-red or ultraviolet light reactive) polymeric material, such as a photo-reactive TPU. In some embodiments, the polymeric material may be soluble (e.g., water soluble). In embodiments including polymer threads with a coated core, suitable materials for the core include, but are not limited to, polyester, nylon, ultra high molecular weight polyethylene (e.g., DYNEEMA® (a type of ultra high molecular weight polyethylene)), carbon fiber, KEVLAR® (a type of para-aramid), bioengineered woven, knit or layered materials (e.g., synthetic spider silk), woven, knit or layered plant based materials, knit or layered recycled and/or extruded plastics, cotton, wool, and natural or artificial silk.

In some embodiments, polymer threads may be threads coated with a thermoplastic polymer coating having a matte coating finish. A matte coating finish for a polymer thread is generally less tacky than a non-matte finished coating. A less tacky matte coating finish may facilitate stitching of threads to a base layer by reducing friction between polymer thread(s) and a base layer during a stitching processing. In some embodiments, polymer threads coated with a thermoplastic polymer coating having a matte coating finish may be thermoplastic polyurethane coated polyester threads with a matte coating finish produced by Sambu Fine Chemical Co., Ltd. of Korea.

In some embodiments, polymer threads or non-polymer threads of a patterned material may have a denier in the range of 350 D to 950 D. In some embodiments, polymer threads or non-polymer threads of a patterned material may have a denier of equal to or less than 3000 D. In some embodiments, the denier of polymer thread(s) in one or more thread sets on a base material may be selected to provide varying degrees of a characteristic (e.g., strength or stretchability) to different areas of a base material, and therefore an upper. In embodiments, including coated threads, the denier of the core material and/or the overall denier of the thread(s) may be selected to provide varying degrees of a characteristic (e.g., strength or stretchability) to different areas of a base material, and therefore an upper. As a non-limiting example, a larger overall diameter or a larger core diameter for a given polymer thread may increase the degree of directional strength imparted by a thread set including the polymer thread.

In some embodiments, threads in thread sets 610/620/630 may include a reflective material (e.g., a reflective coating material or a reflective material braided in the thread). In some embodiments, threads in thread sets 610/620/630 may include a rubberized material (e.g., a rubberized coating material or a rubberized material braided in the thread).

Base layer 602 may be, but is not limited to, woven layer, a knitted layer, a non-woven layer, and a leather layer. In some embodiments, base layer 602 may be made of a layer of synthetic material. In some embodiments, base layer 602 may be a woven, non-woven, or knitted polymeric layer. In some embodiments, base layer 602 may be a woven, non-woven, or layer composed of thermoplastic polyurethane (TPU), polyester, polyamide, polyethylene (PE), PE foam, polyurethane (PU) foam, and co-polymers or polymer blends including one or more these polymers. In some embodiments, base layer 602 may be a bioengineered woven, knitted or layered synthetic spider silk, woven, knitted or layered plant based materials, or woven, knit or layered recycled and/or extruded plastics. In some embodiments, base layer 602 may be film or sheet of a polymeric material, such as thermoplastic polyurethane (TPU), polyester, polyamide, polyethylene (PE), PE foam, polyurethane (PU) foam, and co-polymers or polymer blends including one or more these polymers. In some embodiments, base layer 602 may include a plurality of layers stacked vertically and/or arranged side-by-side. In some embodiments, the plurality of layers may be laminated.

As shown in FIG. 6, polymer thread sets 610/620/630 may be stitched in different patterns on different areas of base layer 602. First thread set 610 may be stitched in a first pattern on a first area 640 of base layer 602. Second thread set 620 may be stitched in a second pattern on a second area 650 of base layer 602. Third thread set 630 may be stitched in a third pattern on a third area 660 of base layer 602. The stitching patterns and overlap of first thread set 610, second thread set 620, and third thread set 630 may provide targeted characteristics to areas of base layer 602.

In some embodiments, first thread set 610 may be stitched in a first direction on top surface 604 of base layer 602. For example, as shown in FIG. 6, first thread set 610 may be stitched in a 45 degree/225 degree direction on top surface 604 of base layer 602. In some embodiments, second thread set 620 may be stitched in a second direction on top surface 604 of base layer 602. For example, as shown in FIG. 6, second thread set 620 may be stitched in a 135 degree/315 degree direction of top surface 604 of base layer 602. In some embodiments, third thread set 630 may be stitched in a third direction on top surface 604 of base layer 602. For example, as shown in FIG. 6, third thread set 630 may be stitched in a 0 degree/180 degree direction on top surface 604 of base layer 602. In some embodiments, the first pattern of first thread set 610, the second pattern of second thread set 620, and/or the third pattern of third thread set 630 may be customized based on a biometric data profile for an individual, or group of individuals (e.g., as discussed in regards to step 1302 in FIG. 13).

In some embodiments, at least one characteristic of base layer 602 may vary between first area 640, second area 650, and/or third area 660. The characteristic may be, but is not limited to ventilation, insulation, stretchability, and strength. In some embodiments, the characteristic may be a directional characteristic or composite characteristic, such as a directional strength or stretchability or a composite strength or stretchability.

As used herein, the term "directional characteristic" means a characteristic provided in a specific linear direction across an area of a base material/layer. A directional characteristic is a characteristic that is anisotropic and has a maximum/minimum value in a particular linear direction. For example, a thread set (e.g., polymer thread set) may function like a ply in a composite lay-up. The orientation of thread(s) in a thread set may provide directional characteristics in a similar fashion as the fiber material embedded in a matrix of a ply in a composite layup. Threads sets may be layered in a similar fashion as composite plies to provide characteristics (e.g., strength and stretchability characteristics) to areas of a base layer.

In some embodiments, first stitching pattern of first thread set 610 may impart a first directional characteristic (e.g., directional strength and/or directional stretchability) to first area 640 of base layer 602. Second stitching pattern of second thread set 620 may impart a second directional characteristic (e.g., directional strength and/or directional stretchability) to second area 650 of base layer 602. Third stitching pattern of third thread set 630 may impart a third directional characteristic (e.g., directional strength and/or directional stretchability) to third area 660 of base layer 602.

The stitching direction and overlap between different stitching directions of first thread set 610, second thread set 620, and third thread set 630 may produce areas having different characteristics. Overlap between stitching patterns of thread sets, such as first thread set 610, second thread set 620, and third thread set 630, may impart composite characteristics to areas of base layer 602. As used herein, the term "composite characteristic" means a characteristic provided by two or more directional characteristics in an area of overlap between structure (e.g., a thread set) providing a first directional characteristic, structure (e.g., a second thread set) providing a second directional characteristic, etc. In other words, a composite characteristic is a combination of two or more directional characteristics. In some embodiments, a composite characteristic may be an isotropic characteristic.

For example, as shown in FIG. 6, overlap between first thread set 610 and second thread set 620 may produce a composite characteristic area of uniform controlled expansion with a 20% reduction in stretch in the 90 degree/270 degree direction (measured relative to the intrinsic stretch properties of base layer 602) and a 25% reduction in stretch in the 0 degree/180 degree direction. As another example, overlap between first thread set 610 and third thread set 630 may produce a composite characteristic area of biased expansion with a 55% reduction in stretch in the 112.5 degree/292.5 degree direction and a 5% reduction in stretch in the 22.5 degree/202.5 degree direction. As another example, overlap between first thread set 610, second thread set 620, and third thread set 630 may produce a composite characteristic area of reinforcement and 2-way stretch having a 20% reduction in stretch in the 90 degree/270 degree direction.

In some embodiments, base layer 602 may have a stretch bias in a particular direction. For example, base layer 602 may be a woven or knitted fabric having a one-way stretch bias is a single direction, a two-way stretch bias, tri-axial stretch bias, or a four-way stretch bias. In some embodiments, thread sets stitched and/or bonded to a base layer may selectively reengineer the intrinsic stretch bias of the base layer and tailor the base layer to have varying stretch biases in different areas of upper. This may remove undesirable stretch biases in different areas of an upper resulting from the intrinsic stretch bias of a base material used to make an upper. For example, a base layer with a one-way stretch bias in a particular direction may result in an upper with desirably stiff quarter sections due to the stretch bias of the base layer, but the upper may have an undesirably high degree of stretchability in another area (e.g., in a vamp section). Stitching and bonding thread sets to a base material may alleviate undesirable degrees of stretchability in sections of an upper without having to change the material of a base layer and/or without having to use multiple base layer materials to construct an upper.

In some embodiments, all or a portion of thread sets 610/620/630 may be bonded to top surface 604 of base layer 602. In some embodiments, all or a portion of thread sets 610/620/630 may be directly bonded to top surface 604 of base layer 602 via the polymeric material(s) of first thread set 610, second thread set 620, and/or third thread set 630. In some embodiments, thread(s) in thread sets 610/620/630 may be bonded together at fuse points 670. Thread(s) of thread sets 610/620/630 may be directly bonded to each other via the polymeric material(s) of first thread set 610, second thread set 620, and/or third thread set 630. In some embodiments, a non-polymer thread set (e.g., second thread set 620) may be sandwiched between and bonded to polymer thread sets disposed on opposite sides of the non-polymer thread set (e.g., first thread set 610 and third thread set 630). In some embodiments, patterned material 600 may include a polymeric base layer 602 (e.g., a base layer composed of TPU) and a plurality of non-polymer thread sets. In such embodiments, the non-polymer thread sets may be directly bonded to the polymeric base layer.

In some embodiments, a thread set may include a continuous thread defining the entirety of the thread set. In some embodiments, a plurality of thread sets may be defined by a continuous thread defining all or a portion of the plurality of thread sets. In some embodiments, all the thread sets stitched on a base layer may be defined by a single continuous thread. In some embodiments, a thread set may include a plurality of non-continuous threads defining portions of the thread set.

Figure 7:
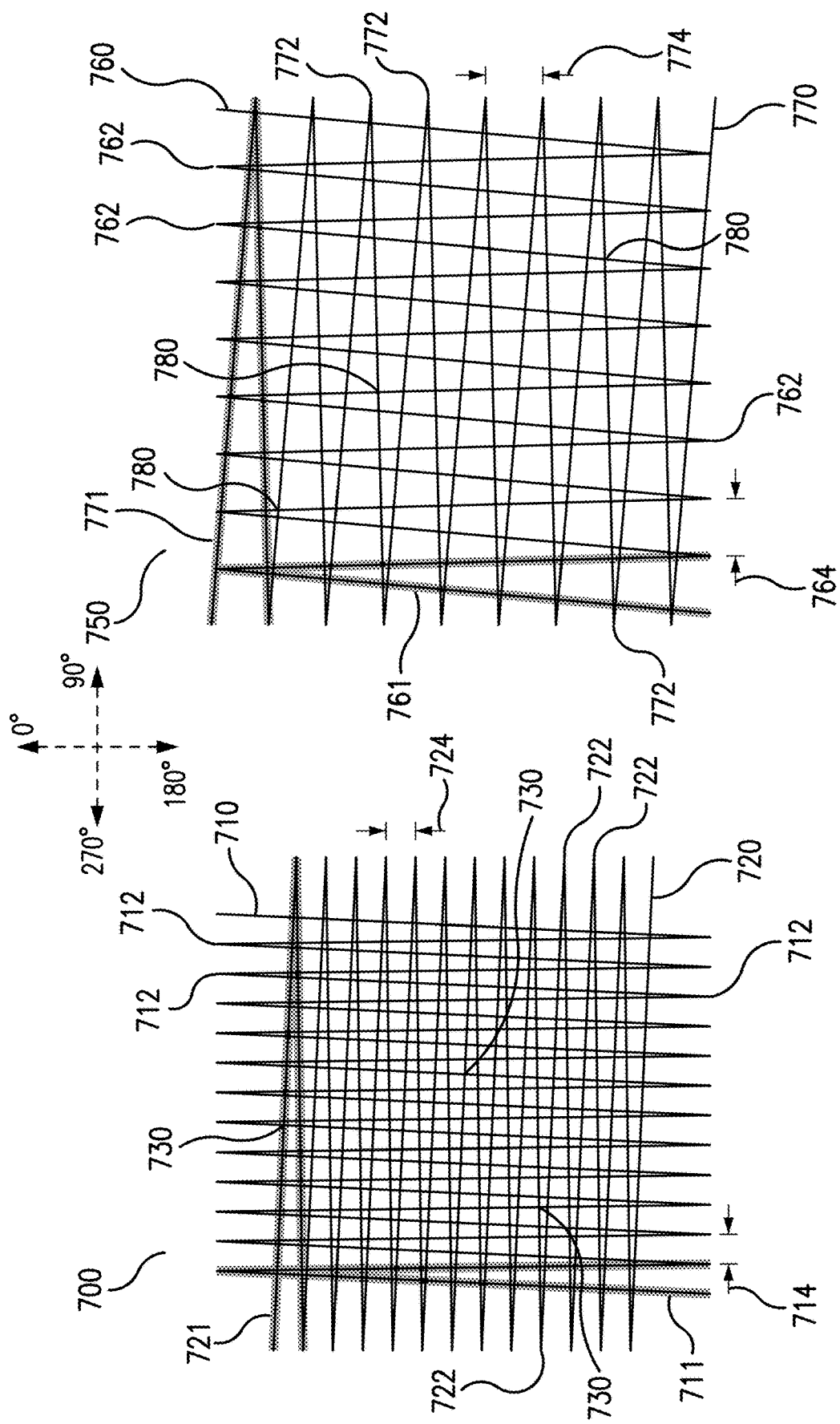
FIG. 7A is a zigzag pattern according to some embodiments with apexes of the zigzag pattern spaced apart by a first distance.
FIG. 7B is a zigzag pattern according to some embodiments with apexes of the zigzag pattern spaced apart by a second distance.

As shown in FIGS. 7A and 7B, thread sets may be composed of a plurality of thread lines stitched in an oscillating pattern (e.g., a zigzag or wave pattern). FIG. 7A shows a thread pattern 700 including a first thread set 710 composed of thread lines 711 and a second thread set 720 composed of thread lines 721. Each thread line 711/721 may define one oscillation of an oscillating pattern and an apex of the oscillating pattern. FIG. 7A shows apexes 712 of first thread set 710 and apexes 722 of second thread set 720.

While FIG. 7A shows first thread set 710 and second thread set 720 arranged in a zigzag pattern with pointed apexes 712/722, thread sets 710/720 may be arranged in any suitable reciprocating pattern, such as but not limited to, a wave pattern with rounded apexes and a square wave pattern with straight-edge apexes. In some embodiments, first thread set 710 and second thread set 720 may be arranged in the same oscillating pattern. In some embodiments, first thread set 710 and second thread set 720 may be arranged in different oscillating patterns.

The direction in which an apex points may define the directional orientation (stitching direction) of an oscillating pattern for a thread set. For example, as shown in FIG. 7A apexes 712 of first thread set 710 point in a 0 degree/180 direction and apexes 722 of second thread set 720 point in a 90 degree/270 degree direction. In embodiments including non-pointed apexes (e.g., rounded or straight-edge apexes), the stitching direction of a thread set may be defined by the direction orthogonally tangential to the peaks of the apexes in a thread set. In some embodiments, as shown for example in FIG. 7A, the stitching direction of a thread set may remain constant throughout a thread set. In some embodiments, the stitching direction of a thread set may vary in a thread set (see e.g., third polymer thread set 1940 in FIG. 19). Varying the stitching direction of a thread set may vary the directional characteristic(s) imparted by the thread set in an area of a base layer, and therefore an area of an upper.

Apexes 712 of first thread set 710 may be separated by a first distance 714 and apexes 722 of second thread set 720 may be separated by a second distance 724. In some embodiments, first distance 714 may be equal to second distance 724. In some embodiments, first distance 714 and second distance 724 may be different. In some embodiments, first distance 714 and second distance 724 may be the range of 1.0 mm to 10.0 mm. In some embodiments, first distance 714 and second distance 724 may be in the range of 2.0 mm to 6.0 mm.

The distance between apexes in a stitch pattern (e.g., distances 714 and 724) may be tailored to control the characteristics (e.g., direction characteristics) imparted by a thread set. For example, a smaller distance between apexes may increase the degree of strength imparted by a given thread set. As another example, a smaller distance between apexes may decrease the degree of stretchability imparted by a given thread set. In some embodiments, the distance between apexes in a thread set may be constant throughout the thread set. In some embodiments, the distance between apexes in a thread set may vary in the thread set. Varying the distance between apexes in a thread set may vary the degree of characteristics (e.g., directional characteristics) imparted by the thread set.

FIG. 7B shows a thread pattern 750 including a first thread set 760 composed of thread lines 761 and a second thread set 770 composed of thread lines 771. First thread set 760 and second thread set 770 may be the same as first thread set 710 and second thread set 720, but the distances 764 and 774 between apexes 762 and 772 of thread sets 760 and 770 are larger than the distances 714 and 724 between apexes 712 and 722 of thread sets 710 and 720. Larger distances 764 and 774 may decrease the degree of directional strength imparted by thread sets 760 and 770, relative to thread sets 710 and 720. Also, larger distances 764 and 774 may result a higher degree of directional stretchability imparted by thread sets 760 and 770, relative to thread sets 710 and 720. As illustrated in FIGS. 7A and 7B, increasing the spacing between apexes may also increase the spacing between fuse points 730/780 in thread sets. Increasing the distance between fuse points in overlapping thread sets may decrease the degree of directional strength imparted by overlapping thread sets and may result in a higher degree of directional stretchability imparted by the overlapping thread sets due to less bonding between overlapping thread lines.

Figure 8:
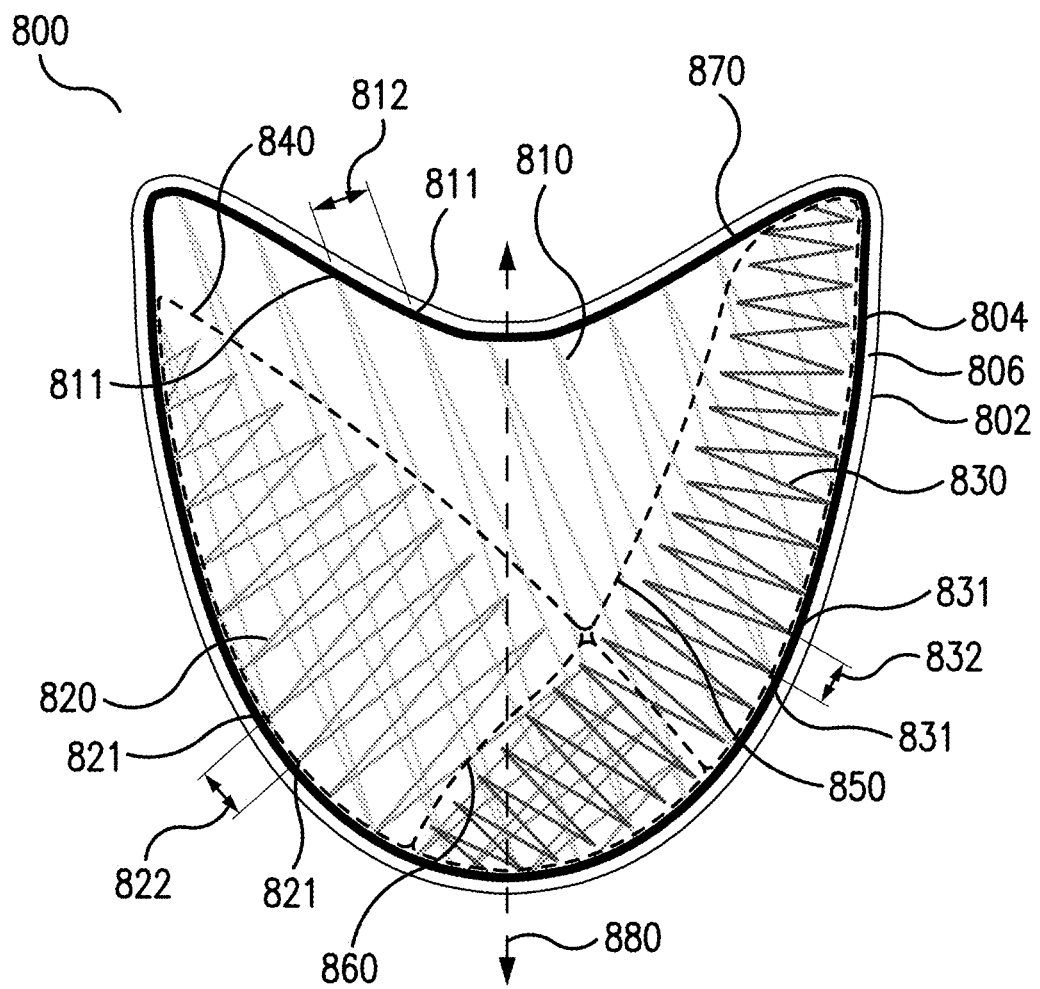
FIG. 8 is a thread pattern for an upper with patterned polymer threads according to some embodiments.

FIG. 8 shows an exemplary thread pattern 800 for a portion of an upper (e.g., first portion 130 of upper 120). Thread pattern 800 includes a peripheral edge 804 disposed in a peripheral region 806 of a base layer 802. Thread pattern 800 includes a first thread set 810 including apexes 811 separated by a first distance 812, a second thread set 820 including apexes 821 separated by a second distance 822, and a third thread set 830 including apexes 831 separated by a third distance 832. First thread set 810 overlaps second thread set 820 in first overlap area 840. First thread set 810 overlaps third thread set 830 in second overlap area 850. And first thread set 810, second thread set 820, and third thread set 830 overlap in third overlap area 860. Similar to thread sets 610, 620, and 630, thread sets 810, 820, and 830 may impart directional characteristics to the areas in which they are stitched on base layer 802. Also, first overlap area 840, second overlap area 850, and third overlap area 860 may impart composite characteristics to areas on base layer 802.

In some embodiments, a portion of one or more polymer thread sets may be disposed in peripheral region 806 of base layer. In such embodiments, the polymer thread set(s) may be coupled to footwear components (e.g., a heel counter or a sole) in a sole connection area of an upper (e.g., sole connection area 136 of upper 120) or an upper connection area of an upper (e.g., upper connection area 134 of upper 120). Such coupling may facilitate energy transfer from polymer thread set(s) to other footwear components.

In some embodiments, thread pattern 800 may include a reinforcement area 870 stitched around peripheral edge 804 in peripheral region 806 of base layer 802. Reinforcement area 870 may include polymer thread(s) densely stitched to form a defined area predominantly occupied by polymer thread(s). In such embodiments, when the polymer thread(s) of reinforcement area 870 are bonded to base layer 802, the polymer thread(s) may form a layer of polymeric material in reinforcement area 870. In some embodiments, adjacent polymer threads lines stitched in reinforcement area 870 may be stitched such that they are immediately adjacent to and in contact with each other. In some embodiments, adjacent polymer thread(s) of reinforcement area 870 may stitched in an oscillating pattern with apexes spaced apart by a distance of 1.0 mm or less.

In some embodiments, reinforcement area 870 may be disposed in a sole connection area of an upper (e.g., sole connection area 136 of upper 120) or an upper connection area of an upper (e.g., upper connection area 134 of upper 120) to provide increased strength at attachment points between base layer 802 and a sole (e.g., sole 180) and/or at attachment points between base layer 802 and other portions of an upper (e.g., second portion 160 of upper 120)

FIG. 8 also shows an exemplary upper mid-line 880 which may be used to measure the stitch direction of thread sets on a base layer or upper (e.g., first thread set 810, second thread set 820, and third thread set 830). Upper mid-line 880 is an imaginary line running along the geometrical center of an upper in longitudinal direction 400 between a forefoot end of the upper and a heel end of the upper (see e.g., FIG. 4). As shown in FIG. 8, thread lines of first thread set 810 may be oriented at a first angle relative mid-line 880, thread lines of second thread set 820 may be oriented at a second angle relative to mid-line 880, and thread lines of a third thread set 830 may be oriented at a third angle relative to mid-line 880. In some embodiments, the first angle, the second angle, and the third angle may be different.

FIGS. 9A and 9B show a patterned material 900 for an upper (e.g., upper 120) with polymer threads 908 stitched on a base layer 902 of patterned material 900 according to some embodiments. FIG. 9A shows a top surface 904 of base layer 902 and FIG. 9B shows a bottom surface 906 of base layer 902. Polymer thread(s) 908 may be the same as or similar to the polymer thread(s) for polymer thread sets 610/620/630 discussed in regards to FIG. 6. And base layer 902 may be the same as or similar to base layer 602 discussed in regards to FIG. 6.

Base layer 902 may define at least a portion of an upper (e.g., first portion 130 of upper 120). As shown in FIG. 9A, one or more polymer threads 908 may be stitched to an outer surface (e.g., top surface 904) of base layer 902 in one or more patterns. In some embodiments, top surface 904 with stitched polymer thread(s) 908 may define at least a portion of an outermost surface of an upper (e.g., upper 102). Polymer thread(s) 908 may include a first polymer thread set 910 stitched in a first pattern on top surface 904 of base layer 902. First polymer thread set 910 may be stitched in a first pattern including polymer thread lines oriented in a first direction 990. Polymer thread(s) 908 may also include a second polymer thread set 920 stitched in a second pattern on top surface 904 of base layer 902. Second polymer thread set 920 may be stitched in a second pattern including polymer thread lines oriented in a second direction 992 different from first direction 990.

In some embodiments, polymer thread(s) 908 may include a third polymer thread set 930 stitched in a third pattern on top surface 904 of base layer 902. Third polymer thread set 930 may be stitched in a third pattern including polymer thread lines oriented in a third direction 994 different from first direction 990 and second direction 992. First direction 990, second direction 992, and third direction 994 may be defined by their angle of orientation measured relative to a mid-line of patterned material 900 (e.g., measured relative to longitudinal direction 400).

In some embodiments, at least a portion of first polymer thread set 910 may overlap at least a portion of second polymer thread set 920 in a first overlap area. In some embodiments, at least a portion of first polymer thread set 910 may be directly bonded to base layer 902 in the first overlap area via a polymeric material of polymer thread(s) in first polymer thread set 910. In some embodiments, at least a portion of first polymer thread set 910 may be directly bonded to base layer 902 via a coating of polymer thread(s) 908 (e.g., coating 916 shown in FIG. 10) in first polymer thread set 910. In some embodiments, at least a portion of second polymer thread set 920 may be directly bonded to base layer 902 in the first overlap area via a polymeric material of polymer thread(s) 908 in second polymer thread set 920 (e.g., via the coating of the polymer thread(s) 908 in second polymer thread set 920).

In some embodiments, at least a portion of first polymer thread set 910 and at least a portion of second polymer thread set 920 that overlap in the first overlap area may be directly bonded to each other via polymeric material(s) of polymer thread(s) 908 in first polymer thread set 910 and second polymer thread set 920 (e.g., via coatings of the polymer thread(s) 908 in first polymer thread set 910 and polymer thread(s) 908 in second polymer thread set 920).

In some embodiments, at least a portion of third polymer thread set 930 may overlap at least a portion of first polymer thread set 910 in a second overlap area. In some embodiments, at least portion of third polymer thread set 930 and at least a portion of first polymer thread set 910 that overlap in the second overlap area may be directly bonded to each other via polymeric material(s) of the polymer thread(s) 908 in first polymer thread set 910 and third polymer thread set 930 (e.g., via coatings of the polymer thread(s) 908 in first polymer thread set 910 and the polymer thread(s) 908 in third polymer thread set 930). In some embodiments, at least a portion of third polymer thread set 930 may be directly bonded to base layer 902 in the second overlap area via a polymeric material of polymer thread(s) in third polymer thread set 930

In some embodiments, at least a portion of third polymer thread set 930, at least a portion of second polymer thread set 920, and at least a portion of first polymer thread set 910 may overlap in a third overlap area. In some embodiments, at least portion of third polymer thread set 930, at least a portion of second polymer thread set 920, and at least a portion of first polymer thread set 910 that overlap in the third overlap area may be directly bonded to each other via polymeric material(s) of the polymer thread(s) 908 in third polymer thread set 930, second polymer thread set 920, and first polymer thread set 910. For example, via coatings of the polymer thread(s) 908 in first polymer thread set 910, the polymer thread(s) 908 in second polymer thread set 920, and the polymer thread(s) 908 in third polymer thread set 930.

In some embodiments, the first pattern of first polymer thread set 910 may impart a first directional characteristic to a first area of partnered material 900, and therefore to a first area of an upper. The first directional characteristic may be a directional strength and/or directional stretchability in first direction 990. In some embodiments, the second pattern of second polymer thread set 920 may impart a second directional characteristic to a second area of patterned material 900, and therefore to a second area of an upper. The second directional characteristic may be a directional strength and/or directional stretchability measured in second direction 992. In some embodiments, the third pattern of third polymer thread set 930 may impart a third directional characteristic to a third area of patterned material 900, and therefore to a third area of upper. The third directional characteristic may be a directional strength and/or directional stretchability measured in third direction 994.

Areas of overlap between thread patterns on patterned material 900 may impart composite characteristics to areas of patterned material 900, and therefore areas of an upper. The composite characteristic may be a composite stretchability and a composite strength (e.g., composite stretchability characteristics described in regards to FIG. 6). While FIG. 9A shows patterned material 900 having three polymer thread sets, patterned material 900 may include more than three polymer thread sets. For example, patterned material may include four polymer thread sets, five polymer thread sets, six polymer thread sets, or seven polymer thread sets. In some embodiments, one or more thread sets of patterned material 900 may be non-polymer thread sets. Similar to first polymer thread set 910, second polymer thread set 920, and third polymer thread set 930, additional polymer thread sets or non-polymer thread sets may impart directional characteristics to areas of patterned material 900. And areas of overlap between addition thread sets may impart composite characteristics to areas of patterned material 900.

As shown for example in FIG. 9B, one or more backing threads 940 may be disposed on a second outer surface (e.g., bottom surface 906) of base layer 902 opposite top surface 904. In some embodiments, bottom surface 906 may define at least a portion of an innermost surface of an upper (e.g., upper 102). Polymer thread set(s) (e.g., thread sets 910, 920, and 930) stitched to base layer 902 may be stitched around backing thread(s) 940 to secure the polymer thread set(s) to base layer 902. In some embodiments, backing thread(s) 940 may be bobbin thread(s). In some embodiments, backing thread(s) 940 may be polymer thread(s). In some embodiments, backing thread(s) 940 may be non-polymer thread(s). In some embodiments, backing thread(s) 940 may be polyester or nylon thread(s).

In some embodiments, backing thread(s) 940 may be a thread coated with a thermoplastic polymer coating. In some embodiments, backing thread(s) 940 may be thread(s) coated with a thermoplastic polymer coating having a matte coating finish. In some embodiments, backing thread(s) 940 may be thermoplastic polyurethane coated polyester thread(s) with a matte coating finish produced by Sambu Fine Chemical Co., Ltd. of Korea.

In some embodiments, patterned material 900 may include a backing layer stitched to bottom surface 906. In some embodiments, one or more thread sets may be stitched through the backing layer to couple the backing layer to bottom surface 906. In embodiments including a backing layer, the backing layer may provide cushioning on bottom surface 906 of patterned material 900.

FIG. 9C shows a portion of a patterned material 950 including a first polymer thread set 960 and a second polymer thread set 970 stitched on a top surface 954 of a base layer 952. In some embodiments, second polymer thread set 970 may be stitched over first polymer thread set 960 in an area of overlap between first polymer thread set 960 and second polymer thread set 970. In areas of overlap discussed herein, polymer thread sets may be stitched over each other in the same or a similar fashion as illustrated in FIG. 9C.

As shown in FIG. 10, polymer thread(s) 908 (or non-polymer threads) of patterned material 900 may stitched through base layer 902 in a vertical direction (e.g., vertical direction 404 shown in FIG. 4) between top surface 904 of base layer 902 and bottom surface 906 of base layer 902. Polymer thread(s) 908 may be stitched through base layer 902 and secured to base layer 902 with backing thread 940 at stitch points 919. Stitching polymer thread(s) 908 (or non-polymer threads) through base layer 902 may form patterns on top surface 904 of base layer 902 while also integrating polymer thread(s) 908 into base layer 902. In some embodiments, polymer thread(s) 908 may be bonded to bottom surface 906 of base layer 902 at stitch points 919.

Adjacent stitch points 919 may be separated by a stitch distance 918. In some embodiments, stitch distances 918 may be constant in a polymer thread set. In some embodiments, stitch distances 918 may vary within a defined numerical range in a polymer thread set. In some embodiments, stitch distances 918 may be randomized within a defined numerical range in a polymer thread set. In some embodiments, the defined numerical range may be 2.0 mm to 10.0 mm. In some embodiments, the defined numerical range may be 3.5 mm to 7.5 mm.

Varying or randomizing stitch distances 918 for a thread set may facilitate an even distribution of loads across a thread set, or group of thread sets. In some embodiments, varying or randomizing stitch distances 918 for a thread set, or group of thread sets may create thread lines with adjacent apexes positioned in a non-linear fashion (e.g., the undulating arrangement of apexes 1212 in FIGS. 12A and 12B). This non-linear positioning of apexes may help prevent adjacent thread lines from being stitched directly on each other, which may cause threads to break during manufacturing.

As shown in FIG. 10, polymer thread(s) 908 may include a core 914 and a coating 916. In some embodiments, core 914 may be composed of a core material and coating 916 may be composed of a polymeric coating material. In some embodiments, the melting point of the core material may be higher than the melting point of the polymeric coating material. In such embodiments, the polymeric coating material may facilitate direct bonding of polymer thread(s) 908 to top surface 904 of base layer 902 and/or to overlapping thread sets when heated, while the core material may be unaffected by the heating. In some embodiments, the polymeric coating material may be a thermoplastic material, such as but not limited to thermoplastic polyurethane. In some embodiments, the core material may be polyester. In some embodiments, the polymeric coating material may have a melting temperature in the range of 180 degrees C. to 80 degrees C. In some embodiments, the polymeric coating material may have a melting temperature in the range of 150 degrees C. to 180 degrees C. In some embodiments, the polymeric coating material may have a melting temperature in the range of 160 degrees C. to 170 degrees C.

FIGS. 11A and 11B show a patterned material 1100 for an upper (e.g., upper 120) with polymer thread(s) 1108 stitched on and bonded to a base layer 1102 of patterned material 1100 according to some embodiments. FIG. 11A shows a top surface 1104 of base layer 1102 and FIG. 11B shows a bottom surface 1106 of base layer 1102. Polymer thread(s) 1108 may be the same as or similar to the polymer thread(s) for polymer thread sets 610/620/630 discussed in regards to FIG. 6. And base layer 1102 may be the same as or similar to base layer 602 discussed in regards to FIG. 6.

Similar to base layer 902, base layer 1102 may define at least a portion of an upper (e.g., first portion 130 of upper 120). As shown in FIG. 11A, one or more polymer threads 1108 may be stitched and bonded to an outer surface (e.g., top surface 1104) of base layer 1102 in one or more patterns. In some embodiments, top surface 1104 with stitched and bonded polymer thread(s) 1108 may define at least a portion of an outermost surface of an upper (e.g., upper 102). Similar to polymer thread(s) 908, polymer thread(s) 1108 may include a first polymer thread set 1110 stitched and bonded in a first pattern on top surface 1104 of base layer 1102. Polymer thread(s) 1108 may also include a second polymer thread set 1120 stitched and bonded in a second pattern on top surface 1104 of base layer 1102. In some embodiments, polymer thread(s) 1108 may include a third polymer thread set 1130 stitched and bonded in a third pattern on top surface 1104 of base layer 1102.

As shown for example in FIG. 11B, one or more backing threads 1140 may be disposed on a second outer surface (e.g., bottom surface 1106) of base layer 1102 opposite top surface 1104. In some embodiments, bottom surface 1106 may define at least a portion of an innermost surface of an upper (e.g., upper 102). Similar to patterned material 900, polymer thread set(s) (e.g., thread sets 1110, 1120, and 1130) stitched and bonded to base layer 1102 may be stitched around backing thread(s) 1140. Backing thread(s) 1140 may be the same as or similar to backing thread(s) 940.

FIG. 11C shows a portion of a patterned material 1150 including a first polymer thread set 1160 and a second polymer thread set 1170 stitched to a base layer 1152 and bonded on a top surface 1154 of base layer 1152. In some embodiments, second polymer thread set 1170 may be stitched over first polymer thread set 1160 in an area of overlap between first polymer thread set 1160 and second polymer thread set 1170.

FIG. 11C also shows fuse points 1180 between polymer thread(s) of first polymer thread set 1160 and second polymer thread set 1170 in an area of overlap between first polymer thread set 1160 and second polymer thread set 1170. Fuse points 1180 are locations where polymer thread(s) of first polymer thread set 1160 are bonded (fused) to polymer thread(s) of second polymer thread set 1170. In areas of overlap discussed herein, polymer thread sets may be stitched over each other and bonded at fuse points in the same or a similar fashion as illustrated in FIG. 11C.

FIG. 12A shows an eyelet blank 1210 stitched on a base layer 1200 according to some embodiments. Eyelet blank 1210 may include polymer thread lines stitched immediately adjacent to each other in an area of base layer 1200. In some embodiments, eyelet blank 1210 may include a polymer thread sets stitched in different directions over each other in an area of base layer 1200. The dense concentration of polymer thread lines in eyelet blank 1210 may provide a large degree of strength in an area of base layer 1200 in which they are stitched. When heated, polymer thread(s) of eyelet blank 1210 may form a layer of polymeric material in the area in which they are stitched. In some embodiments, adjacent polymer thread lines of eyelet blank 1210 may stitched such that they are immediately adjacent to and in contact with each other. In some embodiments, polymer thread(s) of eyelet blank 1210 may stitched in an oscillating pattern with apexes 1212 spaced apart by a distance less than or equal to 1.0 mm.

In some embodiments with polymer thread(s) having a polymeric coating around a core, the overall denier of the thread(s) may be at least two times larger than the denier of the core more material. In some embodiments, the overall denier of the thread(s) may be at least three times or four times larger than the denier of the core more material. An overall denier of at least two times, three times, or four times larger than the denier of the core material may facilitate the formation of a polymeric layer on a base layer after the polymer thread(s) are bonded to the base layer due to the polymer thread(s) being composed of a significant amount of polymeric material.

As shown in FIG. 12B, eyelets 1220 may be formed in eyelet blank 1210 for lacing a lace on an article of footwear (e.g., shoe lace 192). In some embodiments, eyelets 1220 may be punched from eyelet blank 1210 before or after eyelet blank 1210 is heated to bond polymer thread(s) of eyelet blank 1210 to base layer 1200. In some embodiment, eyelets 1220 may be formed during stitching of eyelet blank

1210. In such embodiments, eyelet blank 1210 may be stitched around areas on base layer 1200 designated for eyelets 1220

In some embodiments, apexes 1212 of thread lines in eyelet blank 1210 may be stitched such that adjacent apexes 1212 are positioned in a non-linear fashion (e.g., the undulating arrangement of apexes 1212 in FIGS. 12A and 12B) on base layer 1200. This non-linear positioning of apexes 1212 may help prevent adjacent thread lines from being stitched directly on each other, which may cause threads to break during manufacturing.

In some embodiments, other support structures for an upper may be formed in a similar fashion as eyelet blank 1210. For example, a reinforcement area (e.g., reinforcement area 870) may be formed in a similar fashion as eyelet blank 1210. As another example, a heel counter for an upper may be formed on a base layer by stitching polymer thread lines immediately adjacent to each other in an area of a base layer. When heated, polymer thread(s) of forming the heel counter may form a layer of polymeric material in the area in which they are stitched. In some embodiments, one or more cushioning layers (e.g., a polymeric foam layer) may be encapsulated between a base layer and a support structure formed in a similar fashion as eyelet blank 1210. In such embodiments, the encapsulated cushioning layer(s) may provide additional cushioning and protection for portions of an individual's foot (e.g., a heel portion and/or an ankle portion). In some embodiments, the cushioning layer(s) may provide increased thermal insulation for portions of an individual's foot.

FIG. 13 shows a method 1300 of making an article of footwear (e.g. article of footwear 100) according to some embodiments. In step 1302, one or more polymer thread(s) (e.g., polymer thread 908) may be stitched in one or more patterns on an outer surface of a base layer (e.g., top surface 904 of base layer 902). In some embodiments, step 1302 may include stitching polymer thread(s) to form one or more eyelet blanks (e.g., eyelet blanks 1210) with or without eyelets. In some embodiments, the polymer thread(s) may be embroidered on the base layer. In some embodiments, the polymer thread(s) may be chain stitched on the base layer. In some embodiments, the polymer thread(s) may be stitched to the base layer with an automated stitching machine.

FIG. 14 shows an automated stitching system 1400 according to some embodiments. Automated stitching system 1400 includes a material support table 1402, a stitching machine 1404 and a controller 1406. Material support table 1402 provides a surface for supporting a base material/layer 1403. In some embodiments, the surface of material support table 1402 may be tailored to the desired shape of base material/layer 1403. For example, material support table 1402 may provide a flat two-dimensional surface, a contoured three-dimensional surface, or a compound, contoured three-dimensional surface.

In some embodiments, stitching machine 1404 may be a computer numerically controlled ("CNC") stitching machine. Stitching machine 1404 includes a stitching head 1410 configured to make a plurality of stitches on base material/layer 1403. Stitching head 1410 includes stitching needle(s) 1412 and a needle-drive mechanism 1414 for reciprocating the needle(s) 1412. The stitching machine 1404 also includes a motor group 1416 for positioning stitching head 1410 over base material/layer 1403. Motor group 1416 may include a first servo-controlled motor for positioning the needle(s) 1412 with respect to an x-axis and a second servo-controlled motor for positioning the needle(s) 1412 with respect to a y-axis. In some embodiments, motor group 1416 may include a third servo-controlled motor for positioning needle(s) 1412 with respect to a z-axis and/or a fourth servo-controlled motor for positioning needle(s) 1412 with respect to a rotational c-axis. The third and fourth servo-controlled motors would allow stitching machine 1404 to stitch a base material/layer 1403 having a compound, contoured three-dimensional surface. In some embodiments, motor group 1416 could include additional servo-controlled motors if additional degrees of freedom are desired.

Stitching machine 1404 may also include a bobbin assembly 1418 and a thread spool 1420 for supplying thread to the needle(s) 1412. A thread is drawn from spool 1420 and threaded through an eye of a needle 1412. Under control of controller 1406, motor group 1416 is configured to position a needle 1412 over a stitching point on base material/layer 1403 and the needle 1412 is plunged into base material/layer 1403. In operation, bobbin assembly 1418, which is on the underside of base material/layer 1403 grabs the thread and forms a loop, which locks the stitch. Needle 1412 is withdrawn from base material/layer 1403 and, under control of controller 1406, it is repositioned over the next stitching point. Once again, needle 1412 is plunged into base material/layer 1403, bobbin assembly 1418 grabs the thread, forms another loop, which locks the stitch, and needle 1412 is withdrawn from base material/layer 1403 and moved to the next stitching point. This stitching process may be repeated to create one or more patterns on a surface of base material/layer 1403.

In some embodiments, stitching machine 1404 may include a load cell 1422 placed near needle(s) 1412 along a thread path. Load cell 1422 may generate a tension feedback signal TN proportional to tension in the thread at or near the needle(s) 1412.

As shown in FIG. 14, controller 1406 includes a processor 1430 and a computer memory 1432. CNC code 1434 including instructions for instructing processor 1430 to control stitching machine 1404 may be encoded in computer memory 1432. A host program 1436 for executing the CNC instructions and causing an I/O circuit 1442 to send commands to stitching machine 1404 to perform the CNC instructions may also be encoded in the computer memory 1432. CNC code 1434 may include stitching instructions that contain the coordinates of stitching points. Processor 1430 processes the CNC instructions and, through I/O circuit 1442, commands motor group 1416 to move stitching head 1410 to the coordinates, and commands stitching head 1410 to make stitches at the coordinates. Processor 1430 may receive position feedback signals from motor group 1416 and close the control loop on the servo-controlled motors.

In some embodiments, CNC code 1434 may also include instructions that instruct processor 1430 to derive stitching data from the feedback signal TN and generate a map 1438 of the stitching data. For each stitching point, I/O circuit 1442 may continuously sample the feedback signal TN, and processor 1430 may filter out noise, and derive a thread tension measurement at a peak time. Processor 1430 may analyze the thread tension measurements and store results of the analysis in map 1438. Thus, the stitching data could include the thread tension measurements and/or an analysis of the thread tension measurement, such as an identification of defective stitches. The stitching data could further include time references of when the stitches were made. Among other things, the time references allow time-based video images of the stitches to be traced to their stitching points.

A video camera 1444 may take the time-based video images of the stitches. Knowing the reference time of a particular stitch, the video image of that stitch can be found. Processor 1430 may store the stitching data and the x- and y-coordinates of the stitching point at which the stitching data is derived.

In some embodiments, controller 1406 may include a display 1440 for displaying a graphical user interface (e.g., graphical user interface 1600 shown in FIG. 16). Graphical user interface 1600 may allow a user to adjust stitching parameters for thread patterns on a base layer. For example, graphical user interface 1600 may allow a user to adjust, among other things, polymer thread types, the overall denier of polymer and/or non-polymer threads, the denier of a core material for a polymer coated thread, stitching directions for patterns, the size and shape of areas to be stitched with thread sets, the size and shape of overlap areas between thread sets, the distance between stitch points in a polymer thread set, the oscillating pattern of a thread set, the start and end points of thread sets, and the distance between apexes in a thread set.

By adjusting parameters via graphical user interface 1600, patterned materials may be customized for an individual, or group of individuals, such as a group of individuals with the same gender, foot size, and/or foot width). In some embodiments, adjusting parameters for stitching parameters may include selecting a standard stitching pattern for a group of individuals (e.g., a group of individuals with a particular shoe size and/or width). In some embodiments, adjusting parameters for stitching parameters may include selecting a stitching pattern previously customized for an individual.

In some embodiments, the stitching pattern of one or more thread sets may be the only parameter altered between uppers for different individuals, or different groups of individuals, and may facilitate efficient customization of an upper. Altering stitch patterns may alter the degree of strength and/or stretchability in areas of an upper without having to change the thickness and/or material of a base material. For example, the distance between apexes in a polymer thread may be set to a smaller distance for a relatively heavy individual with a relatively large foot size compared to a relatively light individual with a relatively small foot size. A discussed above in regards to FIGS. 7A and 7B, a smaller distance between apexes in a thread set may increase the degree of directional strength provided by the thread set. As such, increased strength may be provided without having to change the thickness and/or material of a base layer. A manufacturing process that eliminates or reduces the need to change base materials for different individuals, or groups of individuals, may facilitate customization without increasing cost.

Is some embodiments, display 1440 may display a graphical representation of stitch patterns for one or more thread sets based on information entered into a graphical user interface. For examples, FIG. 15 shows a graphical representation 1500 of three thread sets patterned on a base material. Graphical representation 1500 may illustrate the shape of the areas stitched with the different thread sets and the stitch directions for the different thread sets.

In some embodiments, display 1440 may display a schematic (e.g., schematic 1700) of stitching patterns for one or more thread sets to be stitched on a base layer 1702. As shown for example in FIG. 17, schematic 1700 may illustrate the shape of base layer 1702, the shape of the areas stitched with the different thread sets (e.g., thread sets 1710, 1720, and 1730), the stitch directions for the different thread sets, and the start and end points for different thread sets.

Using a graphical user interface, such as graphical user interface 1600, a user may generate, or select stored, stitching patterns for a patterned material of an upper. FIG. 18 shows a patterned material 1800 according to some embodiments. Patterned material 1800 includes a base layer 1802 with a one or more polymer threads stitched to an outer surface 1804 base layer 1802. In some embodiments, outer surface 1804 with stitched polymer thread(s) may define at least a portion of an outermost surface of an upper (e.g., upper 102).

As shown in FIG. 18, patterned material 1800 may include a pattern 1810 for a portion of an upper (e.g., first portion 130 of upper 120) having a perimeter 1812 defining a shape for the portion of the upper. Pattern 1810 also includes (i) a first polymer thread set 1820 stitched in a first pattern on outer surface 1804 of base layer 1802, (ii) a second polymer thread set 1830 stitched in a second pattern on outer surface 1804 of base layer 1802, (iii) a third polymer thread set 1840 stitched in a third pattern on outer surface 1804 of base layer 1802, (iv) a fourth polymer thread set 1850 stitched in a fourth pattern on outer surface 1804 of base layer 1802, and (v) a fifth polymer thread set 1860 stitched in a fifth pattern on outer surface 1804 of base layer 1802.

Each thread set 1820/1830/1840/1850/1860 may impart a directional characteristic to a respective area of base layer 1802 as discussed herein. And areas of overlap between one or more the thread sets may impart composite characteristic(s) to respective areas of base layer 1802. In some embodiments, area(s) on patterned material 1800 may be devoid of a thread set to provide breathability.

As a non-limiting example, second polymer thread set 1830 may be stitched in a transverse direction between a medial side of pattern 1810 and a lateral side of pattern 1810 (e.g., transverse direction 402 in FIG. 4) on lateral and medial sides of pattern 1810 to provide directional strength in the transverse direction for an upper. Directional strength in the transverse direction imparted by second polymer thread set 1830 may provide a high degree of support and propulsion to areas on the lateral side and medial side of an upper (e.g., portions of toe box section 340, vamp section 330, and quarter sections 350 shown in FIG. 3). Such a pattern may be desirable for an athlete during high speed cutting and jumping activities (e.g., a basketball game, a football game, or a soccer match).

As another non-limiting example, fourth polymer thread set 1850 may be stitched in a longitudinal direction between a forefoot end of pattern 1810 and a heel end of pattern 1810 (e.g., longitudinal direction 400 in FIG. 4) in a forefoot portion of pattern 1810 to provide directional strength in the longitudinal direction for an upper. Directional strength in the longitudinal direction imparted by fourth polymer thread set 1850 may provide a high degree of support and propulsion for forefoot areas of an upper (e.g., toe box section 340 and portions of vamp section 330 shown in FIG. 3). Such a pattern may be desirable for an athlete during high speed cutting and jumping activities (e.g., a basketball game, a football game, or a soccer match).

FIG. 19 shows another patterned material 1900 according to some embodiments. Patterned material 1900 includes a base layer 1902 with a one or more polymer threads stitched to an outer surface 1904 base layer 1902. In some embodiments, outer surface 1904 with stitched polymer thread(s) may define at least a portion of an outermost surface of an upper (e.g., upper 102).

As shown in FIG. 19, patterned material 1900 may include a pattern 1910 for a portion of an upper (e.g., first portion 130 of upper 120) having a perimeter 1912 defining a shape for the portion of the upper. Pattern 1910 also includes (i) a first polymer thread set 1920 stitched in a first pattern on outer surface 1904 of base layer 1902, (ii) a second polymer thread set 1930 stitched in a second pattern on outer surface 1904 of base layer 1902, (iii) a third polymer thread set 1940 stitched in a third pattern on outer surface 1904 of base layer 1902.

Each thread set 1920/1930/1940 may impart a directional characteristic to a respective area of base layer 1902 as discussed herein. And areas of overlap between one or more the thread sets may impart composite characteristic(s) to respective areas of base layer 1902. In some embodiments, as shown in FIG. 19, pattern 1910 may include eyelet blanks 1950 with eyelets 1952. In some embodiments, area(s) on patterned material 1900 may be devoid of a thread set to provide breathability.

As a non-limiting example, first polymer thread set 1920 may be stitched in a direction approximately 45 degrees relative to a transverse direction between a medial side of pattern 1910 and a lateral side of pattern 1910 (e.g., 45 degrees relative transverse direction 402 in FIG. 4) to provide directional strength and stretchability in the transverse direction for an upper. The directional strength in the transverse direction imparted by first polymer thread set 1920 may provide support and propulsion to areas on the lateral side and medial side of an upper (e.g., portions of toe box section 340, vamp section 330, and quarter sections 350 shown in FIG. 3) while also allowing these areas to stretch in the transverse direction. Such a pattern may be desirable for an athlete during extended periods of aerobic activity (e.g., a marathon or a long jog) because it may provide desired support, propulsion, and comfort for the athlete.

Returning to FIG. 13, in some embodiments, stitching polymer thread(s) in one or more partners on a base layer in step 1302 may include collecting a biometric data profile for an individual (e.g., individual 2000 shown in FIG. 20), or group of individuals. In some embodiments, a biometric data profile may be collected using a physiological and personal characteristic collection and analysis system, such as a Run Genie® system. In some embodiments, the biometric data profile may be collected using the data collection and analysis system described in U.S. patent application Ser. No. 14/579,226, filed on Dec. 22, 2014 and published as US 2016/0180440, which is hereby incorporated by reference in its entirety by reference thereto. In some embodiments, a biometric data profile may include data related to an individual's gait collected using a Vicon® Motion Capture System with force plates. In some embodiments, biometric data may include strain data for an article of footwear collected using an Aramis system from GOM mbH.

The physiological characteristics collected may in step 1302 may include, but are not limited to, gait characteristics, such as foot strike type (e.g. heel, midfoot, forefoot, etc.), rate of pronation or supination, and degree of pronation and supination. In some embodiments, step 1302 may include receiving personal information about the individual before or after receiving physiological characteristics data about the individual. Personal information may include information such as the individual's name, prior injury information, height, weight, gender, shoe size, an athletic goal, intended athletic environment or terrain, intended athletic activity duration, intended athletic activity frequency, intended athletic activity distance, quantitative or qualitative preferences about athletic equipment or footwear (such as level of cushion, preference of weight, materials and the like), and current athletic footwear.

In some embodiments, step 1302 may include receiving biometric data via a local wired or wireless connection. In some embodiments step 1302 may include monitoring individual 2000 in real time during an athletic activity, such as jogging.

Physiological characteristics may be collected using one or more sensor modules 2002. A sensor module 2002 may include one or more sensors, and may be physically coupled to an object (e.g., article of footwear 2004) during an everyday or athletic activity conducted by individual 2000. A sensor module 2002 may be used to monitor changes in the spatial orientation of an individual's body or a piece of the individual's athletic equipment or article of footwear in some embodiments. Sensor module 2002 may be used in combination with predetermined correlation data stored in a data structure to determine a correlation between body or equipment or article of footwear movement data and a characteristic such as a gait characteristic in some embodiments.

In some embodiments, a sensor module 2002 is placed and/or built into article of footwear 2004 to measure, for example, a runner's running form and gait cycle (e.g., sensor is placed on, removably attached to, or built into the heel, midsole, or toe of article of footwear 2004). Additional sensors/motion monitors can also be placed on the runner's knee and hip, for example, to obtain more information about the runner's running form.

Sensor module 2002 may include a plurality of sensors, including but not limited to, one or more motion sensors, such as acceleration sensors and magnetic field sensors, or angular momentum sensors. In some embodiments, sensor module 2002 may include one or more temperature sensors, a heart rate monitoring device, a pedometer, and/or an accelerometer-based monitoring device. Sensors of sensor module 2002 may be capable of measuring a variety of athletic performance parameters. The term "performance parameters" may include physical parameters and/or physiological parameters associated with the individual's 2000 athletic activity. Physical parameters measured may include, but are not limited to, time, distance, speed, pace, pedal count, wheel rotation count, rotation generally, stride count, stride length, airtime, stride rate, altitude, temperature, strain, impact force, jump force, force generally, and jump height. Physiological parameters measured may include, but are not limited to, heart rate, respiration rate, blood oxygen level, blood lactate level, blood flow, hydration level, calories burned, or body temperature.

An acceleration sensor may be adapted to measure the acceleration of the sensor module 2002. Accordingly, when the sensor module 2002 is physically coupled to an object (such as an individual's 2000 body, article of footwear 2004, or other a piece of athletic equipment), the acceleration sensor may be capable of measuring the acceleration of the object, including the acceleration due to the earth's gravitational field. In some embodiments, an acceleration sensor may include a tri-axial accelerometer that is capable of measuring acceleration in three orthogonal directions. In some embodiments one, two, three, or more separate accelerometers may be used.

A magnetic field sensor may be adapted to measure the strength and direction of magnetic fields in the vicinity of sensor module 2002. Accordingly, when sensor module 2002 is physically coupled to an object (such as an individual's 2000 body, article of footwear 2004, or other a piece of athletic equipment), a magnetic field sensor may be capable of measuring the strength and direction of magnetic fields in the vicinity of the object, including the earth's magnetic field. In some embodiments, a magnetic field sensor may be a vector magnetometer. In some embodiments, a magnetic field sensor may be a tri-axial magnetometer that is capable of measuring the magnitude and direction of a resultant magnetic vector for the total local magnetic field in three dimensions. In some embodiments one, two, three, or more separate magnetometers may be used.

In some embodiments, an acceleration sensor and a magnetic field sensor may be contained within a single accelerometer-magnetometer module bearing model number LSM303DLHC made by STMicroelectronics of Geneva, Switzerland.

An angular momentum sensor, which may be, for example, a gyroscope, may be adapted to measure the angular momentum or orientation of sensor module 2002. Accordingly, when the sensor module 2002 is physically coupled to an object (such as an individual's 2000 body, article of footwear 2004, or other athletic equipment), the angular momentum sensor may be capable of measuring the angular momentum or orientation of the object. In some embodiments, an angular momentum sensor may be a tri-axial gyroscope that is capable of measuring angular rotation about three orthogonal axes. In some embodiments one, two, three, or more separate gyroscopes may be used. In some embodiments, angular momentum sensor may be used to calibrate measurements made by one or more of an acceleration sensor and a magnetic field sensor.

A heart rate sensor may be adapted to measure individual's 2000 heart rate. A heart rate sensor may be placed in contact with the individual's 2000 skin, such as the skin of the individual's chest, and secured with a strap. A heart rate sensor may be capable of reading the electrical activity the individual's 2000 heart.

A temperature sensor may be, for example, a thermometer, a thermistor, or a thermocouple that measures changes in the temperature. In some embodiments, a temperature sensor may primarily be used for calibration other sensors, such as, for example, an acceleration sensor and a magnetic field sensor.

In some embodiments, sensor module 2002 may include a position receiver, such as an electronic satellite position receiver that is capable of determining its location (i.e., longitude, latitude, and altitude) using time signals transmitted along a line-of-sight by radio from satellite position system satellites. Known satellite position systems include the GPS system, the Galileo system, the BeiDou system, and the GLONASS system. In some embodiments, a position receiver may be an antenna that is capable of communicating with local or remote base stations or radio transmission transceivers such that the location of sensor module 2002 may be determined using radio signal triangulation or other similar principles. In some embodiments, position receiver data may allow sensor module 2002 to detect information that may be used to measure and/or calculate position waypoints, time, location, distance traveled, speed, pace, or altitude.

Data collected by sensor module 2002 may classify individuals based on their running style, utilizing data analysis such as an anterior-posterior plot angle vs. time; medial-lateral plot angle vs. time; and the like. Calculations of these characteristic may be used to group individuals into different categories (groups), such as a heel striker, a midfoot striker, a forefoot striker, a pronator, supinator, a neutral individual, or some combination of characteristics. In some embodiments, gait analysis may utilize personal information of individual 2000, such a gender, shoe size, height, weight, running habits, and prior injuries.

In some embodiments, a regression analysis can be used to determine gait characteristics such as foot strike type, rate of pronation, degree of pronation, and the like based on acceleration data obtained from sensor module 2002. In some embodiments, the regression analysis can be used to determine gait characteristics such as foot strike type, rate of pronation, degree of pronation, and the like based on other data such as magnetometer data, angular momentum sensor data, or multiple types of data. In some embodiments, the analysis can include other user-input information such as prior injury information, an athletic goal, intended athletic environment or terrain, intended athletic duration, and current athletic footwear.

Athletic goals may be, for example, training for a race, to stay healthy, to lose weight, and training for sports. Other examples of athletic goals may include training for a race, or other sporting event, improving individual fitness, simply enjoy running, or the like. Frequency intervals may include for example about 1 to 2 times per week, about 3 to 4 times per week, about 5 to 7 times per week, or the individual doesn't know. Length intervals may include for example about less than about 5 miles per week, about 5 to 10 miles per week, about 10 to 20 miles per week, greater than about 20 miles per week, or the individual doesn't know. Examples of intended athletic terrain environments may include roads, track, treadmill, trail, gym, or particular athletic fields designed for a specific sport. Examples of athletic equipment preferences may include for example more cushioning, less weight, better fit, strength, durability, intended athletic activity range, balance, weight balance, more color choices, and the like.

In some embodiments, collecting a biometric data profile in step 1302 may include obtaining previously collected and stored data for an individual. In some embodiments, collecting biometric data may include obtaining a standard biometric data profile for a group of individuals. For example, a standard profile for individuals having a certain shoe size, weight, height, arch shape, stability characteristic, and/or touchdown characteristic may be retrieved in step 1302.

Biometric data may be used to generate stitch patterns (e.g., stitch pattern 1810, stitch pattern 1910, or the pattern for any other thread set discussed herein) for a patterned material. Parameters of a stitch pattern or thread set that may be customized to an individual's, or group of individuals' needs include, but are not limited to: (i) polymer thread types, (ii) stitching directions for patterns/polymer thread sets, (iii) the size and shape of areas to be stitched with thread sets, (iv) the size and shape of overlap areas between thread sets, (v) the distance between stitch points in a polymer thread set, (vi) the oscillating pattern of a thread set, (vii) the distance between apexes in a thread set, (viii) the overall denier of polymer or non-polymer threads in a thread set, (ix) the denier of a core material for a polymer coated thread. Parameters (i)-(ix) may vary between different areas or portions of an upper (e.g., forefoot portion 110, a midfoot portion 112, and a heel portion 114) to provide targeted characteristics in different areas or portions of an upper based on an individual's needs.

As a non-limiting example, the distance between apexes in first polymer thread set 1920 shown in FIG. 19 may be smaller for a relatively heavy individual with a relatively large foot size compared to a relatively light individual with a relatively small foot size. A discussed above in regards to FIGS. 7A and 7B, a smaller distance between apexes in a thread set may increase the degree of directional strength provided by the thread set. This may be desirable for a heavy/large-footed because such an individual will likely apply larger forces to an upper during use.

As another non-limiting example, the stitching direction for first polymer thread set 1920 in FIG. 19 may be at a smaller angle relative to transverse direction 402 for a relatively heavy individual with a relatively large foot size compared to a relatively light individual with a relatively small foot size. For example, first polymer thread set 1920 may have a stitching angle of 35 degrees relative to transverse direction 402 for a heavy/large-footed individual compared to a stitching angle of 45 degrees for a light/small-footed individual. A 35 degree stitching angle may provide a higher degree of direction strength in transverse direction 402 compared to a 45 degree stitching direction angle. This may be desirable for a heavy/large-footed because such an individual will likely apply larger lateral forces to an upper during use (e.g., during cutting). Other parameters of stitch patterns may be tailored in similar fashions based on a biometric data profile for an individual, or group of individuals.

In some embodiments, parameters (i)-(ix) may be tailored to a particular individual's foot or gait, or a particular group of individuals' feet or gait. This customization may be based on unique user characteristics provided by, for example, a Run Genie® system. In some embodiments, parameters (i)-(ix) may be customized for an individual to modify an irregularity in the individual's gait. In such embodiments, an upper may provide stability and/or propulsion characteristics to modify the individual's gait (i.e., modify his or her gait to a preferred motion). Correcting/modifying an individual's gait to preferred motion may reduce discomfort for an individual during exercise.

In some embodiments, a patterned material for an upper may be customized to the individual characteristics of the musculoskeletal system of an individual, or group of individuals, and/or to the movements and forces the musculoskeletal system is subject to during movement of the individual, or group of individuals, for example, during a gait cycle. The independent movement of the upper may allow the upper to remain in close proximity to the foot of an individual whilst the individual is moving. This close proximity of the upper to the foot of the individual may support or stimulate the musculoskeletal system so that the system is better equipped to handle the forces acting, for example, through stimulating the arch of the foot to engage the onward postural chain to avoid possible negative effects, for example, arch collapse, thus, increasing the stability of the foot and musculoskeletal system of the wearer.

In some embodiments, thread patterns may be tailored for or an individual, or group of individuals, based on the musculoskeletal system of the individual, or group of individuals, and/or to the movements and forces the musculoskeletal system is subject to during movement of the individual, or group of individuals, for example, during a gait cycle. In some embodiments, parameters (i)-(ix) may be tailored based on a musculoskeletal system. In some embodiments, parameters (i)-(ix) may be tailored to allow a minimum or maximum strain percentage in areas on an upper. For example, parameters (i)-(ix) may be tailored to allow a minimum stain of 5% in both the medial-lateral direction and forefoot-to-rearfoot direction (also called the anterior-to-posterior direction). The allowed minimum strain may also be 10% or 15% or 20% or 30% or 50%. In the midfoot region where an individual's arch is located an upper may be configured to allow a maximum strain of 150% in both the medial-lateral direction and forefoot-to-rearfoot direction. The allowed maximum strain may also be 125% or 110% or 100% or 80%.

The strain may in part include a strain imparted to the upper during manufacture of the upper. The strain may in part be imparted when the user inserts their foot into the upper. The strain may be imparted during use of the shoe by the wearer.

In some embodiments, strain percentages may be analyzed using an Aramis system from GOM mbH. The system is a calibrated digital image correlation (DIC) device which allows for dynamic real time surface strain measurement. Based on strain data collected by the Aramis system, thread patterns may be tailored to provide desired strain percentages to areas of an upper.

In some embodiments, controller 1406 may be configured to automatically generate thread pattern(s) for a patterned material based on biometric data. In some embodiments, controller 1406 may be configured to automatically generate thread patterns based data collected using an Aramis system from GOM mbH. In some embodiments, controller 1406 may store command algorithms configured to tailor a given thread pattern based on the needs of an individual, or group of individuals. For example, controller 1406 may tailor a given thread pattern for different foot sizes, foot widths, and/or gait types based on a command algorithm generated based on data collected by the Aramis system.

After stitching one or more polymer threads to a base layer in one or more patterns in step 1302, the one or more polymer threads may be bonded to the base layer in step 1304. In some embodiments, the polymer material(s) of polymer thread(s) may be bonded to the base layer by heating the polymer material(s) to a minimum temperature to cause the polymer material(s) to bond with the base layer. In some embodiments, the polymer material(s) of polymer thread(s) in one or more thread sets (e.g., thread sets 910, 920, and/or 930) may be bonded be bonded to each other by heating the polymer material(s) to a minimum temperature to cause the polymer material(s) of the thread sets to bond together (e.g., fuse together at fuse points).

In some embodiments, the polymer material(s) of polymer thread(s) may be bonded to the base layer and/or each other using infra-red or ultraviolet light (e.g., for polymer thread(s) including a photo-reactive polymeric material. In some embodiments, the polymer material(s) of polymer thread(s) may be bonded to the base layer and/or each other by a chemical melt process. In some embodiments, the polymer material(s) of polymer thread(s) may be bonded to the base layer and/or each other in a solvent bonding process (e.g., for polymer thread(s) including a water soluble polymeric material).

In some embodiments, one or more polymer thread sets may be bonded to base layer with pressure and heat. In some embodiments, polymer thread(s) may be bonded to a base layer using a heat press (e.g., heat press 2200). In some embodiments, polymer thread(s) may be bonded to a base layer using a mold (e.g., mold 2100) in a thermoforming process. In step 1304, the amount of heat applied to different areas and/or different portions of different areas on a base layer may be tailored to create a desired about of bonding in those areas.

In some embodiments, heat and pressure may be applied to a patterned material at a predetermined temperature and a predetermined pressure for a predetermined time period to form one or more portions that are partially bonded (fused). At least one of the predetermined temperature, the predetermined pressure, and the predetermined time period may be selected based on a characteristic of the patterned material such that, after applying heat and pressure to the patterned material, a portion of the patterned material includes thread(s) that are bonded (fused) to a base layer and/or each other. Applying heat and pressuring to the patterned material can occur substantially simultaneously. In the context of this application, "fused" means polymer thread lines that are joined to a base layer and/or each other by melting.

In some embodiments, a patterned material, or portion thereof, may be embossed when bonding polymer thread(s) to a base layer. In some embodiments, an embossed patterned material may include a plurality of substantially linear ribs having a semi-circular cross-sectional shape. In some embodiments, an embossed patterned material may include non-linear ribs, ribs with other cross-sectional shapes, and/or ribs that are part of a non-repeating or irregular pattern. Embossing portions of a patterned material may provide additional structural support for an upper. Additionally, embossing can be used to provide three-dimensional aesthetic designs for an upper.

In some embodiments, at least one of the predetermined temperature, the predetermined pressure, and the predetermined time period of a bonding process may be selected based on characteristics of the materials of patterned material. Exemplary characteristics include the base layer construction type (e.g., woven, knitted, braided, netted, felted, plaited, single layer, multiple layer, etc.), thread construction type (e.g., cabled thread, core thread, coated thread, etc.), thread weight (e.g., Denier), the color of the filaments forming the thread, material content of the thread and/or base layer (e.g., polyester, nylon, thermoplastic polyurethane).

FIGS. 21A-21C show an exemplary process for three-dimensionally thermo-molding polymer thread(s) to a base layer to form all or a portion of an upper (e.g., upper 120) according to some embodiments. As shown, in FIGS. 21A and 21B, a mold 2100 may be assembled around a skin 2110 on an inflatable bladder 2120 (i.e., skin 2110 and inflatable bladder 2120 may be inserted into the mold cavity of mold 2100). Skin 2120 may be a patterned material including a base layer 2114 having one or more thread sets 2112 stitched in one or more patterns on a surface of base layer 2114. Base layer 2114 and thread sets 2112 may be the same as or similar to base layers and thread sets discussed herein (e.g., base layer 602 and thread sets 610/620/630 as discussed in regards to FIG. 6).

In some embodiments, base layer 2114 may be a single, continuous piece of material disposed over inflatable bladder 2120. In some embodiments, base layer 2114 may include a plurality of layers stacked vertically and/or arranged side-by-side. In some embodiments, the plurality of layers stacked vertically and/or arranged side-by-side may be joined together (e.g., via stitching seam(s) with polymer thread(s) or non-polymer thread(s)). In some embodiments, the plurality of layers stacked vertically and/or arranged side-by-side may be joined together via one or more thread sets 2112. Joining layers of base layer 2114 together may allow multiple layers of base layer 2114 to be arranged prior to thermo-molding. Further, any seams created when joining layers of base layer 2114 may be concealed by thread sets 2112 stitched and/or bonded over the seams of base layer 2114.

In some embodiments, a connector 2122 may be coupled to inflatable bladder 2120. Connector 2122 may include a first end coupled to inflatable bladder 2120 and a second end configured to couple with a pressure conduit for delivering pressurized air 2124 from a pressure source. In some embodiments, connector 2122 may include a pressure valve for regulating the pressure of pressurized air 2124 pumped into inflatable bladder 2120.

In some embodiments, the mold cavity of mold 2100 and/or skin 2110 may be coated with a non-stick material, such as but not limited to a silicone spray, to reduce potential adhesion between skin 2110 and the mold cavity during forming. Before or after skin 2110 and inflatable bladder 2120 are inserted into the mold cavity, mold 2100 may be heated to a predetermined temperature. The temperature of mold 2100 may be such that it softens the base layer and/or the polymer thread(s) of skin 2110 to allow the polymer thread(s) to bond to base layer and/or to each other. In some embodiments, skin 2100 may take on the shape of an upper for an article of footwear in mold 2100.

In some embodiments, the predetermined temperature may be equal to or above the melting point of polymeric material(s) of skin 2110 (e.g., the thermoplastic polymer(s) of polymer thread(s)). In some embodiments, the predetermined temperature may be below the melting point of polymeric material(s) of skin 2110 (e.g., the thermoplastic polymer(s) of polymer thread(s)), but high enough to cause the polymeric material(s) to bond (fuse) together. In some embodiments, the predetermined temperature may be 180 degrees C. or less. In some embodiments, the predetermined temperature may be in the range of 180 degrees C. to 80 degrees C. In some embodiments, the predetermined temperature may be 160 degrees C. or less. In some embodiments, the predetermined temperature may be in the range of 160 degrees C. to 65 degrees C. In some embodiments, the predetermined temperature may be selected such that polymeric material(s) of skin 2110 undergo no chemical reactions during thermo-forming an upper. Heat may be applied to mold 2100 in one or more ways, such as but not limited to, radio frequency heating, high frequency heating, infrared heating, and, convective heating.

In some embodiments, the polymer thread(s) of skin 2100 may be bonded to base layer 2114 and/or each other at a temperature that creates little to no volatile substances (e.g., vapors created by chemical reactions such as those created during curing of a polymer). In some embodiments, the bonding of polymer thread(s) of skin 2100 may not cause a change in the chemical composition of the polymeric material(s) of the polymer thread(s). The use of low processing temperatures may reduce manufacturing cost and may reduce environmental impact of a manufacturing process by reducing the release of volatile substances. Further, a manufacturing process that does not rely on the occurrence of chemical reactions may result in a manufacturing process that is easier to control and reproduce. In some embodiments, the temperature used to bond polymer thread(s) of skin 1212 may be greater than the softening point temperature of the polymeric material(s) of the polymer thread(s). The softening point temperature of a polymer may be measured using a Vicat softening point test.

In some embodiments, after heating mold 2100, inflatable bladder 2120 may be expanded to press skin 2110 into contact with the interior surface of the mold cavity defined by a medial mold plate 2102 and lateral mold plate 2104 of mold 2100. This combination of pressure and heat will cause skin 2110 to take on the shape of the interior surface of the mold cavity, thereby taking on the shape of an upper for an article of footwear. In some embodiments, skin 2110 may be pressed against the interior surface of a mold cavity at the predetermined temperature for 30 seconds to 180 seconds at a pressure in the range of 5 g/cm$^2$ to 7 g/cm$^2$.

The mold cavity of mold 2100 may be sized and shaped for a particular foot type and size (i.e., length and width). In some embodiments, the mold 2100 may be a customized mold including a customized interior mold cavity surface. In some embodiments, mold 2100 may be customized for a particular individual. In some embodiments, mold 2100 may include a mold cavity created by digitally scanning a human foot. In some embodiments, mold 2100 may include a customized mold cavity created by digitally scanning an individual's foot. In some embodiments, an individual's foot may be scanned using a CREAFORM Go!SCAN 3D scanner, Serial No: 570489, manufactured by Ametek Ultra Precision Technologies.

When bonding polymer thread(s) to a base layer to thermo-form uppers for footwear as discussed herein, only mold(s) 2100 may need to be interchanged to form different sizes, shapes, and/or types of uppers. The interchangeability and modularity of molds may reduce manufacturing costs by reducing the number of parts that need to changed/adjusted when forming uppers for different articles of footwear. Reducing the parts that need to changed/adjusted when forming uppers for different articles of footwear may facilitate the use of an automated process for thermo-forming uppers for articles of footwear. Further, it may facilitate cost-effective manufacturing of customized uppers.

As shown for example in FIG. 21C, after polymer thread(s) of skin 2100 are bonded to a base layer, after portions of polymer thread sets are bonded together in areas of overlap, and/or after skin 2100 takes on the shape of the mold cavity defined medial mold plate 2102 and lateral mold plate 2104, inflatable bladder 2120 may be deflated and an upper 2130 may be removed from the mold cavity. In some embodiments, excess material may be removed (e.g., cut) from upper 2130 to define the edges of upper 2130. In some embodiments, thermoforming an upper may be include a thermoforming process as discussed in U.S. application Ser. Nos. 15/156,062 and 15/156,104, both filed on May 16, 2016, which are hereby incorporated in their entirety by reference thereto.

FIG. 22 shows a heat press 2200 according to some embodiments. Heat press 2200 may apply pressure and heat to patterned material (e.g., patterned materials 900, 1800, or 1900) to bond polymer thread(s) of one or more polymer thread sets to a base layer and/or bond portions of polymer thread sets in areas of overlap between the thread sets (compare FIG. 9A to FIG. 11A). In some embodiments, heat press 2220 may provide heat at a predetermined temperature equal to or above the melting point of polymeric material(s) of a patterned material (e.g., the thermoplastic polymer(s) of polymer thread(s)). In some embodiments, heat press 2220 may provide heat at a predetermined temperature below the melting point of polymeric material(s) of a patterned material (e.g., the thermoplastic polymer(s) of polymer thread(s)), but high enough to cause the polymeric material(s) to bond (fuse) together.

The temperature used to bonded polymer thread(s) with heat press 2220 may be the same as or similar to the temperatures discussed herein for three-dimensionally thermo-molding a patterned material. In some embodiments, the predetermined temperature may be 180 degrees C. or less. In some embodiments, the predetermined temperature may be in the range of 180 degrees C. to 80 degrees C. In some embodiments, the predetermined temperature may be 160 degrees C. or less. In some embodiments, the predetermined temperature may be in the range of 160 degrees C. to 65 degrees C. In some embodiments, the predetermined temperature may be selected such that polymeric material(s) of a patterned material undergo no chemical reactions during heating. In some embodiments, the patterned material may be pressed in heat press 2200 at the predetermined temperature for 30 seconds to 180 seconds at a pressure in the range of 5 g/cm² to 7 g/cm².

Heat may be applied to a patterned material in heat press 2220 in one or more ways, such as but not limited to, radio frequency heat sealing (welding), high frequency heat sealing (welding), infra-red welding, convective heating, and steaming. In some embodiments, heat may be applied to a single outer surface of a patterned material (e.g., top surface 904 in FIG. 9) in heat press 2220. In some embodiments, heat may be applied to both outer surfaces of a patterned material (e.g., top surface 904 and bottom surface 906 in FIG. 9) in heat press 2220. In some embodiments, after heat pressing a patterned material, excess material may be removed (e.g., cut) from the patterned material to define the edges of the patterned material.

FIGS. 23A and 23B show base materials with various polymer thread patterns stitched and bonded with a heat press on a base layer according to various embodiments. FIG. 23A shows a patterned material 2300 including a base layer 2310 with a plurality of polymer thread patterns 2330 stitched and bonded to base layer 2310. Similarly, FIG. 23B shows a patterned material 2350 including a base layer 2360 with a plurality of polymer thread patterns 2370 stitched and bonded to base layer 2360.

Thread patterns 2320 and 2370 include a plurality of overlapping thread sets configured to impart a composite characteristic to respective areas on base layers 2310 and 2360. The relative stitch directions of overlapping thread sets in thread patterns 2330 and 2370 may be tailored to impart desired composite characteristics to areas on base layers 2310 and 2360. By changing the angle of overlap between thread sets, the degree of stretch and strength in areas on base layers 2310 and 2370 may change to provide desired composite stretch and/or strength characteristics.

After bonding one or more polymer threads in step 1304, the base layer may be coupled to one or more footwear components to form an article of footwear in step 1306. The base layer may be coupled to one or more footwear components by, for example, stitching or adhesively bonding the base material to one or more a footwear components. Footwear components include, but are not limited to a heel counter (e.g., heel counter 162), a sole (e.g., sole 180), and a lace component (e.g., lace component 320).

In some embodiments, polymer thread(s) may be stitched to a base layer to form an article of apparel. FIGS. 24A and 24B show the front (FIG. 24A) and back (FIG. 24B) of an article of apparel (shirt 2400) according to an embodiment. Shirt 2400 includes a body 2402 and sleeves 2404. In some embodiments, the entire shirt 2400 may be manufactured using a patterned material as discussed herein. In some embodiments, a portion of shirt 2400, for example body 2402, may be manufactured using one or more patterned materials as discussed herein. Different zones (e.g., zones 2410, 2412, and 2414) located on shirt 2400 may be stitched with various polymer thread sets to impart directional and composite characteristics as discussed herein. Accordingly, different zones may be configured to provide among other things, varying degrees of strength, breathability, and insulation. Different zones may be created by varying the parameters of one or more thread sets as discussed herein, by overlapping one or more thread sets, and/or by using different thread materials in each zone. The number and configuration of zones on shirt 2400 may be determined by studying different physiological processes of the human body as discussed in U.S. patent application Ser. No. 12/926,051, filed on Oct. 22, 2010, now U.S. Pat. No. 8,910,313, the disclosure of which is incorporated by reference herein in its entirety.

As a non-limiting example, shirt 2400 may include at least a first zone 2410, a second zone 2412, and a third zone 2414 as shown in FIGS. 24A and 24B. First zone 2410, second zone 2412, and third zone 2414 may include different thread sets to provide varying degrees of strength, breathability, and insulation to shirt 2400. As a non-limiting example, first zone 2410, which is located on the shoulders of an individual, may include thread sets configured to provide a large degree of breathability, which may help keep an individual cool during an athletic activity. The number, location, and configuration of zones may be dependent on one or more of the following: the gender for which shirt 2400 is designed, whether shirt 2400 is a warm weather shirt or a cold weather shirt, and whether shirt 2400 is intended to be used indoors or outdoors.

While FIGS. 24A and 24B shows shirt 2400 as an exemplary article of apparel, any article of apparel, or a portion thereof, may be manufactured using the multilayer fabrics discussed herein. Such articles of apparel may be, but are not limited to, pants, shorts, leggings, a sock a jacket, a coat, a hat, a sleeve, a shoe, a sweater, a jersey, and a glove.

One or more aspects of the methods of manufacturing a midsole for an article of footwear discussed herein, or any part(s) or function(s) thereof, may be implemented using hardware, software modules, firmware, tangible computer readable media having instructions stored thereon, or a combination thereof and may be implemented in one or more computer systems or other processing systems.

FIG. 25 illustrates an exemplary computer system 2500 in which embodiments, or portions thereof, may be implemented as computer-readable code. For example, aspects of the methods discussed herein that may be implemented in one or more computer systems include, but are not limited to, collecting a biometric data profile, generating polymer thread patterns based on the biometric data profile, and obtaining an already generated polymer thread pattern (or patterns) may be implemented in computer system 2500 using hardware, software, firmware, tangible computer readable media having instructions stored thereon, or a combination thereof and may be implemented in one or more computer systems or other processing systems.

If programmable logic is used, such logic may execute on a commercially available processing platform or a special purpose device. One of ordinary skill in the art may appreciate that embodiments of the disclosed subject matter can be practiced with various computer system configurations, including multi-core multiprocessor systems, minicomputers, and mainframe computers, computer linked or clustered with distributed functions, as well as pervasive or miniature computers that may be embedded into virtually any device.

For instance, at least one processor device and a memory may be used to implement the above described embodiments. A processor device may be a single processor, a plurality of processors, or combinations thereof. Processor devices may have one or more processor "cores."

Various embodiments of the inventions may be implemented in terms of this example computer system 2500. After reading this description, it will become apparent to a person skilled in the relevant art how to implement one or more of the inventions using other computer systems and/or computer architectures. Although operations may be described as a sequential process, some of the operations may in fact be performed in parallel, concurrently, and/or in a distributed environment, and with program code stored locally or remotely for access by single or multi-processor machines. In addition, in some embodiments the order of operations may be rearranged without departing from the spirit of the disclosed subject matter.

Processor device 2504 may be a special purpose or a general purpose processor device. As will be appreciated by persons skilled in the relevant art, processor device 2504 may also be a single processor in a multi-core/multiprocessor system, such system operating alone, or in a cluster of computing devices operating in a cluster or server farm. Processor device 2504 is connected to a communication infrastructure 2506, for example, a bus, message queue, network, or multi-core message-passing scheme.

Computer system 2500 also includes a main memory 2508, for example, random access memory (RAM), and may also include a secondary memory 2510. Secondary memory 2510 may include, for example, a hard disk drive 2512, or removable storage drive 2514. Removable storage drive 2514 may include a floppy disk drive, a magnetic tape drive, an optical disk drive, a flash memory, a Universal Serial Bus (USB) drive, or the like. The removable storage drive 2514 reads from and/or writes to a removable storage unit 2518 in a well-known manner. Removable storage unit 2518 may include a floppy disk, magnetic tape, optical disk, etc. which is read by and written to by removable storage drive 2514. As will be appreciated by persons skilled in the relevant art, removable storage unit 2518 includes a computer usable storage medium having stored therein computer software and/or data.

Computer system 2500 (optionally) includes a display interface 2502 (which can include input and output devices such as keyboards, mice, etc.) that forwards graphics, text, and other data from communication infrastructure 2506 (or from a frame buffer not shown) for display on display unit 2530.

In alternative implementations, secondary memory 2510 may include other similar means for allowing computer programs or other instructions to be loaded into computer system 2500. Such means may include, for example, a removable storage unit 2522 and an interface 2520. Examples of such means may include a program cartridge and cartridge interface (such as that found in video game devices), a removable memory chip (such as an EPROM, or PROM) and associated socket, and other removable storage units 2522 and interfaces 2520 which allow software and data to be transferred from the removable storage unit 2522 to computer system 2500.

Computer system 2500 may also include a communication interface 2524. Communication interface 2524 allows software and data to be transferred between computer system 2500 and external devices. Communication interface 2524 may include a modem, a network interface (such as an Ethernet card), a communication port, a PCMCIA slot and card, or the like. Software and data transferred via communication interface 2524 may be in the form of signals, which may be electronic, electromagnetic, optical, or other signals capable of being received by communication interface 2524. These signals may be provided to communication interface 2524 via a communication path 2526. Communication path 2526 carries signals and may be implemented using wire or cable, fiber optics, a phone line, a cellular phone link, an RF link or other communication channels.

In this document, the terms "computer program medium" and "computer usable medium" are used to generally refer to media such as removable storage unit 2518, removable storage unit 2522, and a hard disk installed in hard disk drive

2512. Computer program medium and computer usable medium may also refer to memories, such as main memory 2508 and secondary memory 2510, which may be memory semiconductors (e.g. DRAMs, etc.).

Computer programs (also called computer control logic) are stored in main memory 2508 and/or secondary memory 2510. Computer programs may also be received via communication interface 2524. Such computer programs, when executed, enable computer system 2500 to implement the embodiments as discussed herein. In particular, the computer programs, when executed, enable processor device 2504 to implement the processes of the embodiments discussed here. Accordingly, such computer programs represent controllers of the computer system 2500. Where the embodiments are implemented using software, the software may be stored in a computer program product and loaded into computer system 2500 using removable storage drive 2514, interface 2520, and hard disk drive 2512, or communication interface 2524.

Embodiments of the inventions also may be directed to computer program products comprising software stored on any computer useable medium. Such software, when executed in one or more data processing device, causes a data processing device(s) to operate as described herein. Embodiments of the inventions may employ any computer useable or readable medium. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, and optical storage devices, MEMS, nanotechnological storage device, etc.).

Some embodiments may be directed to an upper for an article of footwear, the upper including a base layer defining at least a portion of the upper and one or more polymer threads stitched to the base layer, the one or more polymer threads having a core including a first material and a coating including a second material where the melting point of the first material is higher than the melting point of the second material; where the one or more polymer threads include a first polymer thread set stitched in a first pattern on an outer surface of the base layer, the first pattern including polymer thread lines oriented in a first direction, and a second polymer thread set stitched in a second pattern on the outer surface of the base layer, the second pattern including polymer thread lines oriented in a second direction different from the first direction; where at least a portion of the first polymer thread set overlaps at least a portion of the second polymer thread set in an overlap area; and where at least a portion of the first polymer thread set is bonded to the base layer in the overlap area via the coating of the polymer thread in the first polymer thread set.

In any of the various embodiments discussed herein, at least a portion of the second polymer thread set may be bonded to a base layer in an overlap area via a coating of the polymer thread in the second polymer thread set.

In any of the various embodiments discussed herein, at least a portion of the first polymer thread set and at least a portion of the second polymer thread set that overlap may be bonded to each other via coatings of the polymer thread in the first polymer thread set and the polymer thread in the second polymer thread set.

In any of the various embodiments discussed herein, the thread lines of the first pattern may be oriented at a first angle relative to a mid-line of an upper between a forefoot end of the upper and a heel end of the upper. In some embodiments, the thread lines of the second pattern may be oriented at a second angle relative to the mid-line, the second angle being different from the first angle.

In any of the various embodiments discussed herein, the first pattern may impart a first directional characteristic to a first area of an upper. In some embodiments, the second pattern may impart a second directional characteristic to a second area of the upper. In any of the various embodiments discussed herein, the first directional characteristic and the second directional characteristic may be selected from the group of: directional stretchability and directional strength.

In any of the various embodiments discussed herein, the first pattern and the second pattern may impart a composite characteristic to an overlap area between the first pattern and the second pattern on an upper. In any of the various embodiments discussed herein, the composite characteristic may be selected from the group of: a composite stretchability and a composite strength.

In any embodiments discussed herein, the second material may include a thermoplastic material.

In any of the various embodiments discussed herein, an upper may include a third polymer thread set stitched in a third pattern on an outer surface of a base layer, the third pattern including polymer thread lines oriented in a third direction different from the direction of a first pattern and a second pattern.

In any of the various embodiments discussed herein, at least a portion of the third polymer thread set may overlap at least a portion of the first polymer thread set in a second overlap area. In some embodiments, at least portion of the third polymer thread set and at least a portion of the first polymer thread set that overlap may be bonded to each other via coatings of the polymer thread in the first polymer thread set and the polymer thread in the third polymer thread set.

In any of the various embodiments discussed herein, an upper may include a backing thread disposed on a second outer surface of the base layer opposite the first outer surface and the first polymer thread set may be stitched around the backing thread to secure the first polymer thread set to the base layer.

In any of the various embodiments discussed herein, the first pattern may be based on a biometric data profile for an individual.

Some embodiments may include an upper for an article of footwear, the upper including a base layer defining a least a portion of the upper and one or more polymer threads stitched to the base layer, the one or more polymer threads having a core including a first material and a coating including a second material, where the melting point of the first material is higher than the melting point of the second material, where the one or more polymer threads are bonded to the base layer via the coating of the polymer thread, and where the one or more polymer threads include a first polymer thread set stitched in a first pattern on a first area of an outer surface of the base layer.

In any of the various embodiments discussed herein, the second material may include thermoplastic polyurethane. In any of the various embodiments discussed herein, the first material may be polyester.

In any of the various embodiments discussed herein, the first polymer thread set may be stitched in a zigzag pattern in the first area.

In any of the various embodiments discussed herein, an upper may include a second polymer thread set stitched in a second pattern on a second area of the outer surface of the base layer, the second pattern being different from the first pattern. In any of the various embodiments discussed herein, the second area may overlap at least a portion of the first area.

In any of the various embodiments discussed herein, the portion of the first polymer thread set and the portion of the second polymer thread set that overlap may be bonded to each other via the coating of the polymer thread in the first thread set and the polymer thread of the second thread set.

In any of the various embodiments discussed herein, the first polymer thread set may be oriented in a first direction on the first area of the outer surface and the second polymer thread set may be oriented in a second direction on the second area of the outer surface of the base layer, the second direction being different from the first direction.

In any of the various embodiments discussed herein, the first polymer thread set may be stitched in a first zigzag pattern where apexes of the first zigzag pattern are separated by a first distance and the second polymer thread set may be stitched in a second zigzag pattern where apexes of the second zigzag pattern are separated by a second distance different from the first distance.

In any of the various embodiments discussed herein, an upper may include a third polymer thread set stitched in a third pattern on a third area of the outer surface of the base layer, the third pattern being different from the first pattern and the second pattern. In any of the various embodiments discussed herein, the third area may overlap at least a portion of the first area. In any of the various embodiments discussed herein, the portion of the first polymer thread set and the portion of the third polymer thread set that overlap may be bonded to each other via the coating of the polymer threads. In any of the various embodiments discussed herein, the third area may overlap at least a portion of the second area. In any of the various embodiments discussed herein, the portion of the second polymer thread set and the portion of the third polymer thread set that overlap may be bonded to each other via the coating of the polymer thread in the second thread set and the polymer thread in the third thread set.

In any of the various embodiments discussed herein, at least one characteristic of the base layer may vary between the first area and the second area. In some embodiments, the characteristic may be selected from the group of: ventilation, stretchability, and strength.

In any of the various embodiments discussed herein, an upper may include a reinforcement area stitched around a peripheral edge of the first area.

In any of the various embodiments discussed herein, the first pattern may be based on a biometric data profile for an individual. In any of the various embodiments discussed herein, the first pattern and the second pattern may be based on a biometric data profile for an individual.

In any of the various embodiments discussed herein, the one or more polymer threads may be embroidered on the base layer.

In any of the various embodiments discussed herein, an upper may include a backing thread disposed on a second outer surface of the base layer opposite the first outer surface and the one or more polymer threads may be stitched around the backing thread to secure the polymer threads to the base layer.

In any of the various embodiments discussed herein, an upper may include a heel counter and the base layer may be coupled to the heel counter.

In any of the various embodiments discussed herein, base layer may be selected from the group of: a woven layer, a non-woven layer, a knitted layer, and a leather layer.

Some embodiments may include an article of footwear including a sole and an upper coupled to the sole, the upper including a base layer defining a least a portion of the upper and one or more polymer threads stitched to the base layer in one or more patterns on a surface of the base layer, the one or more polymer threads including a thermoplastic material coating that bonds the polymer threads to the base layer.

In any of the various embodiments discussed herein, the one or more polymer threads may include a plurality of polymer thread sets arranged in different patterns on the surface of the base layer.

In any of the various embodiments discussed herein, the plurality of polymer thread sets may overlap at least partially on the surface of the base layer.

In any of the various embodiments discussed herein, each polymer thread set may provide a directional characteristic to a portion of the upper. In some embodiments, the directional characteristic may be selected from the group of: directional stretchability and directional strength.

In any of the various embodiments discussed herein, the plurality of polymer thread sets may be arranged in zigzag patterns on the surface of the base layer.

In any of the various embodiments discussed herein, a peripheral region of the base layer may include a reinforcement area defined by one or more polymer threads stitched on the reinforcement area. In any of the various embodiments discussed herein, the base layer may be coupled to the sole along at least a portion of the reinforcement area.

In any of the various embodiments discussed herein, the upper may be coupled to the sole at a sole connection area along a border of the base layer and one or more polymer threads may be disposed in the connection area.

In any of the various embodiments discussed herein, the article of footwear may include a heel counter coupled to the base layer. In any of the various embodiments discussed herein, a peripheral region of the base layer may include a reinforcement area defined by one or more polymer threads stitched on the reinforcement area and the base layer may be coupled to the heel counter along at least a portion of the reinforcement area.

In any of the various embodiments discussed herein, the one or more polymer threads may be visibly exposed on the upper.

Some embodiments may include a method of making an article of footwear, the method including stitching one or more polymer threads in one or more patterns on an outer surface of a base layer, the one or more polymer threads having a core including a first material and a coating including a second material, where the melting point of the first material is higher than the melting point of the second material; bonding the one or more polymer threads to the base layer by heating the second material of the one or more polymer threads to a minimum temperature; and coupling the base layer to one or more footwear components to form an article of footwear.

In any of the various embodiments discussed herein, the footwear components may be selected from the group of: a sole, a heel counter, and a lace component.

In any of the various embodiments discussed herein the one or more polymer threads may be embroidered on the base layer.

In any of the various embodiments discussed herein, the one or more polymer threads may be stitched to the base layer with a computer numerical controlled stitching machine.

In any of the various embodiments discussed herein, bonding the one or more polymer threads to the base layer may include applying pressure to the polymer threads and the base layer.

In any of the various embodiments discussed herein, the minimum temperature for bonding the one or more polymer threads may be in the range of 180 degrees C. to 80 degrees C.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention(s) and the appended claims in any way.

The present invention(s) have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention(s). Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention(s) should not be limited by any of the above-described exemplary embodiments, but should be defined only in accordance with the following claims and their equivalents.

What is claimed is:

1. A method of making an upper for an article of footwear, the method comprising:
    collecting a biometric data profile;
    based on the biometric data profile, determining one or more stitch parameters for a first thread pattern;
    stitching thread in the first pattern on an outer surface of a base layer for at least a portion of the upper for the article of footwear, the first pattern comprising thread lines oriented in a first direction; and
    stitching thread in a second pattern on the outer surface of the base layer, the second pattern comprising thread lines oriented in a second direction that is different from the first direction,
    wherein at least a portion of the second pattern overlaps at least a portion of the first pattern in an overlap area on the outer surface of the base layer.

2. The method of claim 1, wherein stitching thread in the second pattern is based on the biometric data profile.

3. The method of claim 1, wherein collecting the biometric data profile comprises obtaining a previously collected and stored biometric data profile for an individual.

4. The method of claim 1, wherein collecting the biometric data profile comprises obtaining a standard biometric data profile for a group of individuals.

5. The method of claim 1, wherein the one or more stitch parameters is selected from the group consisting of: (i) a type of thread, (ii) a stitching direction of the thread lines, (iii) a size and shape of an area stitched with the thread lines, (iv) a size and shape of the overlap area, (v) a distance between stitch points in the thread lines, (vi) an oscillating pattern of the thread lines, (vii) a distance between apexes in the first pattern, and (viii) the denier of the thread in the first pattern.

6. The method of claim 1, wherein the biometric data profile comprises one or more gait characteristics for an individual or group of individuals.

7. The method of claim 6, wherein the biometric data profile comprises one or more personal characteristics for an individual, the one or more personal characteristics selected from the group consisting of: the individual's name, prior injury information for the individual, the individual's height, the individual's weight, the individual's shoe size, an athletic goal for the individual, an intended athletic environment or terrain for the individual, an intended athletic activity duration for the individual, an intended athletic activity frequency for the individual, and an intended athletic activity distance for the individual.

8. The method of claim 1, wherein the thread in the first pattern comprises polymer thread.

9. The method of claim 8, further comprising thermally fusing the polymer thread of the first pattern to the base layer by heating the polymer thread of the first pattern to thereby directly bond the polymer thread of the first pattern to the base layer.

10. The method of claim 8, wherein the thread in the second pattern comprises polymer thread.

11. The method of claim 10, further comprising thermally fusing the polymer thread of the first pattern and the second pattern to the base layer by heating the polymer thread of the first pattern and the second pattern to thereby directly bond the polymer thread of the first pattern and the second pattern to the base layer.

12. The method of claim 10, further comprising thermally fusing the polymer thread of the first pattern to the second pattern in the overlap area by heating the polymer thread of the first pattern and the second pattern to thereby directly bond the polymer thread of the first pattern to the polymer thread of the second pattern.

13. The method of claim 8, wherein the polymer thread of the first pattern comprises a core comprising a first material and a thermoplastic coating comprising a second material, wherein the melting point of the first material is higher than the melting point of the second material.

14. The method of claim 13, further comprising thermally fusing the polymer thread of the first pattern to the base layer by heating the second material to thereby directly bond the second material to the base layer.

15. The method of claim 1, wherein the thread lines of the first pattern and the second pattern are secured to the base layer at a plurality of stitch points with backing thread disposed on a back surface of the base layer opposite the outer surface.

16. A method of making an article of apparel, the method comprising:
    collecting a biometric data profile;
    based on the biometric data profile, determining one or more stitch parameters for a first pattern;

embroidering thread in the first pattern on an outer surface of a base layer for at least a portion of the article of apparel;

based on the biometric data profile, determining one or more stitch parameters for a second pattern; and embroidering thread in the second pattern on an outer surface of the base layer, wherein at least a portion of the second pattern overlaps at least a portion of the first pattern in an overlap area on the outer surface of the base layer.

17. The method of claim 16, wherein the thread in the first pattern and the second pattern comprises thermoplastic polymer thread.

18. The method of claim 17, further comprising thermally fusing the thermoplastic polymer thread of the first pattern and the second pattern to the base layer by heating the thermoplastic polymer thread of the first pattern and the second pattern to thereby directly bond the thermoplastic polymer thread of the first pattern and the second pattern to the base layer.

19. The method of claim 18, wherein thermally fusing the thermoplastic polymer thread of the first pattern and the second pattern is based on the biometric data profile.

20. The method of claim 1, wherein the thread of the first pattern comprises polymer thread, wherein the method further comprises thermally fusing the polymer thread of the first pattern to the base layer by heating the polymer thread of the first pattern to thereby directly bond the polymer thread of the first pattern to the base layer, and wherein thermally fusing the polymer thread of the first pattern is based on the biometric data profile.

21. The method of claim 1, wherein a size and shape of the overlap area is based on the biometric data profile.

22. A method of making an article of apparel, the method comprising:

collecting a biometric data profile;

based on the biometric data profile, embroidering polymer thread in a first pattern on an outer surface of a base layer for at least a portion of the article of apparel;

based on the biometric data profile, embroidering thread in a second pattern on an outer surface of the base layer; and based on the biometric data profile, thermally fusing the polymer thread of the first pattern to the base layer to thereby directly bond the polymer thread to the base layer, wherein at least a portion of the second pattern overlaps at least a portion of the first pattern in an overlap area on the outer surface of the base layer.

* * * * *